US006117641A

United States Patent [19]
Berlin et al.

[11] Patent Number: 6,117,641
[45] Date of Patent: Sep. 12, 2000

[54] ASSAYS AND REAGENTS FOR IDENTIFYING ANTI-FUNGAL AGENTS AND USES RELATED THERETO

[75] Inventors: Vivian Berlin, Dunstable, Mass.; David E. Levin, Owens Hills, Md.; Yoshikazu Ohya, Tokyo, Japan

[73] Assignees: Mitotix, Inc., Cambridge, Mass.; The John Hopkins University, Baltimore, Md.

[21] Appl. No.: 08/631,319

[22] Filed: Apr. 11, 1996

[51] Int. Cl.[7] .................... G01N 33/53; G01N 33/573; A61K 39/012; C12Q 1/48

[52] U.S. Cl. .................... 435/7.1; 424/274.1; 435/7.1; 435/7.4; 435/15

[58] Field of Search ............................. 435/7.1, 7.4, 15; 424/274.1

[56] References Cited

U.S. PATENT DOCUMENTS

| | | | |
|---|---|---|---|
| 5,202,456 | 4/1993 | Rando | 558/438 |
| 5,470,832 | 11/1995 | Gibbs et al. | 514/18 |
| 5,484,724 | 1/1996 | El-Sherbeini et al. | 435/193 |

FOREIGN PATENT DOCUMENTS

| | | |
|---|---|---|
| 621 342 A1 | 4/1993 | European Pat. Off. |
| 0644 199 A1 | 3/1995 | European Pat. Off. |
| WO 91/13988 | 9/1991 | WIPO |
| WO 94/13818 | 6/1994 | WIPO |
| WO 95/10625 | 4/1995 | WIPO |

OTHER PUBLICATIONS

Ohya et al., "Suppression of Yeast Geranylgeranyl Transferase I Defect by Alternative Prenylation of Two Target GTPases Rho1p and Cdc 42P," Molecular Biology of the Cell, 4(10): 1017–1025, Oct. 1993.

Ohya et al., "Mutational analysis of the B–Subunit of yeast geranylgeranyl transferase I," Mol. Gen. Genet. 252(1/2): 1–10, 1996.

Antonsson et al., "Protein Kinase C in Yeast," *The Journal of Biological Chemistry*, vol. 269, No. 24 pp. 16821–16828 (Jun. 17, 1994).

Bin He et al, "RAM2, an essential gene of yeast, and RAM1 encode the two polypeptide components of the farnesyltransferase that prenylates a–factor and Ras proteins," *Proc. Natl. Acad. Sci.*, vol. 88, pp. 11373–11377, (Dec. 1991).

Bussey, Howard, "Cell shape determination: a pivotal role for Rho," *Science*, vol. 272, pp. 224–225, (Apr. 1996).

Bukhtiyarov et al, "Photoreactive Analogues of Prenyl Diphosphates as Inhibitors and Probes of Human Protein Farnesyltransferase and Geranylgeranyltransferase Type I," *The Journal of Biological Chemistry*, vol. 270, No. 32, pp. 19035–19040 (Aug. 11, 1995).

Caldwell, et al, "Consequences of altered isoprenylation targets on a–factor export and bioactivity," *Proc. Natl. Acad. Sci. USA*, vol. 91, pp. 1275–1279 (Feb. 1994).

Chen, et al, "High level expression of mammalian protein farnesyltransferase in baculovirus system," *The American Society for Biochemistry and Molecular Biology, Inc.* vol. 265, No. 13, pp. 9675–9684, May 1993.

Dawson, et al., "A Capillary Electrophoresis–Based Assay for Protein Kinases and Protein Phosphatases Using Peptide Substrates," *Analytical Biocemistry* 220, pp. 340–345 (1994).

Diaz et al, "The schizosaccharomyces pombe cwg2+ gene codes for the beta subunit of geranylgeranyltransferase type I required for beta–glucan systhesis," *The Embo Journal*, vol. 12, No. 13, 1993, pp. 5245–5254.

Drgonova et al, "Rho1p, a yeast protein at the interface between cell polarization and morphogenesis," *Science*, vol. 272, pp. 277–279, (Apr. 1996).

Frost et al, "Characterization of (1,3)–beta–glucan synthase in *Candida albicans*: microsomal assay from the yeast or mycelial morphological forms and a permeabilized whole–cell assay," *Microbiology*, pp. 140, 2239–2246 (Sep. 1994).

Georgopapadakou et al, "The fungal cell wall as a drug target," *Trends in Microbiology*, vol. 3, No. 3 (Mar. 1995).

Gomez et al, "Purified yeast protein farnesyltransferase is structurally and functionally similar to its mammalian counterpart," *Biochem J.*, 289, pp. 25–31 (1993).

Goueli, et al, "A novel and simple method to assay the activity of individual protein kinases in a crude tissue extract," *Analytical Biochemistry* 225, pp. 10–17 (1995).

Johnson, et al, "Molecular characterization of CDC42, a *saccharomyces cerevisiae* gene involved in the development of cell polarity," *The Journal of Cell Biology*, vol. 111, No. 1, pp. 779–788, (Jul. 1990).

Kim et al, "Characterization of yeast geranylgeranyl transferase type I expressed in E. coli," *Mol. Cells*, vol. 6, No. 5, pp. 602–608, 1996.

Madaule et al, "Characterization of two members of the rho gene family from the yeast *saccharomyces cerevisiae*," *Proc. Natl. Acad. Sci., USA*, vol. 84, pp. 779–783 (Feb. 1987).

Mazzei, et al, A $Ca^{2+}$–independent protein kinase C from fission yeast, *The Journal of Biological Chemistry*, vol. 268, No. 10, pp. 7401–7406 (Apr. 1993).

Mitsuzawa et al, "Mutant farnesyltransferase β subunit of *saccharomyces cerevisiae* that can substitute for geranylgeranyltransferase type I β subunit," *Proc. Natl. Acad. Sci.* vol. 92, pp. 1704–1708 (Feb. 1995).

Nakano et al, "Isolation and sequencing of two cDNA clones encoding Rho proteins from the fission yeast schizosaccharomyces pombe," *Gene*, vol. 155, pp. 199–122 (Mar. 21, 1995).

(List continued on next page.)

*Primary Examiner*—James C. Housel
*Assistant Examiner*—Ja-Na A. Hines
*Attorney, Agent, or Firm*—Matthew Vincent; Chinh Pham; Foley, Hoag & Eliot, LLP

[57] ABSTRACT

The present invention relates to rapid, reliable and effective assays for screening and identifying pharmaceutically effective compounds that specifically inhibit the biological activity of fungal GTPase proteins, particularly GTPases involved in cell wall integrity, hyphael formation, and/or other cellular functions critical to pathogenesis.

29 Claims, 14 Drawing Sheets

OTHER PUBLICATIONS

Omer et al, "Protein prenylation in eukaryotic microorganisms: genetics, biology and biochemistry," *Molecular Microbiology,* 11(2) pp. 219–225 (1994).

Omer et al, "Characterization of recombinant human farnesyl–protein transferase: cloning, expression, farnesyl diphosphate binding, and functional homology with yeast prenyl–protein transferases," *Biochemistry,* vol. 32, No. 19 (1993).

Patent Abstracts of Japan, vol. 14, No. 377 (C–0748), Aug. 15, 1990 of JP 21 038983 A (Takeda Chem. Ind. Ltd.), May 28, 1990.

Pickett et al, "A fluorescence assay for geranylgeranyl transferase type I," *Analytical Biochemistry 225,* pp. 60–63 (1995).

Qadota et al, "Conditional lethality of a yeast strain expressing human RHOA in place of RHO1," *Proc. Natl. Acad. Sci.,* vol. 91, pp. 9317–9321 (Sep. 1994).

Qadota et al, "Identificationof yeast Rho 1p GTPase as a regulatory subunit of 1,3–beta–glucan synthase," *Science,* vol. 272, pp. 279–281 Apr. 1996).

Roskoski, Jr., et al, "Farnesyl–protein transferase and geranylgeranyl–protein transferase assays using phosphocellulose paper absoprtion," *Analytical Biochemistry 222,* pp. 275–280 (1994).

Roskoski, Jr., Robert, "Assays of Protein Kinase," *Methods in Enzymology,* vol. 99, pp. 3–6 (1983).

Watanabe, et al, *Saccharomyces cerevisiae* PLC1 encodes a protein kinase C (PKC) homolog with a substrate specificity similar to that of mammalian PKC, *The Journal of Biological Chemistry,* vol. 269, No. 24, pp. 16829–16836 (Jun. 1994).

Yokoyama, et al, "Mammalian protein Geranylgeranyltransferase–I: substrate specificity, Kinetic mechanism, metal requirements, and affinity labeling," *Biochemistry* 1995, 34 pp. 1344–1354.

Zhang, et al, "Properties and kinetic mechanism of recombinant mammalian protein geranyltransferase type I," *The Journal of Biological Chemistry,* vol. 269, No. 38, pp. 23465–23470 (Sep. 1994).

Zhang et al, cDNA cloning and epxression of rat and human protein geranylgeranyltransferasse type–I, *The Journal of Biological Chemistry,* vol. 269, No. 5, pp. 3175–3180 (Feb. 1994).

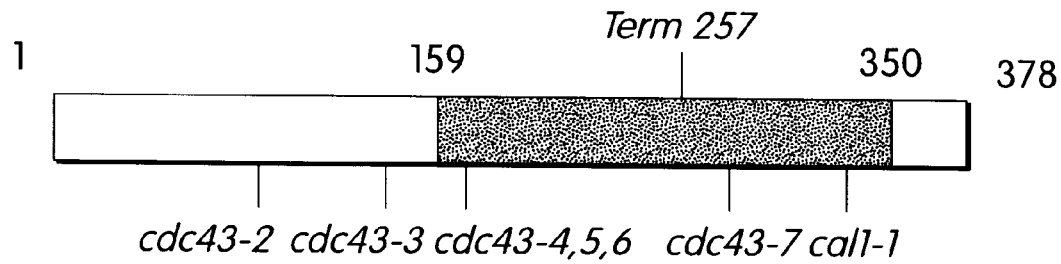

Cal1p/Cdc43p

| | |
|---|---|
| Cdc43-2P (S85F)<br>S. pombe<br>RAT<br>HUMAN | TENTVIS--GFVG<br>kEskgIkysGFqa<br>edrsnldrcGFrG<br>edrsnlnrcGFrG |
| CDC43-3P (C138Y)<br>S. POMBE<br>RAT<br>HUMAN | ARFVSKCQRPDRG<br>knFVelCktsq-G<br>Aglral-QleD-G<br>Aglral-QleD-G |
| CDC43-4,5,6P<br>(A171V/T/V)<br>S. POMBE<br>RAT<br>HUMAN | LRFCYIAVAILYI<br>mRqlYmA-----t<br>mRFvYcA-----s<br>mRFvYcA-----s |
| CDC43-7P (R280C)<br>S. POMBE<br>RAT<br>HUMAN | DGGFQGRENKFAD<br>sGGlnGRtNKdvD<br>qnGyhGRpNKpvD<br>qnGyhGRpNKpvD |
| CAL1-1P (G328S)<br>S. POMBE<br>RAT<br>HUMAN | QKTLTGGFSKNDE<br>Qh-alGGFSKTPG<br>dr-LvGGFaKwpd<br>dr-LvGGFaKwpd |

Fig. 10

SEQUENCE LISTING (1) GENERAL INFORMATION:

(iii) NUMBER OF SEQUENCES:   3

(2) INFORMATION FOR SEQ ID NO:1:

(i) SEQUENCE CHARACTERISTICS:
        (A) LENGTH:29 base pairs
        (B) TYPE:nucleic acid
        (C) STRANDEDNESS:single
        (D) TOPOLOGY:linear (ii) MOLECULE TYPE:   Other nucleic acid (iv) ANTI-SENSE:   No (xi) SEQUENCE DESCRIPTION: SEQ ID NO: 1:

CCATCGATCA TATGTGTCAA GCTAGGAAT                                    29

(2) INFORMATION FOR SEQ ID NO:2:

(i) SEQUENCE CHARACTERISTICS:
        (A) LENGTH:33 base pairs
        (B) TYPE:nucleic acid
        (C) STRANDEDNESS:single
        (D) TOPOLOGY:linear (ii) MOLECULE TYPE:   Other nucleic acid (iv) ANTI-SENSE:   Yes (xi) SEQUENCE DESCRIPTION: SEQ ID NO: 2:

GCGGGTACCC TGCAGTCAAA AACAGCACCT TTT                               33

-continued (2) INFORMATION FOR SEQ ID NO:3:

(i) SEQUENCE CHARACTERISTICS:
        (A) LENGTH:42 base pairs
        (B) TYPE:nucleic acid
        (C) STRANDEDNESS:single
        (D) TOPOLOGY:linear (ii) MOLECULE TYPE:  Other nucleic acid (iv) ANTI-SENSE:  Yes (xi) SEQUENCE DESCRIPTION: SEQ ID NO: 3:

GGTAGCTTGA CACATCAAAA CTCCTCCTGC AGATTTATTT TG           42

ASSAYS AND REAGENTS FOR IDENTIFYING ANTI-FUNGAL AGENTS AND USES RELATED THERETO

GOVERNMENT FUNDING

Work described herein was supported in part by funding from the National Institute of Health. The United States Government has certain rights in the invention.

BACKGROUND OF THE INVENTION

Fungal infections of humans range from superficial conditions, usually caused by dermatophytes or Candida species, that affect the skin (such as dermatophytoses) to deeply invasive and often lethal infections (such as candidiasis and cryptococcosis). Pathogenic fungi occur worldwide, although particular species may predominate in certain geographic areas.

In the past 20 years, fungal infections have increased dramatically—along with the numbers of potentially invasive species. Indeed, fungal infections, once dismissed as a nuisance, have begun to spread so widely that they are becoming a major concern in hospitals and health departments. Fungal infections occur more frequently in people whose immune system is suppressed (because of organ transplantation, cancer chemotherapy, or the human immunodeficiency virus), who have been treated with broad-spectrum antibacterial agents, or who have been subject to invasive procedures (catheters and prosthetic devices, for example). Fungal infections are now important causes of morbidity and mortality of hospitalized patients: the frequency of invasive candidiasis has increased tenfold to become the fourth most common blood culture isolate (Pannuti et al. (1992) Cancer 69:2653). Invasive pulmonary aspergillosis is a leading cause of mortality in bone-marrow transplant recipients (Pannuti et al., supra), while *Pneumocystis carinii* pneumonia is the cause of death in many patients with acquired immunodeficiency syndrome in North America and Europe (Hughes (1991) Pediatr Infect. Dis J. 10:391). Many opportunistic fungal infections cannot be diagnosed by usual blood culture and must be treated empirically in severely immunocompromised patients (Walsh et al. (1991) Rev. Infect. Dis. 13:496).

The fungi responsible for life-threatening infections include Candida species (mainly *Candida albicans*, followed by *Candida tropicalis*), Aspergillus species, *Cryptococcus neoforms, Histoplasma capsulatum, Coccidioides immitis, Pneumocystis carinii* and some zygomycetes. Treatment of deeply invasive fungal infections has lagged behind bacterial chemotherapy.

There are numerous commentators who have speculated on this apparent neglect. See, for example, Georgopapadakou et al. (1994) Science 264:371. First, like mammalian cells, fungi are eukaryotes and thus agents that inhibit fungal protein, RNA, or DNA biosynthesis may do the same in the patient's own cells, producing toxic side effects. Second, life-threatening fungal infections were thought, until recently, to be too infrequent to warrant aggressive research by the pharmaceutical industry. Other factors have included:

(i) Lack of drugs. A drug known as Amphotericin B has become the mainstay of therapy for fungal infection despite side effects so severe that the drug is known as "amphoterrible" by patients. Only a few second-tier drugs exist.

(ii) Increasing resistance. Long-term treatment of oral candidiasis in AIDS patients has begun to breed species resistant to older anti-fungal drugs. Several other species of fungi have also begun to exhibit resistance.

(iii) A growing list of pathogens. Species of fungi that once posed no threat to humans are now being detected as a cause of disease in immune-deficient people. Even low-virulence baker's yeast, found in the human mouth, has been found to cause infection in susceptible burn patients.

(iv) Lagging research. Because pathogenic fungi are difficult to culture, and because many of them do not reproduce sexually, microbiological and genetic research into the disease-causing organisms has lagged far behind research into other organisms.

In the past decade, however, more antifungal drugs have become available. Nevertheless, there are still major weaknesses in their spectra, potency, safety, and pharmacokinetic properties, and accordingly it is desirable to improve the the panel of anti-fungal agents available to the practioner.

I. The fungal cell

The fungal cell wall is a structure that is both essential for the fungus and absent from mammalian cells, and consequently may be an ideal target for antifungal agents. Inhibitors of the biosynthesis of two important cell wall components, glucan and chitin, already exist. Polyoxins and the structurally related nikkomycins (both consist of a pyrimidine nucleoside linked to a peptide moiety) inhibit chitin synthase competitively, presumably acting as analogs of the substrate uridine diphosphate (UDP)-N-acetylglucosamine (chitin is an N-acetylglucosamine homopolymer), causing inhibition of septation and osmotic lysis. Unfortunately, the target of polyoxins and nikkomycins is in the inner leaflet of the plasma membrane; they are taken up by a dipeptide permease, and thus peptides in body fluids antagonize their transport.

In most fungi, glucans are the major components that strengthen the cell wall. The glucosyl units within these glucans are arranged as long coiling chains of $\beta$-(1,3)-linked residues, with occasional sidechains that involve $\beta$-(1,6) linkage. Three $\beta$-(1,3) chains running in parallel can associate to form a triple helix, and the aggregation of helicies produces a network of water-insoluble fibrils. Even in the chitin-rich filamentous aspergilli, $\beta$-(1,3)-glucan is required to maintain the integrity and form of the cell wall (Kurtz el al. (1994) Antimicrob Agents Chemother 38:1408–1489), and, in *P. carinii*, it is important during the life cycle as a constituent of the cyst (ascus) wall (Nollstadt et al. (1994) Antimicrob Agents Chemother 38:2258–2265.

In a wide variety of fungi, $\beta$-(1,3)-glucan is produced by a synthase composed of at least two subunits (Tkacz, J. S. (1992) in Emerging Targets in Antibacterial and Antifungal Chemotherapy (Sutcliffe and Georgopapadakou, eds), pp495–523, Chapman & Hall; and Kang et al. (1986) *PNAS* 83:5808–5812). One subunit is localized to the plasma membrane and is thought to be the catalytic subunit, while the second subunit binds GTP and associates with and activates the catalytic subunit (Mol et al. (1994) *J Biol Chem* 269:31267–31274).

Two groups of anticandidal antibiotics known in the art interfere with the formation of $\beta$-(1,3)-glucan: the papulacandins and the echinocandins (Hector el al. (1993) *Clin Microbiol Rev* 6:1–21). However, many of the papulacandins are not active against a variety of Candida species, or other pathogenic fungi including aspergillus. The echinocandins, in addition to suffering from narrow activity spectrum, are not in wide use because of lack of bioavilability and toxicity.

II. Protein Prenylation

Covalent modification by isoprenoid lipids (prenylation) contributes to membrane interactions and biological activities of a rapidly expnanding group of proteins (see, for example, Maltese (1990) FASEB J 4:3319; and Glomset et al. (1990) Trends Biochem Sci 15:139). Either farnesyl (15-carbon) or geranylgeranyl (20-carbon) isoprenoids can be attached to specific proteins, with geranylgeranyl being the predominant isoprenoid found on proteins (Fransworth et al. (1990) Science 247:320).

Three enzymes have been described that catalyze protein prenylation: farnesyl-protein transferase (FPTase), geranylgeranyl-protein transferase type I (GGPTase-I), and geranylgeranyl-protein transferase type-II (GGPTase-II, also called Rab GGPTase). These enzymes are found in both yeast and mammalian cells (Schafer et al. (1992) Annu. Rev. Genet. 30:209–237). FPTase and GGPTase-I are $\alpha/\beta$ heterodimeric enzymes that share a common $\alpha$ subunit; the $\beta$ subunits are distinct but share approximately 30% amino acid similarity (Brown et al. (1993). Nature 366:14–15; Zhang et al. (1994). J. Biol. Chem. 269:3175–3180). GGPTase II has different $\alpha$ and $\beta$ subunits and complexes with a third component (REP, Rab Escort Protein) that presents the protein substrate to the $\alpha/\beta$ catalytic subunits. Each of these enzymes selectively uses farnesyl diphosphate or geranylgeranyl diphosphate as the isoprenoid donor and selectively recognizes the protein substrate. FPTase farnesylates CaaX-containing proteins that end with Ser, Met, Cys, Gln or Ala. GGPTase-I geranylgeranylates CaaX-containing proteins that end with Leu or Phe. For FPTase and GGPTase-I, CaaX tetrapeptides comprise the minimum region required for interaction of the protein substrate with the enzyme. GGPTase-II modifies XXCC and XCXC proteins; the interaction between GGPTase-II and its protein substrates is more complex, requiting protein sequences in addition to the C-terminal amino acids for recognition. The enzymological characterization of these three enzymes has demonstrated that it is possible to selectively inhibit one with little inhibitory effect on the others (Moores et al. (1991) J. Biol. Chem. 266:17438).

GGPTase I transfers the prenyl group from geranylgeranyl diphosphate to the sulphur atom in the Cys residue within the CAAX sequence. *S Cerevisiae* proteins such as the Ras superfamily proteins Rho1, Rho2, Rsr1/Bud1 and Cdc42 appear to be GGPTase substrates (Madaule el al. (1987) PNAS 84:779–783; Bender et al. (1989) PNAS 86:9976–9980; and Johnson el al. (1990) J Cell Biol 111:143–152).

III. Protein Kinase C

Members of the family of phospholipid-dependent, serine/threonine-specific protein kinases known collectively as protein kinase C (PKC) respond to extracellular signals that act through receptor-mediated hydrolysis of phosphatidylinositol-4,5-bisphosphate to diacylglycerol (DAG) and inositol-1,4,5-trisphosphate ($IP_3$) (Hokin (1985) Annu. Rev. Biochem. 54, 205–235.). DAG serves as a second messenger to activate PKC (Takai et al. (1979) Biochem. Biophys. Res. Commun. 91, 1218–1224; Kishimoto et al. (1980) J. Biol. Chem. 255, 2273–2276; Nishizuka 1986) Science 233, 305–312; and Nishizuka (1988) Nature 334, 661–665), and $IP_3$ functions to mobilize $Ca^{2+}$ from intracellular stores (Berridge et al. (1984) Nature 312, 215–321). Twelve distinct subtypes of mammalian PKC have been reported to date (Nishizuka, Y. (1992) *Science* 258, 607–614; Decker et al. (1994) *TIBS* 19:73–77). The four initially identified isozymes, $\alpha$, $\beta I$, $\beta II$, and $\gamma$, are structurally closely related to each other and display similar catalytic properties.

Mammalian PKC is thought to play a pivotal role in the regulation of a host of cellular functions through its activation by growth factors and other agonists. These functions include cell growth and proliferation, release of various hormones, and control of ion conductance channels. Indirect evidence suggests that PKC induces the transcription of a wide array of genes, including the proto-oncogenes c-myc, c-fos, and c-sis, human collagenase, metallothionein $II_A$, and the SV40 early genes.

The PKC1 gene of budding yeast encodes a homolog of the $\alpha$, $\beta$, and $\gamma$ isoforms of mammalian Protein Kinase C that regulates a MAPK-activation pathway. Loss of PKC1 function results in a cell lysis defect that is due to a deficiency in cell wall construction.

SUMMARY OF THE INVENTION

The present invention provides drug screening assays for identifying pharmaceutically effective compounds that specifically inhibit the biological activity of fungal GTPase proteins, particularly GTPases involved in cell wall integrity, hyphael formation and other cell functions critical to pathogenesis. Briefly, as described in greater detail below, Applicants have discovered the critical involvment of Rho-like GTPase activities in cell wall integrity. For instance, the fungal Rho1 GTPase is required for glucan synthase activity, copurifies with 1,3-$\beta$-glucan synthase, and is found to associate with the Gsc 1/Fks1 subunit of this complex in vivo. Rho1 is an regulatory subunit of 1,3-$\beta$-glucan synthase, and accordingly this interaction, and the resulting enzyme complex, are potential therapeutic targets for development of antifungal agents. Moreover, Rho1 is required for protein kinase C (PKC1) mediated MAPK activation, and confers upon PKC1 the ability to be stimulated by phosphatidylserine (PS), indicating that Rho1 controls signal transmission through PKC1. Loss of PKC1 activity results in cell lysis. Also, we demonstrate that prenylation of Rho1 by a geranylgeranyl transferase is a critical step to maintenance of cell wall integrity in yeast. As described in the appended examples, prenylation of Rho1 is required for sufficient glucan synthase activity. Loss of Rho1 prenylation results in cell lysis. In general, a salient feature of the subject assays is that each is generated to detect agents which are potentially cytotoxic to a fungal cell, rather than merely cytostatic. Moreover, given the uniqueness of the therapeutic fungal targets of the present assays, e.g., relative to homolgous proteins in mammalian cells, the therapeutic targeting of Rho-like GTPase(s) involvement in such interactions and complexes in yeast presents an opportunity to define anti-fungal agents which are highly selective for yeast cells relative to mammalian cells.

In one aspect, the present invention provides an assay for identifying potential antifungal agents by targeting the GGPTase/GTPase interaction. For instance, the assay can be run by forming a reaction mixture including (i) a fungal geranylgeranyl transferase (GGPTase), (ii) a substrate for the GGPTase, such as a target polypeptide comprising a fungal Rho-like GTPase such as Rho1, Rho2, Rsr1/Bud1 and Cdc42, or a polypeptide portion thereof including at least one of (a) a prenylation site which can be enzymatically prenylated by the GGPTase, or (b) a GGPTase binding sequence which specifically binds the GGPTase, and (iii) a test compound. The interaction of the target polypeptide with the GGPTase can be detected. A statistically significant decrease in the interaction of the target polypeptide and GGPTase in the presence of the test compound, relative to the level of interaction in the absence of the test compound (or other control), indicates a potential anti-fungal activity for the test compound.

The reaction mixture can be a reconstituted protein mixture, a cell lysate or a whole cell. For instance, the reaction mixture can be a prenylation system including an activated geranylgeranyl group, and the step of detecting the interaction of the target polypeptide with the GGPTase includes detecting conjugation of the geranylgeranyl group to the target polypeptide. In preferred embodiments of such prenylation systems at least one of the geranylgeranyl group and the target polypeptide has a detectable label, and the level of geranylgeranyl group conjugated to the target polypeptide is quantified by detecting the label in at least one of the target polypeptide, free geranylgeranyl groups, and geranylgeranyl-conjugated target polypeptide. As illustrated below, the substrate target can incorporate a fluorescent (or other) label, the fluorescent characterization of which is altered by the level of prenylation of the substrate target, e.g., the substrate target can be a dansylated peptide substrate of the fungal GGPTase.

In other embodiments, the step of detecting the interaction of the target polypeptide with the GGPTase includes detecting the formation of protein—protein complexes including the target polypeptide with the GGPTase. For example, at least one of the GGPTase and the target polypeptide can include a detectable label, and the level of GGPTase/target polypeptide complexes formed in the reaction mixture is quantified by detecting the label in at least one of the target polypeptide, the GGPTase, and GGPTase/target polypeptide complexes. Exemplary labels for such embodiments, and for the prenylation assays above, include radioisotopes, fluorescent compounds, enzymes, and enzyme co-factors. For instance, the detectable label can be a protein having a measurable activity, and one of the PKC or GTPase is fusion protein including the detectable label. In other exemplary embodiments, conjugation of the geranylgeranyl group to the target polypeptide is detected by an immunoassay.

Where the reaction mixture is a whole cell, the cell will preferably include heterologous nucleic acid recombinantly expressing one or more of the fungal GGPTase subunits and target polypeptide. In certain preferred embodiments, the cell will also include a heterologous reporter gene construct having a reporter gene in operable linkage with a transcriptional regulatory sequence sensitive to intracellular signals transduced by interaction of the target polypeptide and GGPTase.

In one preferred embodiment, the assay includes forming a cell-free reaction mixture including: (i) a fungal GGPTase, (ii) a GGPTase substrate, e.g., a target polypeptide comprising a fungal Rho-like GTPase, or a polypeptide portion thereof including a prenylation site, (iii) an activated geranylgeranyl group, (iv) a divalent cation, and (v) a test compound. The assay is derived to detect conjugation of the gernaylgernayl group of the target polypeptide in the reaction mixture, and a statistically significant decrease in the prenylation of the target polypeptide and GGPTase in the presence of the test compound, relative to an appropriate control, indicates a potential anti-fungal activity for the test compound.

In another preferred embodiment, the method utilizes an interaction trap system including (a) a first fusion protein comprising at least a portion of a fungal GGPTase subunit, (b) a second fusion protein comprising at least a portion of a fungal GTPase, and (c) a reporter gene, including a transcriptional regulatory sequence sensitive to interactions between the GGPTase portion of the first fusion protein and the GTPase portion of the second polypeptide. After contacting the interaction trap system with a candidate agent the level of expression of a reporter gene is measured and compared to the level of expression in the absence of the candidate agent. A decrease in the level of expression of the reporter gene in the presence of the candidate agent is indicative of an agent that inhibits interaction of the GGPTase and GTPase.

In still another embodiment, the assay is derived from a recombinant cell expressing a recombinant form of one or more of a fungal GGPTase and a fungal Rho-like GTPase. The cell is contacted with a test compound, and the level of interaction of the GGPTase and Rho-like GTPase is detected. A statistically significant change in the level of interaction of the GGPTase and Rho-like GTPase is indicative of an agent that modulates the interaction of those two proteins. In preferred embodiments, one or both of a GGPTase subunit or the Rho-like GTPase are fusion proteins, e.g., the fustion protein providing a detectable label and/or an affinity tag for purification. In a preferred embodiment, the Rho-like GTPase is a fusion protein further comprising a transcriptional regulatory protein, and level of prenylation of the Rho-like GTPase is detected by measuring the level of expression of a reporter gene construct which is sensitive to the transcriptional regulatory protein portion of the fusion protein, wherein inhibition of prenylation of the fusion protein results in loss of membrane partitioning of the fusion protein and increases expression of the reporter gene construct.

In other preferred embodiments, the level of interaction of the GGPTase and Rho-like GTPase is detected by detecting prenylation of the Rho-like GTPase.

In yet another preferred embodiment, the assay is generated from a set of cells in which prenylation of endogenous Rho-like GTPases by GGPTase I is made dispensible. According to this embodiment, the assay provides a first test cell in which one or more Rho-like GPTases are mutated to be a substrate for a farnesyl transferase expressed by the cell such that GGPTase I is dispensible for cell growth; and a second test cell identical to the first cell except that the Rho-like GTPases are substrates for GGPTase I and are indispensible for cell growth. The first and second cells are contacted with a candidate agent, and the level of prenylation of the Rho-like GTPases in first and second test cells are compared. A statistically significant decrease in the prenylation of the GTPases in the second test cell, relative to the level of prenylation of the GTPase in the first cell, is indicative of an agent that inhibits interaction of a GGPTase and GTPase.

Yet another aspect of the present invention, the subject assays are derived for detecting agents which disrupt the formation of, or function of fungal protein complexes including Rho-like GTPases and PKC proteins. In one embodiment, the assay provides a reaction mixture including a fungal Rho-like GTPase, a fungal protein kinase C (PKC), and a test compound. Interaction of the Rho-like GTPase and PKC is detected in the reaction mixture, wherein a statistically significant decrease in the interaction of the Rho-like GTPase and PKC in the presence of the test compound, relative to the level of interaction in the absence of the test compound, indicates a potential antifungal activity for the test compound.

The reaction mixture can be a reconstituted protein mixture, a cell lysate or a whole cell. In preferred embodiments, the reaction mixture is a kinase system including ATP and a PKC substrate, and the step of detecting interaction of the GTPase and PKC includes detecting phosphorylation of the PKC substrate by a PKC/GTPase complex. Preferably, at least one of the PKC substrate and ATP includes a detectable label, and the level of phosphorylation of the PKC substrate is quantified by detecting the label in at least one of the phosphorylated PKC substrate or ATP. For instance, the PKC substrate may include a fluorescent (or other) label, the fluorescent characterization of which is altered by the level of phosphorylation of the PKC substrate.

In other preferred embodiments, the step of detecting the interaction of the GTPase with the PKC includes detecting the formation of protein—protein complexes including the GTPase and PKC. For instance, at least one of the PKC and GTPase includes a detectable label, and the level of PKC/GTPase complexes formed in the reaction mixture is quantified by detecting the label in at least one of the GTPase, the PKC, and PKC/GTPase complexes. For instance, phosphorylation of the PKC substrate is detected by immunoassay.

Cell-based assays are also provided, including cells comprising reporter gene constructs sensitive to PKC/GTPase complexes. In one embodiment, PKC/GTPases interaction trap assays are used for drug screening according to the present invention.

In still another aspect of the present invention, the subject assays are derived for detecting agents which disrupt the formation of, or function of fungal protein complexes including Rho-like GTPases and glucan synthase complexes or subunits thereof. In a preferred embodiment, the assay includes forming a reaction mixture including a fungal Rho-like GTPase, a fungal glucan synthase complex or subunit thereof (collectively "GS protein"), and a test compound. The interaction of the Rho-like GTPase and GS protein can be detected in the reaction mixture. Similar to the assay embodiments set out above, a statistically significant decrease in the interaction of the Rho-like GTPase and GS protein in the presence of the test compound, relative to the level of interaction in the absence of the test compound, indicates a potential antifungal activity for the test compound.

The reaction mixture can be a reconstituted protein mixture, a cell lysate or a whole cell. In preferred embodiments, the reaction mixture is a glucan synthesis system including a GTP and a UDP-glucose, and the step of detecting interaction of the GTPase and GS protein includes detecting formation of glucan polymers in the reaction mixture, e.g., the UDP-glucose can include a detectable label, and the level of glucan polymer formation is quantified by detecting the labeled glucan polymers.

In other embodiments, the step of detecting the interaction of the GTPase with the GS protein includes detecting the formation of protein—protein complexes including the GTPase and GS protein. As above, at least one of the GS protein and GTPase can include a detectable label, and the level of GS protein/GTPase complexes formed in the reaction mixture is quantified by detecting the label in at least one of the GTPase, the GS protein, and GS protein/GTPase complexes. Alternatively, the formation of protein—protein complexes including the GTPase and GS protein is detected by an immunoassay.

As above, cell-based assays are also provided, including cells comprising reporter gene constructs sensitive to GS/GTPase complexes. Permeabilization of cells due to disruption of GS activity by the test compound can also be detected by loss of cytoplasmic localization or cytoplasmic exclusion (depending on the embodiment) of a detectable label.

For each of the assay embodiments set out above, the assay is preferably repeated for a variegated library of at least 100 different test compounds, though preferably libraries of at least $10^3$, $10^5$, $10^7$, and $10^9$ compunds are tested. The test compound can be, for example, small organic molecules, and/or natural product extracts.

Also, in preferred embodiments of the subject assay, one or more of the GTPase of other proteins which interacting with the GTPase (e.g., GGPTase subunits, PKC and glucan synthase subunits) are derived from a human pathogen which is implicated in mycotic infection.

The subject assay also preferably includes a further step of preparing a pharmaceutical preparation of one or more compounds identified as having potential antifungal activity.

Still another aspect of the invention concerns various compositions and reagents for performing the subject drug screening assays. For instance, the present invention provides a variety of recombinant cells expressing one or more different fungal proteins implicated as targets in the subject screening assays. In a preferred embodiment, the recombinant cell includes exogenous nucleic acid (e.g., expression vectors) encoding a fungal Rho-like GTPase. In a more preferred embodiment, the recombinant cell includes (i) exogenous nucleic acid(s) encoding one or more subunits of a fungal geranylgeranyl protein transferase (GGPTase), and (ii) exogenous nucleic acid encoding a fungal Rho-like GTPase or a fragment thereof including at least one of (a) a prenylation site which can be enzymatically prenylated by the GGPTase, or (b) a GGPTase binding sequence which specifically binds the GGPTase. In still other preferred embodiments, the cell inlcudes (i) exogenous nucleic acid encoding a fungal Rho-like GTPase, and (ii) exogenous nucleic acid encoding a fungal protein selected from the group consisting of a fungal protein kinase C (PKC) or one or more subunits of a fungal glucan synthase.

The nucleic acids encoding the GGPTase, GTPase, PKC and/or glucan synthase are preferably derived from a human pathogen which is implicated in mycotic infection. For instance, the recombinant genes can be derived from fungus involved in such mycotic infections as selected from a group consisting of candidiasis, aspergillosis, mucormycosis, blastomycosis, geotrichosis, cryptococcosis, chromoblastomycosis, penicilliosis, conidiosporosis, nocaidiosis, coccidioidomycosis, histoplasmosis, maduromycosis, rhinosporidosis, monoliasis, paraactinomycosis, and sporotrichosis. To further illustrate, the expression vectors can be generated from genes cloned from human pathogen selected from a group consisting of *Candida albicans, Candida stellatoidea, Candida tropicalis, Candida parapsilosis, Candida krusei, Candida pseudotropicalis, Candida quillermondii, Candida rugosa, Aspergillus fumigatus, Aspergillus flavus, Aspergillus niger, Aspergillus nidulans, Aspergillus terreus, Rhizopus arrhizus, Rhizopus oryzae, Absidia corymbifera, Absidia ramosa*, and *Mucor pusillus*. Another source for recombinant genes is the human pathogen is *Pneumocystis carinii*.

In preferred embodiments, the cell is a recombinantly manipulated yeast cell selected from the group consisting of such genuses as Kluyverei, Schizosaccharomyces, Ustilaqo and Saccharomyces, though a prefered host cell is the *Schizosaccharomyces cerivisae* cell. Moreover, the host cell can be constitutively or inducibly defective for an endogenous activity corresponding to one or more of the GGPTase and GTPase encoded by the exogenous nucleic acids.

In similar fashion, another aspect of the present invention concerns reconstituted protein mixtures or cell lysate mixtures including a recombinant fungal Rho-like GTPase, or a fragment thereof including at least one of (a) a prenylation site which can be enzymatically prenylated by the GGPTase, or (b) a GGPTase binding sequence which specifically binds the GGPTase, along with one or more of a recombinant fungal glucan synthase, a recombinant fungal GGPTase, and/or a recombinant fungal PKC. As above, the fungal target proteins are preferably derived from a human pathogen which is implicated in mycotic infection.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

BRIEF DESCRIPTION OF THE DRAWINGS

FIG. 1A The rho1-5 allele lyses at restrictive temperature. Yeast strains patched on a YPD plate were incubated at 23° C. for 3 days, then shifted overnight to 37° C. The patches were assayed in situ for release of alkaline phosphatase as an indication of cell lysis. 1, wild-type; 2, rho1-3; 3, rho1-5; 4, $pkc1^{ts}$ (stt1-1; SYT11-12A). FIG. 1B An episomal plasmid (YEp352) with or without PKC1 was transformed into the $rho1^{ts}$ mutants (rho1-3 and rho1-5). Transformants were streaked onto a YPD plate and incubated at 37° C. for 3 days.

FIG. 3A $^{HA}$Rho1 was immunoprecipitated from extracts of cells growing at 23° C. (lane 4), or shifted from 23° C. to 39° C. for 30 min (lane 6). $^{HA}$Rho1 immunoprecipitates (left) and whole-cell extracts (100 μg protein; right) were analyzed by immunoblot with anti-PKC1 antibodies (top panels), or with anti-HA (to detect $^{HA}$Rho1; bottom panels). Untagged Rho1 was used as a negative control (lanes 1, 2, and 7). Band indicated by * is derived from immunoprecipitating antibodies. FIG. 3B Recombinant GST-Rho1 (1 μg), purified from Sf9 insect cells and bound to glutathione agarose beads, was preloaded with the indicated guanine nucleotide (lanes 2–5). Soluble yeast cell extract (400 μg protein) containing $PKC1^{HA}$ was incubated with the beads (lanes 1, 3, and 5), and bound $PKC1^{HA}$ was detected by immunoblot analysis. A control in which naked glutathione agarose beads were used (lane 1) demonstrates dependence of $PKC1^{HA}$ binding on GST-Rho1.

FIG. 4A Phosphorylation of synthetic Bck1 peptide by $PKC1^{HA}$ immunoprecipitated from 50 μg of soluble yeast cell extract protein. Recombinant GST-Rho1 or GST-Cdc42 (1 μg) was preloaded with the indicated guanine nucleotide. Cofactors (80 μg/ml PS, 8 μg/ml DAG, and 100 μM $CaCl_2$) were added to the reaction where indicated. Lanes 1 and 2 are control reactions with no GTPase. Mean and standard error for three experiments is shown. FIG. 4B PS alone is sufficient to stimulate PKC1 fully in the presence of Rho1. Phosphorylation of Bck1 peptide by $PKC1^{HA}$ in the presence of GTPγS-bound GST-Rho1 and the indicated cofactors. Conditions were as in A, except for PMA (16 ng/ml). Concentrations of PS as low as 8 μg/ml fully activated PKC1 (data not shown).

FIG. 6A GS activity is thermolabile in $rho1^{ts}$ mutants. Crude extracts were made from cells growing at room temperature, and assayed for GS activity at the indicated temperatures in the presence of 50 μM GTPγS. FIG. 6B Reconstitution of GS activity in rho1-3 membranes with recombinant Rho1. GS activity in rho1-3 membrane fractions was measured at 37° C. in the presence of 1 μg of the indicated recombinant GTPase and 50 μM GTPγS (19). FIG. 6C Reconstituted GS activity requires GTP. GS activity in wild-type membranes or rho1-3 membranes complemented with 1 μg of GST-Rho1 was measured at 37° C. in the presence of the indicated guanine nucleotide (20 μM). Results are expressed as percent activity relative to GTPγS.

FIG. 8A Immunoblot analysis of Rho1 (upper) and Gsc1/Fks1 (lower) through purification (See reference 20 of Example 2). FIG. 8B GS specific activity through purification. Purification steps were: lane 1, membrane fraction; lane 2, detergent extract; lane 3, first product entrapment; lane 4, second product entrapment.

FIG. 9A Coimmunoprecipitation of Rho1 with Gsc1/Fks1 (21). Partially purified GS was incubated with anti-Gsc1/Fks1 monoclonal antibodies, 1A6 (lane 1) and 1F4 (lane 2), and anti-human endothelin B type receptor (lane 3) (3). Immunoprecipitates were analyzed by SDS-PAGE followed by immunoblotting. FIG. 9B Colocalization of Gsc1/Fks1 and Rho1 at sites of cell wall remodeling (See reference 22 of Example 2). Indirect immunofluorescence microscopy was used to visualize Gsc1/Fks1 and $^{HA}$Rho1 in double-stained cells.

FIG. 10. Alignments of the β-subunits of GGPTase-Is showing cal1/cdc43 mutations. Positions of the cal1/cdc43 mutations are shown under the box representing the CAL1/CDC43 coding region. The closed box represents the homologous region among the β-subunits of the protein isoprenyltransferase. Cluster was used to align Cal1p, and the β-subunits of the S. pombe, rat and human GGPTase-Is near the cal1/cdc43 mutation points.

DETAILED DESCRIPTION OF THE INVENTION

Figure 14:
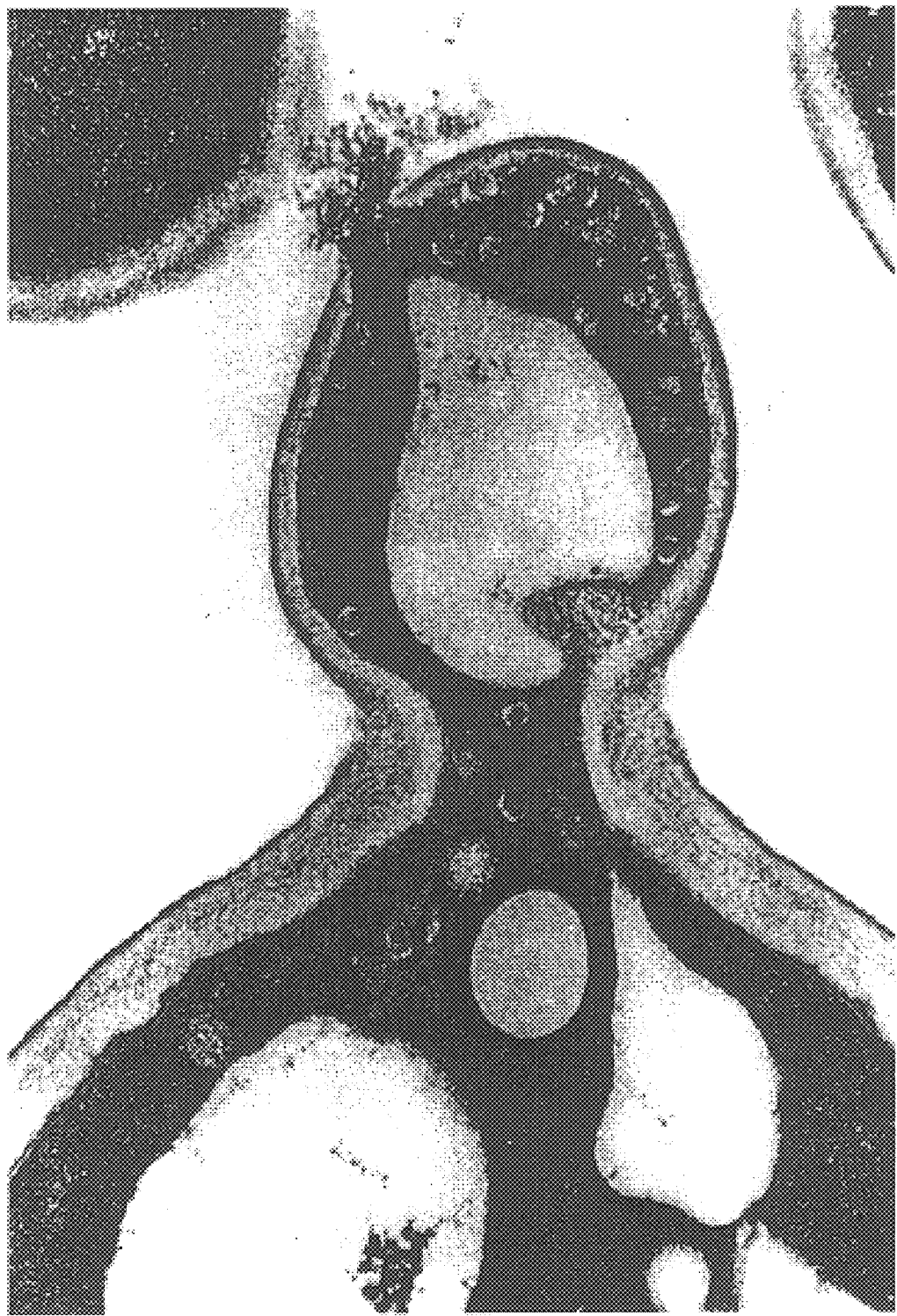
FIG. 14. Thin section electron micrograph of Pkc1-depleted cells demonstrating cell lysis.

The use of, and need for anti-fungal agents is widespread and ranges from the treatment of mycotic infections in animals; to additives in feed for livestock to promote weight gain; to disinfectant formulations. In general, a salient feature of effective anti-fungal agents is that the agent is cytotoxic to a fungal cell rather than only cytostatic. The mere knowledge that a particular protein is critical to cell growth is accordingly not sufficient to render that protein a suitable target for generation of anti-fungal agents. Rather, assays which are useful for identifying potential anti-fungal agents should target a fungal bioactivity which, when altered in a particular manner, results in cell death rather than quiescence or sporulation. For example, as is illustrated in FIG. 14, cell lysis is a preferred outcome to treatment with the potential antifungal agent in order to ensure destruction of the pathogen. Moreover, at least for anti-fungal agents which are to be administered to humans and other animals, the therapeutic index is preferably such that toxicity to the host is several orders of magnitude less than it is for the targeted fungus.

The present invention relates to rapid, reliable and effective assays for screening and identifying pharmaceutically effective compounds that specifically inhibit the biological activity of fungal GTPase proteins, particularly GTPases involved in cell wall integrity, hyphael formation, and other cellular functions critical to pathogenesis.

The cell wall of many fungus, as set out above, is required to maintain cell shape and integrity. The main structural component responsible for the rigidity of the yeast cell wall is 1,3-β-linked glucan polymers with some branches through 1,6-β-linkages. The biochemistry of the yeast enzyme catalyzing the synthesis of 1,3-β-glucan chains has been studied extensively, but little was previously known at the molecular level about the genes encoding subunits of this enzyme. Only a pair of closely related proteins (Gsc1/Fks1 and Gsc2/Fks2) had previously been described as subunits of the 1,3-β-glucan synthase (GS) (Inoue et al., (1995) Eur. J. Biochem. 231:845; and Douglas et al., (1994) PNAS 91:12907). GS activity in many fungal species, including S. cerevisiae, requires GTP or a non-hydrolyzable analog (e.g. GTPγS) as a cofactor, suggesting that a GTP-binding protein stimulates this enzyme (Mol et al. (1994) J. Biol. Chem. 269:31267).

As described in the appended examples, we demonstrate that the Rho1 GTPase activity is required for glucan synthase activity, copurifies with 1,3-β-glucan synthase, and is found to associate with the Gsc1/Fks1 subunit of this complex in vivo. Both proteins were also found to reside predominantly at sites of cell wall remodeling. Therefore, Rho1 is an regulatory subunit of 1,3-β-glucan synthase, and accordingly this interaction, and the resulting enzyme complex, are potential therapeutic targets for development of antifungal agents. Moreover, given the uniqueness of the yeast glucan cell wall relative to mammalian cells, the therapeutic targeting of Rho-like GTPase(s) involvement in glucan synthase complexes in yeast presents an opportunity to define antifungal agents which are highly selective for yeast cells relative to mammalian cells.

We have also discovered other interactions with Rho1-like GTPase which are consequential to cell integrity in yeast. As described in the appended examples, we find that Rho1 is required for protein kinase C (PKC1) mediated MAPK activation. Moreover, PKC1 co-immunoprecipitates with Rho1 in yeast extracts, and recombinant Rho1 associates with PKC1 in vitro in a GTP-dependent manner. Moreover, the data provided herein demonstrates that recombinant Rho1 confers upon PKC1 the ability to be stimulated by phosphatidylserine (PS), indicating that Rho1 controls signal transmission through PKC1. This applications provides the first example of a PKC isoform whose stimulation by cofactors is dependent on a GTPase, and provides the basis for yet other drug screening assays that target the interaction of a PKC and GTPase, or the catalytic activity of the resulting complex. Furthermore, no mammalian PKC activities have been reported to require a G-protein co-factor, suggesting that the fungal Rho/PKC complex represents a specific target for developing antiproliferative agents selective for yeast cells.

Finally, we have demonstrated that prenylation of Rho1 by a geranylgeranyl transferase is a critical step to maintenance of cell wall integrity in yeast. As described in the appended examples, prenylation of Rho1 is required for sufficient glucan synthase activity. Taken together with the results respecting Rho1's participation as a GS subunit, we demonstrate that not only is the prenylatin of Rho1 by GGPTase I critical to cell growth, but inhibition of the prenylation reaction is a potential target for developing a cytotoxic agent for killing various fungi. Moreover, the relatively high divergence between fungal and human GGPTase subunits suggests that selectivity for the fungal GGPTase activity may be obtained to provide antifungal agents having desirable therapeutic indices.

In one embodiment, the subject assay comprises a prenylation reaction system that includes a fungal geranylgeranyl protein transferase (GGPTase), a fungal GTPase protein, or a portion thereof, which serves as a prenylation target substrate, and an activated geranylgeranyl moiety which can be covalent attached to the prenylation substrate by the GGPTase. The level of prenylation of the target substrate brought about by the system is measured in the presence and absence of a candidate agent, and a statistically significant decrease in the level prenylation is indicative of a potential anti-fungal activity for the candidate agent.

As described below, the level of prenylation of the GTPase target protein can be measured by determining the actual concentration of substrate:geranylgeranyl conjugates formed; or inferred by detecting some other quality of the target substrate affected by prenylation, including membrane localization of the target. In certain embodiments, the present assay comprises an in vivo prenylation system, such as a cell able to conduct the target substrate through at least a portion of a geranylgeranyl conjugation pathway. In other embodiments, the present assay comprises an in vitro prenylation system in which at least the ability to transfer isoprenoids to the GTPase target protein is constituted. Still other embodiments provide assay format which detect protein—protein interaction between the GGPTase and a target protein, rather than enzymatic activity per se.

With respect to the interaction of the fungal GTPase with other cellular components, and the significance of those interactions to cell wall integrity, another aspect of the present invention relates to assays which seek to identify agents which alter protein—protein interactions involving a fungal GTPase and PKC or glucan synthase subunits, or which inhibit the catalytic activity of a protein complex resulting from such interactions. For instance, as described in more detail below, one therapeutic target of interest are glucan synthase complexes which include a Rho1-like GTPase. In another embodiment, the therapeutic target is a protein kinase C complex including a GTPase. The particular assay format selected will reflect the desire to identify compounds which disrupt protein—protein interactions and thereby alter the enzyme complex, or which disrupt the interaction with, and chemical alteration of a given substrate by the enzyme complex. For instance, the interaction with, and chemical alteration of a given substrate by the enzyme complex. For instance, the interaction of Rho1 with the glucan synthase subunit Gce1 can be the screening target in some embodiments, while the synthase activity of the resulting complex can be the screening target in other embodiments. Likewise, screening assays targeting PKC1/Rho1 complex can provide agents which disrupt the formation of the complex, or target the complex's interaction with substrate proteins.

As described herein, inhibitors of a fungal GTPase bioactivity refer generally to those agents which may act anywhere along the prenylation pathway, e.g., from the reaction steps leading up to and including conjugation of an isoprenoid to the GTPase target, to the interaction of the GTPase protein with other cellular proteins, such as glucan synthase subunits and/or PKC. A subset of this class of inhibitors comprises the prenylation inhibitors, which include those agents that act at the level of preventing conjugation of geranylgeranyl moieties to the target GTPase, rather than at the steps of protein—protein interactions involving the prenylated GTPase, e.g., as part of enzymatic complexes. Moreover, as will be clear from the following description, particular embodiments of the present assay can be chosen so as to discriminate between prenylation inhibitors and inhibitors of prenylated-GTPase complexes.

For convenience, certain terms employed in the specification, examples, and appended claims are collected here.

As used herein, "recombinant cells" include any cells that have been modified by the introduction of heterologous DNA. Control cells include cells that are substantially identical to the recombinant cells, but do not express one or more of the proteins encoded by the heterologous DNA, e.g., do not include or express a recombinant Rho1-like GTPase, a recombinant GGPTase, a recombinant glucan synthase and/or a recombinant PKC1.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, "heterologous DNA" or "heterologous nucleic acid" include DNA that does not occur naturally as part of the genome in which it is present or which is found in a location or locations in the genome that differs from that in which it occurs in nature. Heterologous DNA is not endogenous to the cell into which it is introduced, but has been obtained from another cell. Generally, although not necessarily, such DNA encodes RNA and proteins that are not normally produced by the cell in which it is expressed. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, isolated DNA that encodes a Rho1-like GTPase, a GGPTase, a glucan synthase and/or a PKC1.

"Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive (constitutively or inducibly). Inactivation may be partial or total.

"Complementation", with respect to genes of the host cell, means that at least partial function of inactivated gene of the host cell is supplied by an exogenous nucleic acid. For instance, yeast cells can be "mammalianized", and even "humanized", by complementation of Rho1 with mammalian homologs such as RhoA.

As used herein, a "reporter gene construct" is a nucleic acid that includes a "reporter gene" operatively linked to a transcriptional regulatory sequences. Transcription of the reporter gene is controlled by these sequences. The transcriptional regulatory sequences include the promoter and other regulatory regions, such as enhancer sequences, that modulate the activity of the promoter, or regulatory sequences that modulate the activity or efficiency of the RNA polymerase that recognizes the promoter, or regulatory sequences are recognized by effector molecules.

The term "substantially homologous", when used in connection with amino acid sequences, refers to sequences which are substantially identical to or similar in sequence, giving rise to a homology in conformation and thus to similar biological activity. The term is not intended to imply a common evolution of the sequences.

The terms "protein", "polypeptide" and "peptide" are used interchangeably herein.

As used here, the terms "geranylgeranyl protein transferase" and "GGPTase are art recognized and refer to the enzyme complexes responsible for the covalent modification of proteins with geranylgeranyl moieties. Particular reference to fungal GGPTases sub-types such as GGPTase-I, or the subunits of a fungal GGPTase, such as cdc43 and RAM2 (unless otherwise evident from the contest) is intended to refer generically to the analogous GGPTase complex and/or subunits in any fungal cell. Accordingly, reference to the subunit cdc43 (also referred to as CAL1 and DPR1) refers to the S. cerevisiae-i subunit as well as homologous proteins in that cell or other fungi which form a GGPTase I enzyme complex.

Likewise, the terms "Rho-like GTPase" and "fungal GTPase" will refer generally to GTPases related structurally to the yeast GTPases Rho1, Rho2, cdc42, and/or Rsr1/Bud1, whether the enzyme is isolated from S. cerevisiae or other fungi.

In similar fashion, the term "glucan synthase" refers generically to fungal enzymes involved in synthesis of a β-(1,3)-glucan and comprised of subunits including Gsc1 (also called Fks1) homologs and Rho-like GTPases. As above, reference to a "Gsc1 subunit" refers to the S. cerevisiae-i protein as well as structurally and functionally related homologs from other fungi.

The terms "PKC" and "PKC1" are also used generically to refer to protein kinase C homologs in fungi, and other fungal homologs of the PKC1 protein of S. cerevisiae, respectively.

The terms "fungi" and "yeast" are used interchangeably herein and refer to the art recognized group of eukaryotic protists known as fungi. That is, unless clear from the context, "yeast" as used herein can encompass the two basic morphologic forms of yeast and mold and dimorphisms thereof.

The present invention provides a systematic and practical approach for the identification of candidate agents able to inhibit one or more of the cellular functions of fungal GTPase proteins. In a general sense, the assays of the present invention evaluate the ability of a compound to modulate binding between a GTPase protein and another protein, whether the GTPase is acting as a subunit of a multiprotein complex or as a substrate for modification. The assays may be formatted to evaluate the ability of a compound to modulate (i) protein complexes which include a GTPase protein; (ii) the enzymatic activity of such multiprotein complexes; or (iii) the enzymatic activity which produces a prenylated GTPase.

Exemplary compounds which can be screened for activity against fungal GTPase activity include peptides, nucleic acids, carbohydrates, small organic molecules, and natural product extract libraries, such as isolated from animals, plants, fungus and/or microbes.

Cell-free Assay Formats

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins or cell-lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, a reaction mixture is generated to include a fungal GTPase polypeptide, compound(s) of interest, and a "target polypeptide", e.g., a protein, which interacts with the GTPase polypeptide, whether as a prenylating activity, or by some other protein—protein interaction. Exemplary target polypeptides include GGPTase activities such as GGPTase I, PKC homologs such as PKC1, and glucan synthase subunits such as Gsc1. Detection and quantification of the enzymatic conversion of the fungal GTPase, or the formation of complexes containing the fungal GTPase protein, provide a means for determining a compound's efficacy at inhibiting (or potentiating) complex the bioactivity of the GTPase. The efficacy of the compound can be assessed by generating dose response curves from data obtained using various concentrations of the test compound. Moreover, a control assay can also be performed to provide a baseline for comparison.

In one embodiment, the subject drug screening assay comprises a prenylation system, e.g. a reaction mixture which enzymatically conjugates isoprenoids to a target protein, which is arranged to detect inhibitors of the prenylation of a Rho-like GTPase with a geranylgeranyl group. For instance, in one embodiment of a cell-free prenylation system, one or more cell lysates including a fungal GGPTase, a fungal Rho-like GTPase (or substrate analog thereof), and an activated geranylgeranyl group are incubated with the test compound and the level of prenylation of the Rho-like GTPase substrate is detected. Lysates can be derived from cells expressing one or more of the relevant proteins, and mixed appropriately (or spilled) where no single lysate contains all the components necessary for generating the prenylation system. In preferred embodiments, one or more of the components, especially the substrate target, are recombinantly produced in a cell used to generate a lysate, or added by spiking a lysate mixture with a purified or semi-purified preparation of the substrate. These embodiments have several advantages including: the ability to use a labeled substrate, e.g. a dansylated peptide, or fusion protein for facilitating purification e.g. a Rho1-GST fusion protein; the ability to carefully control reaction conditions with respect to concentrations of reactants; and where targets are derived from fungal pathogens, the ability to work in a non-pathogenic system by recombinantly or synthetically producing by components from the pathogen for constituting the prenylation system.

The prenylates can be derived from any number of cell types, ranging from bacterial cells to yeast cells to cells from metazoan organisms including insects and mammalian cells. To illustrate, a fungal prenylation system can be reconstituted by mixing cell lysates derived from insect cells expressing fungal GGPTase subunits cloned into baculoviral expression vectors. For example, the exemplary GGPTase-I expression vectors described below in the section Reagents-i can be recloned into baculoviral vectors (e.g. pVL vectors), and recombinant GGPTase-I produced in transfected spodoptera-i fungiperda cells. The cells can than be lysed, and if the RAM2 and CDC43 subunits are produced by different sets of cells, cell lysates can be accordingly mixed to produce an active fungal GGPTase. The level of activity can be assessed by enzymatic activity, or by quantitating the level of expression by detecting, e.g., an exogenous tag added to the recombinant protein. Substrate and activated geranylgeranyl diphosphate can be added to the lysate mixtures. As appropriate, the transfected cells can be cells which lack an endogenous GGTase activity, or the substrate can be chosen to be particularly sensitive to prenylation by the exogenous fungal GGTPase relative to any endogenous activity of the cells. In other cell-free embodiments of the present assay, the prenylation system comprises a reconstituted protein mixture of at least semi-purified proteins. By semi-purified, it is meant that the proteins utilized in the reconstituted mixture have been previously separated from other cellular proteins. For instance, in contrast to cell lysates, the proteins involved in conjugation of geranylgeranyl moieties to a target protein, together with the target protein, are present in the mixture to at least 50% purity relative to all other proteins in the mixture, and more preferably are present at 90–95% purity. In certain embodiments of the subject method, the reconstituted protein mixture is derived by mixing highly purified proteins such that the reconstituted mixture substantially lacks other proteins which might interfere with or otherwise alter the ability to measure specific prenylation rates of the target GTPase substrate.

Each of the protein components utilized to generate the reconstituted prenylation system are preferably isolated from, or otherwise substantially free of, other proteins normally associated with the proteins in a cell or cell lysate. The term "substantially free of other cellular proteins" (also referred to herein as "contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described below and known in the art. By "purified", it is meant, when referring to the component protein preparations used to generate the reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either protein in its native state (e.g. as a part of a cell), or as part of a cell lysate, or that have been separated into components (e.g., in an acrylamide gel) but not obtained either as pure (e.g. lacking contaminating proteins) substances or solutions. The term isolated as used herein also refers to a component protein that is substantially free of cellular material or culture medium when produced by recombinant DNA techniques, or chemical precursors or other chemicals when chemically synthesized.

In the subject method, prenylation systems derived from purified proteins may have certain advantages over cell lysate based assays. Unlike the reconstituted protein system, the prenylation activity of a cell-lysate may not be readily controlled. Measuring kinetic parameters is made tedious by the fact that cell lysates may be inconsistent from batch to batch, with potentially significant variation between preparations. In vitro evidence indicates that prenyltransferases have the ability to cross-prenylate CAAX-related sequences, so that farnesyl transferase present in a lysate may provide an unwanted kinetic parameter. Moreover, cycling of prenylated proteins by guanine nucleotide dissociation inhibitor (GDI)-like proteins in the lysate could further complicate kinetics of the reaction mixture. Evaluation of a potential inhibitor using a lysate system is also complicated in those circumstances where the lysate is charged with mRNA encoding the GTPase substrate polypeptide or GGPTase activity, as such lysates may continue to synthesize proteins active in the assay during the development period of the assay, and can do so at unpredictable rates. Knowledge of the concentration of each component of the prenylation system can be required for each lysate batch, along with the overall kinetic data, in order to determine the necessary time course and calculate the sensitivity of experiments performed from one lysate preparation to the next. The use of reconstituted protein mixtures can allow more careful control of the reaction conditions in the prenylation reaction.

The purified protein mixture includes a purified preparation of the substrate polypeptide and a geranylgeranyl isoprenoid (or analog thereof) under conditions which drive the conjugation of the two molecules. For instance, the mixture can include a fungal GGPTase I complex including RAM2 and CDC43 subunits, a geranylgeranyl diphosphate, a divalent cation, and a substrate polypeptide, such as may be derived from Rho1.

Furthermore, the reconstituted mixture can also be generated to include at least one auxiliary substrate recognition protein, such as a Rab escort protein where GGPTase II is the prenylase employed in the reaction mixture.

Prenylation of the target regulatory protein via an in vitro prenylation system, in the presence and absence of a candidate inhibitor, can be accomplished in any vessel suitable for containing the reactants. Examples include microtitre plates, test tubes, and micro-centrifuge tubes. In such embodiments, a wide range of detection means can be practiced to score for the presence of the prenylated protein.

In one embodiment of the present assay, the products of a prenylation system are separated by gel electrophoresis, and the level of prenylated substrate polypeptide assessed, using standard electrophoresis protocols, by measuring an increase in molecular weight of the target substrate that corresponds to the addition of one or more geranylgeranyl moieties. For example, one or both of the target substrate and geranylgeranyl group can be labeled with a radioisotope such as $^{35}S$, $^{14}C$, or $^{3}H$, and the isotopically labeled protein bands quantified by autoradiographic techniques. Standardization of the assay samples can be accomplished, for instance, by adding known quantities of labeled proteins which are not themselves subject to prenylation or degradation under the conditions which the assay is performed. Similarly, other means of detecting electrophoretically separated proteins can be employed to quantify the level of prenylation of the target substrate, including immunoblot analysis using antibodies specific for either the target substrate or geranylgeranyl epitopes.

As described below, the antibody can be replaced with another molecule able to bind one of either the target substrate or the isoprenoid. By way of illustration, one embodiment of the present assay comprises the use of a biotinylated target substrate in the conjugating system. Indeed, biotinylated GGPTase substrates have been described in the art (c.f. Yokoyama et al. (1995) *Biochemistry* 34:1344–1354). The biotin label is detected in a gel during a subsequent detection step by contacting the electrophoretic products (or a blot thereof) with a streptavidin-conjugated label, such as a streptavidin linked fluorochrome or enzyme, which can be readily detected by conventional techniques. Moreover, where a reconstituted protein mixture is used (rather than a lysate) as the conjugating system, it may be possible to simply detect the target substrate and geranylgeranyl conjugates in the gel by standard staining protocols, including coomassie blue and silver staining.

In a similar fashion, prenylated and unprenylated substrate can be separated by other chromatographic techniques, and the relative quantities of each determined. For example, HPLC can be used to quantitate prenylated and unprenylated substrate (Pickett et al. (1995) *Analytical Biochem* 225:60–63), and the effect of a test compound on that ratio determined.

In another embodiment, an immunoassay or similar binding assay, is used to detect and quantify the level of prenylated target substrate produced in the prenylation system. Many different immunoassay techniques are amenable for such use and can be employed to detect and quantitate the conjugates. For example, the wells of a microtitre plate (or other suitable solid phase) can be coated with an antibody which specifically binds one of either the target substrate or geranylgeranyl groups. After incubation of the prenylation system with and without the candidate agent, the products are contacted with the matrix bound antibody, unbound material removed by washing, and prenylated conjugates of the target substrate specifically detected. To illustrate, if an antibody which binds the target substrate is used to sequester the protein on the matrix, then a detectable anti-geranylgeranyl antibody can be used to score for the presence of prenylated target substrate on the matrix.

Still a variety of other formats exist which are amenable to high through put analysis on microtitre plates or the like. The prenylation substrate can be immobilized throughout the reaction, such as by cross-linking to activated polymer, or sequestered to the well walls after the development of the prenylation reaction. In one illustrative embodiment, a Rho-like GTPase, e.g. a fungal Rho1, Rho2, Cdc42 or Rsr1/Bud1, is cross-linked to the polymeric support of the well, the prenylation system set up in that well, and after completion, the well washed and the amount of geranylgeranyl sidechains attached to the immobilized GTPase detected. In another illustrative embodiment, wells of a microtitre plate are coated with streptavidin and contacted with the developed prenylation system under conditions wherein a biotinylated substrate binds to and is sequestered in the wells. Unbound material is washed from the wells, and the level of prenylated target substrate is detected in each well. There are, as evidenced by this specification, a variety of techniques for detecting the level of prenylation of the immobilized substrate. For example, by the use of dansylated (described infra) or radiolabelled geranylgeranyl diphosphaste in the reaction mixture, addition of appropriate scintillant to the wells will permit detection of the label directly in the microtitre wells. Alternatively, the substrate can be released and detected, for example, by any of those means described above, e.g. by radiolabel, gel electrophoresis, etc. Reversibly bound substrate, such as the biotin-conjugated substrate set out above, is particularly amenable to the latter approach. In other embodiments, only the geranylgeranyl moiety is released for detection. For instance, the thioether linkage of the isoprenoid with the substrate peptide sequence can be cleaved by treatment with methyl iodide. The released geranylgeranyl products can be detected, e.g., by radioactivity, HPLC, or other convenient format.

Other geranylgeranyl derivatives include detectable labels which do not interfere greatly with the conjugation of that group to the target substrate. For example, in an illustrative embodiment, the assay format provides fluorescence assay which relies on a change in fluorescent activity of a group associated with a GGPTase substrate to assess test compounds against a fungal GGPTase. To illustrate, GGPTase-I activity can be measured by a modified version of the continuous fluorescence assay described for farnesyl transferases (Cassidy et al., (1985) *Methods Enzymol.* 250: 30–43; Pickett et al. (1995) *Analytical Biochem* 225:60–63; and Stirtan et al. (1995) *Arch Biochem Biophys* 321:182–190). In an illustrative embodiment, dansyl-Gly-Cys-Ile-Ile-Leu (d-GCIIL) and the geranylgeranyl diphosphate are added to assay buffer, along with the test agent or control. This mixture is preincubated at 30° C. for a few minutes before the reaction is initiated with the addition of GGPTase enzyme. The sample is vigorously mixed, and an aliquot of the reaction mixture immediately transferred to a prewarmed cuvette, and the fluorescence intensity measured for 5 minutes. Useful excitation and emission wavelengths are 340 and 486 nm, respectively, with a bandpass of 5.1 nm for both excitation and emission monochromators. Generally, fluorescence data are collected with a selected time increment, and the inhibitory activity of the test agent is determined by detecting a decrease in the initial velocity of the reaction relative to samples which lack a test agent.

In yet another embodiment, the geranylgeranyl transferase activity against a particular substrate can be detected in the subject assay by using a phosphocellulose paper absorption system (Roskoski et al. (1994) *Analytical Biochem* 222:275–280), or the like. To effect binding of a peptidyl substrate to phosphocellulose at low pH, several basic residues can be added, preferably to the amino-terminal side of the CAAX target sequence of the peptide, to produce a peptide with a minimal minimum charge of +2 or +3 at pH less than 2. This follows the strategy used for the phosphocellulose absorption assay for protein kinases. In an illustrative embodiment; the transfer of the [$H^3$] geranylgeranyl group from [$H^3$]-geranylgeranyl pyrophosphate to KLKCAIL or other acceptor peptides can be measured under conditions similar to the farnesyl transferase reactions described by Reiss et al. (Reiss et al., (1990) Cell 62: 81–88) In an illustrative embodiment, reaction mixtures can be generated to contain 50 mM Tris-HCL (pH 7.5), 50 $\mu$M $ZnCl_2$, 20 mM KCl, 1 mM dithiothreitol, 250 $\mu$M KLKCAIL, 0.4 $\mu$M [$H^3$] geranylgeranyl pyrophosphate, and 10–1000 $\mu$g/ml of purified fungal GGPTase protein. After incubation, e.g., for 30 minutes at 37° C., samples are applied to Whatman P81 phosphocellulose paper strips. After the liquid permeates the paper (a few seconds), the strips are washed in ethanol/phosphoric acid (prepared by mixing equal volumes of 95% ethanol and 75 mM phosphoric acid) to remove unbound isoprenoids. The samples are air dried, and radioactivity can be measured by liquid scintillation spectrometry. Background values are obtained by using reaction mixture with buffer in place of enzyme.

An added feature of this strategy is that it produces hydrophilic peptides that are more readily dissolved in water. Moreover, the procedure outlined above works equally well for protein substrates (most proteins bind to phosphocellulose at acidic pH), so should be useful where full length protein, e.g., Rho1 or Cdc42, are utilized as the GGPTase substrate.

Likewise, a variety of techniques are known in the art for accessing the activity of a glucan synthase and can be adapted for generating drug screening assays designed to detect inhibitors of a fungal glucan synthase complex which includes a Rho-like GTPase. As above, the cell-free glucan synthesis systems can be utilized in the subject assay, and include reconstituted protein mixtures and/or cell lysates/membrane preparations. Accordingly, in preferred embodiments, the glucan synthesis system is derived from purified protein preparations (preferably reconstituted in a lipid formulation) or membrane preparations derived from a reagent cells, e.g., a cell expressing a recombinant RhoI/Gsc1 complex. To illustrate, membrane extracts are prepared from selected cells, homogenized with glass beads, and unbroken cells and debris are removed by centrifugation. The supernatant fluids are centrifuged at high speed, and the resulting pellets are washed with buffer containing 0.05M potassium phosphate (pH 7.5), 0.5 mM DTT, and 1.0 mM PMSF. The washed pellet is resuspended in the same buffer containing 5% glycerol. This protein extract serves as the source for $\beta$(1-3)-glucan synthase in the enzymatic assays.

The $\beta$(1-3)-glucan synthase reactions can be performed similar to those described in the art (e.g., Cabib et al. (1 987) *Methods Enzymol.* 138:637–642) and the appended examples. Briefly, a reaction mixture is generated containing Tris (or other suitable buffer), dithiothretol, KF, glycerol, PMSF, UDP-glucose, guanosine 5'-($\gamma$-S)-triphosphate (GTP$\gamma$S), UDP-[$^3$H]glucose (Amersham) plus a sample of membrane protein extract. Optionally, $\alpha$-amylase can be added to reaction mixtures to eliminate the contribution of [3H]glucose incorporation into glycogen. The reactions are performed in the presence or absence of the test compound. Following incubation for a selected time, the [$^3$H]-glucose incorporated into trichloroacetic acid-insoluble material is collected onto glass fiber filters and measured using a liquid scintillation counter.

In still other embodiments of the subject assay, cell-free mixtures can be utilized to identify agents which inhibit the enzymatic activity of a fungal PKC/GTPase complex such as the PKC1/Rho1 complex. In an exemplary embodiment, the kinase activity of a PKC1/GTPase complex can assessed by such methods as described in Watanabe et al. (1994) *J Biol Chem* 269:16829–16836. For instance, phosphorylation reactions can be initiated by adding reaction cocktail (40 mM MOPS pH 7.5, 10 mM MgCl$_2$, 1 mM DTT, 50 $\mu$M [$\gamma$-$^{32}$P]ATP [6 $\mu$Ci/reaction], a substrate peptide and the PKC/GTPase complex, and incubated for the reaction to develop. Reactions can be terminated by adding 4× Laemmli's sample buffer, and the samples boiled and subjected to SDS/PAGE. After electrophoresis, gels are fixed in 12.5% trichloroacetic acid for 10 min, washed in 10% methanol/10% acetic acid to reduce background, dried, and subjected to autoradiography. Likewise, capillary zone electrophoresis (CZE) techniques can be used to separate and quantitate phosphorylated and unphosphorylated PKC substrate, especially peptide substrates, following such protocols as described by Dawson et al. (1994) Analytical Biochem 220: 340–345. Alternatively, reactions can be terminated by spotting onto P81 paper (Whatman). The paper washed three times with 75 mM H$_3$PO$_4$ and subjected to scintillation counting.

In another embodiment, the assay is started with the addition of enzyme and stopped after a set time by the addition of 25% trichloroacetic acid (TCA) and 1.0 mg/ml bovine serum albumin (BSA). The radioactive product is retained and washed on glass fiber filters that allow the unreacted $^{32}$P-ATP to pass through. As above, the amount of phosphorylation is determined by the radioactivity measured in a scintillation counter.

In still another embodiment, the kinase substrate can be separated by affinity tags. For instance, a biotinylated peptide substrate of the PKC/Rho1 complex can be provided in the kinase reaction mixture with [$\alpha^{32}$P]ATP, the $^{32}$P label incorporated into the peptide substrate can be detected by standard scintillation methods. An advantage to the biotin-capture system is that it tends to be more quantitative with respect to peptide sequestration relative to, for example, phosocellulose paper.

The artificial substrate used can be a synthetic peptide resembling the pseudosubstrate site of PKC1p. All known isoforms of PKC possess a sequence within their regulatory domains that is related to PKC phosphorylation sites, except for an alanine in place of the target serine or threonine of a substrate. These sequences, known as pseudosubstrate sites, have been proposed to act as autoinhibitors of PKC activity. Autoinhibition is thought to be relieved upon binding of activating cofactors to the regulatory domain. Peptides resembling pseudosubstrate sites, except with a serine or threonine in place of alanine, are known to be excellent substrates for PKC (House et al. (1987) *Science* 238:1726–1728). Therefore, one substrate that may be used to test fungal PKC1 complexes is the 15-amino acid peptide, GGLHRHGTIINRKEE, corresponding to residues 394–408 of PKC1p of *S. cerevisae* (the putative pseudosubstrate site), with a threonine in place of alanine at position 401.

Yet another technique which can be used to follow the kinase activity of a PKC/GTPase complex in the presence of a test agent involves a spectrophotometric assay relying on an ADP produced by the kinase-mediated phosphorylation reaction. Briefly, the formation of ADP in the kinase reaction can be coupled to the pyruvate kinase reaction to produce pyruvate which is, in turn, coupled to the lactate dehydrogenase reaction with the concomitant oxidation of DPNH to DPN+. The decrease in absorbance of 340 nm is used to determine the reaction rate. See, for example, Roskosi (1983) Methods Enzymol-i, 99:3–6

In addition to the prenylation and other enzymatic reaction-based assays, it is contemplated that any of the novel protein—protein interactions described herein could be directly be the target of a drug screening assay. For example, in one embodiment, the interaction between a GTPase and a catalytic subunit of a fungal glucan synthase, such as Gsc1/Fsk1 homologs, can be detected in the presence and the absence of a test compound. In another embodiment, the ability of a compound to inhibit the binding of a GTPase protein with a fungal PKC-like protein, such as PKC1, can be assessed in the subject assay. A variety of assay formats for detecting non-enzymatic protein interactions will suffice and, in light of the present invention, will be comprehended by a skilled artisan.

Complex formation between the GTPase polypeptide and a "target polypeptide" (e.g., a PKC polypeptide, a GS subunit, or a GGPTase) may be detected by a variety of techniques. Modulation of the formation of complexes can be quantitated using, for example, detectably labeled proteins such as radiolabeled, fluorescently labeled, or enzymatically labeled GTPase polypeptides, by immunoassay, by chromatographic detection, or by detecting the intrinsic activity of either the GTPase or target polypeptide.

Typically, it will be desirable to immobilize either the GTPase or the target polypeptide to facilitate separation of complexes from uncomplexed forms of one or both of the proteins, as well as to accommodate automation of the assay. Binding of a GTPase polypeptide to the target polypeptide, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/GTPase (GST/GTPase) fusion proteins can be adsorbed onto glutathione sepharose beads (Sigma Chemical, St. Louis, Mo.) or glutathione derivatized microtitre plates, which are then combined with a preparation of a target polypeptide, e.g. a labeled target polypeptide, along with the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and labeled target polypeptide retained on the matrix determined directly, or in the supernatant after the complexes are subsequently dissociated. Alternatively, the complexes can be dissociated from the matrix, separated by SDS-PAGE, and the level of target polypeptide found in the bead fraction quantitated from the gel using standard electrophoretic techniques.

Other techniques for immobilizing proteins on matrices are also available for use in the subject assay. For instance, either the GTPase or target polypeptide can be immobilized utilizing conjugation of biotin and streptavidin. For instance, biotinylated GTPase molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with GTPase, but which do not interfere with the interaction between the GTPase and target polypeptide, can be derivatized to the wells of the plate, and GTPase trapped in the wells by antibody conjugation. As above, preparations of a target polypeptide and a test compound are incubated in the GTPase-presenting wells of the plate, and the amount of complex trapped in the well can be quantitated. Other exemplary methods for detecting such complexes, in addition to those described above, include detection of a radiolabel or fluorescent label; immunodetection of complexes using antibodies reactive with the target polypeptide, or which are reactive with GTPase protein and compete with the target polypeptide; as well as enzyme-linked assays which rely on detecting an enzymatic activity associated with the target polypeptide, e.g., either intrinsic or extrinsic activity. In the instance of the latter, the enzyme can be chemically conjugated or provided as a fusion protein with the target polypeptide. To illustrate, the target polypeptide can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the target polypeptide and glutathione-S-transferase can be provided, and complex formation quantitated by detecting the GST activity using 1-chloro-2, 4-dinitrobenzene (Habig et al (1974) J Biol Chem 249:7130). Alternatively, using such substrates as described above, an intrinsic activity of the target polypeptide can be used to facilitate detection.

For processes which rely on immunodetection for quantitating one of the proteins trapped in the complex, antibodies against the target protein or GTPase protein, can be used. Alternatively, the protein to be detected in the complex can be "epitope tagged" in the form of a fusion protein which includes a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

Cell-based Assay Formats

In yet further embodiments, the drug screening assay is derived to include a whole cell expressing a fungal GTPase protein, along with one or more of a GGPTase, a PKC or a glucan synthase catalytic subunit. In preferred embodiments, the reagent cell is a non-pathogenic cell which has been engineered to express one or more of these proteins from recombinant genes cloned from a pathogenic fungus. For example, nonpathogenic fungal cells, such as *S. cerevisae*, can be derived to express a Rho-like GTPase from a fungal pathogen such as *Candida albicans*. Furthermore, the reagent cell can be manipulated, particularly if it is a yeast cell, such that the recombinant gene(s) complement a loss-of-function mutation to the homologous gene in the reagent cell. In an exemplary embodiment, a non-pathogenic yeast cell is engineered to express a Rho-like GTPase, e.g. Rho1, and at least one of the subunits of a GGPTase, e.g. RAM2 and/or Cdc43, derived from a fungal protein. One salient feature to such reagent cells is the ability of the practitioner to work with a non-pathogenic strain rather than the pathogen itself. Another advantage derives from the level of knowledge, and available strains, when working with such reagent cells as *S. cerevisae*.

The ability of a test agent to alter the activity of the GTPase protein can be detected by analysis of the cell or products produced by the cell. For example, agonists and antagonists of the GTPase biological activity can be detected by scoring for alterations in growth or viability of the cell. Other embodiments will permit inference of the level of GTPase activity based on, for example, detecting expression of a reporter, the induction of which is directly or indirectly dependent on the activity of a Rho-like GTPase. General techniques for detecting each are well known, and will vary with respect to the source of the particular reagent cell utilized in any given assay.

For example, quantification of proliferation of cells in the presence and absence of a candidate agent can be measured with a number of techniques well known in the art, including simple measurement of population growth curves. For instance, where the assay involves proliferation in a liquid medium, turbidimetric techniques (i.e. absorbence/transmittance of light of a given wavelength through the sample) can be utilized. For example, in the instance where the reagent cell is a yeast cell, measurement of absorbence of light at a wavelength between 540 and 600 nm can provide a conveniently fast measure of cell growth. Likewise, ability to form colonies in solid medium (e.g. agar) can be used to readily score for proliferation. In other embodiments, a GTPase substrate protein, such as a histone, can be provided as a fusion protein which permits the substrate to be isolated from cell lysates and the degree of acetylation detected. Each of these techniques are suitable for high through-put analysis necessary for rapid screening of large numbers of candidate agents.

Additionally, visual inspection of the morphology of the reagent cell can be used to determine whether the biological activity of the targeted GTPase protein has been affected by the added agent. To illustrate, the ability of an agent to create a lytic phenotype which is mediated in some way by a recombinant GTPase protein can be assessed by visual microscopy.

The nature of the effect of test agent on reagent cell can be assessed by measuring levels of expression of specific genes, e.g., by reverse transcription-PCR. Another method of scoring for effect on GTPase activity is by detecting cell-type specific marker expression through immunofluorescent staining. Many such markers are known in the art, and antibodies are readily available.

In yet another embodiment, in order to enhance detection of cell lysis, the target cell can be provided with a cytoplasmic reporter which is readily detectable, either because it has "leaked" outside the cell, or substrate has "leaked" into the cell, by perturbations in the cell wall. Preferred reporters are proteins which can be recombinantly expressed by the target cell, do not interfere with cell wall integrity, and which have an enzymatic activity for which chromogenic or fluorogenic substrates are available. In one example, a fungal cell can be constructed to recombinantly express the β-galactosidase gene from a construct (optionally) including an inducible promoter. At some time prior to contacting the cell with a test agent, expression of the reporter protein is induced. Agents which inhibit prenylation of a Rho-like GTPase in the cell, or the subsequent involvement of a Rho-like GTPase in cell wall integrity, can be detected by an increase in the reporter protein activity in the culture supernatant or from permeation of a substrate in the cell. This, for example, β-galactosidase activity can be scored using such calorimetric substrates as 5-bromo-4-chloro-3-indolyl-β-D-galactopyranoside or fluorescent substrates such as methylumbelliferyl-β-D-galactopyranoside. Permeation of the substrate into the cell, or leakage of the reporter into the culture media, is thus readily detectable.

In yet another embodiment, the alteration of expression of a reporter gene construct provided in the reagent cell provides a means of detecting the effect on GTPase activity. For example, reporter gene constructs derived using the transcriptional regulatory sequences, e.g. the promoters, for genes regulated by signal transduction processes downstream of the target Rho-like GTPase can be used to drive the expression of a detectable marker, such as a luciferase gene or the like. In an illustrative embodiment, the construct is derived using the promoter sequence from a gene expressed in PKC1-dependent heat shock response.

In still another embodiment, the membrane localization resulting from prenylation of the fungal GTPase can be exploited to generate the cell-based assay. For instance, the subject assay can be derived with a reagent cell having: (i) a reporter gene construct including a transcriptional regulatory element which can induce expression of the reporter upon interaction of the transcriptional regulatory protein portion of the above fusion protein. For example, a gal4 protein can be fused with a Rho1 polypeptide sequence which includes the CAAX prenylation target. Absent inhibitors of GGPTase activity in the reagent cell, prenylation of the fusion protein will result in partitioning of the fusion protein at the cell surface membrane. This provides a basal level of expression of the reporter gene construct. When contacted with an agent that inhibits prenylation of the fusion protein, partitioning is lost and, with the concomitant increase in nuclear concentration of the protein, expression from the reporter construct is increased.

In a preferred embodiment, the cell is engineered such that inhibition of the GGPTase activity does not result in cell lysis. For example, as described in Ohya et al. (1993) *Mol Cell Biol* 4:1017–1025, mutation of the C-terminus of Rho1 and cdc42 can provide proteins which are targets of farsenyl transferase rather than geranylgeranyl transferase. As Ohya et al. describe, such mutants can be used to render the GGPTase I activity dispensable. Accordingly, providing a reporter gene construct and an expression vector for the GGPTase substrate/transcription factor fusion protein in such cells as YOT35953 cells (Ohya et al., supra) generates a cell whose viability vis-à-vis the GGPTase activity is determined by the reporter construct, if at all, rather than by prenylation of an endogenous Rho-like GTPase by the GGPTase. Of course, the reporter gene product can be derived to have no effect on cell viability, providing for example another type of detectable marker (described, infra). Such cells can be engineered to express an exogenous GGPTase activity in place of an endogenous activity, or can rely on the endogenous activity. To further illustrate, the Cal1 mutant YOT35953 cell can be further manipulated to express a Cal1 homolog from, e.g., a fungal pathogen or a mammalian cell.

Alternatively, where inhibition of a GGPTase activity causes cell lysis and reporter gene expression, the leakage assay provided above can be utilized to detect expression of the reporter protein. For instance, the reporter gene can encode β-galactosidase, and inhibition of the GGPTases activity scored for by the presence of cells which take up substrate due to loss of cell wall integrity, and convert substrate due to the expression of the reporter gene.

In preferred embodiments, the reporter gene is a gene whose expression causes a phenotypic change which is screenable or selectable. If the change is selectable, the phenotypic change creates a difference in the growth or survival rate between cells which express the reporter gene and those which do not. If the change is screenable, the phenotype change creates a difference in some detectable characteristic of the cells, by which the cells which express the marker may be distinguished from those which do not.

The marker gene is coupled to GTPase-dependent activity, be it membrane association, or a downstream signaling pathway induced by a GTPase complex, so that expression of the marker gene is dependent on the activity of the GTPase. This coupling may be achieved by operably linking the marker gene to a promoter responsive to the therapeutically targeted event. The term "GTPase-responsive promoter" indicates a promoter which is regulated by some product or activity of the fungal GTPase. By this manner, the activity of a GGPTase can be detected by its effects on prenylation of GTPase and, accordingly, the downstream targets of the prenylated protein. Thus, transcriptional regulatory sequences responsive to signals generated by PKC/GTPase, GS/GTPase and/or other GTPase complexes, or to signals by other proteins in such complexes which are interupted by GTPase binding, can be used to detect function of Rho-like GTPases such as Rho1 and cdc42.

In the case of yeast, suitable positively selectable (beneficial) genes include the following: URA3, LYS2, HIS3, LEU2, TRP1, ADE1,2,3,4,5,7,8; ARGl, 3, 4, 5, 6, 8; HIS1, 4, 5, ILV1, 2, 5; THR1, 4; TRP2, 3, 4, 5, LEU1, 4, MET2,3,4,8,9,14,16,19; URA1,2,4,5,10; H0M3,6; ASP3; CHO1; ARO 2,7, CYS3, OLE1, IN01,2,4; PR01,3. Countless other genes are potential selective markers. The above are involved in well-characterized biosynthetic pathways. The imidazoleglycerol phosphate dehydratasc (IGP dehydratase) gene (HIS3) is preferred because it is both quite sensitive and can be selected over a broad range of expression levels. In the simplest case, the cell is auxotrophic for histidine (requires histidine for growth) in the absence of activation. Activation of the gene leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

The marker gene may also be a screenable gene. The screened characteristic may be a change in cell morphology, metabolism or other screenable features. Suitable markers include beta-galactosidase (Xgal, $C_{12}$FDG, Salmon-gal, Magenta-Gal (latter two from Biosynth Ag)), alkaline phosphatase, horseradish peroxidase, exo-glucanase (product of yeast exb1 gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). A preferred screenable marker gene is beta-galactosidase; yeast cells expressing the enzyme convert the colorless substrate Xgal into a blue pigment.

In another embodiment, the present invention provides a cell-based assay which is based on our finding that the Cal1-1 mutant (see Example 3), e.g., a mutant of the GGPTase subunit cdc43, results in supersensitivity to echinocandin. This observation suggests to us that GGPTase I inhibitors can enhance sensitivity to GS inhibitors, a phenotype which can be easily detected. In an exemplary embodiment, a fungal cell can be contacted with a test agent, and a GS inhibitor such as echinocandin B (other congeners of the echinocandin class of agents, such as cilofungin, certain pneumocandins, and WF11899A, B and C). The amount of cell lysis is determined and compared to the amount of cell lysis is the absence of the GS inhibitor. Synergism, e.g., a statistically significant increase in lysis of the GS inhibitor treated cell relative to the cell contacted only with the test agent, suggests that the test agent is likely to be a cytotoxic agent which targets prenylation of Rho-like GTPases, or the association of prenylated Rho-like GTPases with proteins critical to cell wall integrity. The fungal cell can be a wild-type or recombinant cell, e.g., such as an *S. cerevisiae* cell engineered to express Candida proteins.

It has also been observed in the art that mutations to Gsc1 (Fks1) confer hypersensitivity to the immunosuppressants FK506 and cyclosporin A (Douglas et al. (1994) *PNAS* 91:12907). The mechanism of action of such agents is understood to involve inhibition of expression of the Fks2 gene (Mazur et al. (1995) *Mol Cell Biol* 15:5671). Similar to the echinocandin-sensitivity assay embodiments provided above, another assay format provides a cell in which Fks2 activity is compromised. Synergism of the Fks2 impairment with a test compound can be used to identify inhibitors of, for example, the glucan synthase subunit Gsc1. For instance, FK506 or cyclosporin A can be used to impair Fks2 activity, as can mutations to calcincurin or to the Fks2 gene.

These observations also suggest that Cal1-1 cells or the like, e.g., impaired for certain GGPTase activities, are suitable for use in assay to detect GS inhibitors, as such cells are more sensitive to the effects of GS inhibitors. The benefits to enhanced sensitivity include speedier development of assay readouts, and the further prejudicing of the assay towards GS inhibitors rather than other targets which may not provide cytotoxicity. The latter can provide the ability to identify potential hits which may not themselves be potent GS inhibitors, but which can be manipulated, e.g., by combinatorial chemistry approaches, to provide potent and specific GS inhibitors.

In yet another embodiment, fungal proteins involved in the various interactions set out as targets above can be used to generate an interaction trap assay (see also, U.S. Pat. No. 5,283,317; Zervos et al. (1993) *Cell* 72:223–232; Madura et al. (1993) *J Biol Chem* 268:12046–12054; Bartel et al. (1993) *Biotechniques* 14:920–924; and Iwabuchi et al. (1993) *Oncogene* 8:1693–1696), for subsequently detecting agents which disrupt binding of the proteins to one and other.

In particular, the method makes use of chimeric genes which express hybrid proteins. To illustrate, a first hybrid gene comprises the coding sequence for a DNA-binding domain of a transcriptional activator fused in frame to the coding sequence for a "bait" protein, e.g., a fungal Rho1. The second hybrid protein encodes a transcriptional activation domain fused in frame to a gene encoding a "fish" protein which interacts with the Rho1 protein, e.g. a Gsc1 protein. If the bait and fish proteins are able to interact, e.g., form a Rho1/Gsc1 complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the bait and fish proteins.

In accordance with the present invention, the method includes providing a host cell, preferably a yeast cell, most preferably *Saccharomyces cerevisiae* or *Schizosaccharomyces pombe*. The host cell contains a reporter gene having a binding site for the DNA-binding domain of a transcriptional activator, such that the reporter gene expresses a detectable gene product when the gene is transcriptionally activated. Such activation occurs when the activation domain of the transcriptional activator is brought into sufficient proximity to the DNA-binding domain of a transcriptional activator bound to the regulatory element of the reporter gene. The first chimeric gene may be present in a chromosome of the host cell, or as part of an expression vector.

A first chimeric gene is provided which is capable of being expressed in the host cell. The gene encodes a chimeric protein which comprises (i) a DNA-binding domain that recognizes the responsive element on the reporter gene in the host cell, and (ii) bait protein, such as Rho1.

A second chimeric gene is provided which is capable of being expressed in the host cell. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid. The second chimeric gene includes a DNA sequence that encodes a second hybrid protein comprising a transcriptional activation domain fused to a fish protein, or a fragment thereof, which is to be tested for interaction with the bait protein. The fish protein can be a subunit of a GGPTase which interacts with Rho1, or a subunit of a glucan synthase which interacts with Rho1, or Pkc1.

Preferably, the DNA-binding domain of the first hybrid protein and the transcriptional activation domain of the second hybrid protein are derived from transcriptional activators having separable DNA-binding and transcriptional activation domains. For instance, these separate DNA-binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally -inert DNA-binding domains may be used in the subject constructs; such as domains of ACE1, λcI, lac repressor, jun or fos. In another embodiment, the DNA-binding domain and the transcriptional activation domain may be from different proteins. The use of a LexA DNA binding domain provides certain advantages. For example, in yeast, the LexA moiety contains no activation function and has no known effect on transcription of yeast genes. In addition, use of LexA allows control over the sensitivity of the assay to the level of interaction (see, for example, the Brent et al. PCT publication WO94/10300).

In preferred embodiments, any enzymatic activity associated with the bait or fish proteins is inactivated, e.g., dominant negative mutants of Rho1 and the like can be used. Where the interacting proteins are of the enzyme-substrate relationship, mutation of one or more catalytic residues of the enzyme can provide a mutant protein which retains the ability to bind the substrate but not catalytically convert it to product.

Continuing with the illustrated example, the Rho1/Gsc1-mediated interaction, if any, between the first second fusion proteins in the host cell, therefore, causes the activation domain to activate transcription of the reporter gene. The method is carried out by introducing the first chimeric gene and the second chimeric gene into the host cell, and subjecting that cell to conditions under which the first hybrid protein and the second hybrid protein are expressed in sufficient quantity for the reporter gene to be activated. The formation of a Rho1/Gsc1 complex results in a detectable signal produced by the expression of the reporter gene. Accordingly, the formation of a complex in the presence of a test compound to the level of Rho1/GSC1 complex in the absence of the test compound can be evaluated by detecting the level of expression of the reporter gene in each case.

In an illustrative embodiment, *Saccharomyces cerevisiae* YPB2 cells are transformed simultaneously with a plasmid encoding a GAL4db-Rho1 fusion and with a plasmid encoding the GAL4ad domain fused to a fungal Gsc1 gene. Moreover, the strain is transformed such that the GAL4-responsive promoter drives expression of a phenotypic marker. For example, the ability to grow in the absence of histidine can depend on the expression of the LacZ gene. When the LacZ gene is placed under the control of a GAL4-responsive promoter, the yeast cell will turn blue in the presence of β-gal if a functional GAL4 activator has been reconstituted through the interaction of Rho1 and Gsc1. Thus, a convenient readout method is provided. Other reporter constructs will be apparent, and include, for example, reporter genes which produce such detectable signals as selected from the group consisting of an enzymatic signal, a fluorescent signal, a phosphorescent signal and drug resistance.

A similar method modifies the interaction trap system by providing a "relay gene" which is regulated by the transcriptional complex formed by the interacting bait and fish proteins. The gene product of the relay gene, in turn, regulates expression of a reporter gene, the expression of the latter being what is scored in the modified ITS assay. Fundamentally, the relay gene can be seen as a signal inverter.

As set out above, in the standard ITS, interaction of the fish and bait fusion proteins results in expression of a reporter gene. However, where inhibitors of the interaction are sought, a positive readout from the reporter gene nevertheless requires detecting inhibition (or lack of expression) of the reporter gene.

In the inverted ITS system, the fish and bait proteins positively regulate expression of the relay gene. The relay gene product is in turn a repressor of expression of the reporter gene. Inhibition of expression of the relay gene product by inhibiting the interaction of the fish and bait proteins results in concomitant relief of the inhibition of the reporter gene, e.g., the reporter gene is expressed. For example, the relay gene can be the repressor gene under control of a promoter sensitive to the Rho1/Gsc1 complex described above. The reporter gene can accordingly be a positive signal, such as providing for growth (e.g., drug selection or auxotrophic relief), and is under the control of a promoter which is constitutively active, but can be suppressed by the repressor protein. In the absence of an agent which inhibits the interaction of the fish and bait protein, the repressor protein is expressed. In turn, that protein represses expression of the reporter gene. However, an agent which disrupts binding of the Rho1 and Gsc1 proteins results in a decrease in repressor expression, and consequently an increase in expression of the reporter gene as repression is relieved. Hence, the signal is inverted.

Returning to the teachings of Ohya et al. (1993) *Mol Cell Biol* 4:1017–1025, it is noted that there are only two essential targets of GGPTase in *S. cerevisae*, the Rho-like GTPases Rho1 and cdc42. With such observations in mind, yet another embodiment of the subject assay utilizes a side-by-side comparison of the effect of a test agent on (i) a cell which prenylates a Rho-like GTPase by adding geranylgeranyl moieties, and (ii) a cell which prenylates an equivalent Rho-like GTPase by adding farnesyl moieties. In particular, the assay makes use of the ability to suppress GGPTase I defects in yeast by altering the C-terminal tail of Rho1 and cdc42 to become substrate targets of farnesyl transferase (see Ohya et al., supra). According to the present embodiment, the assay is arranged by providing a yeast cell in which the target Rho-like GTPases is prenylated by a GGPTase activity of the cell. Both the GGPTase and GTPase can be endogenous to the "test" cell, or one or both can be recombinantly expressed in the cell. The level of prenylation of the GTPase is detected, e.g., cell lysis or other means described above. The ability of the test compound to inhibit the addition of geranylgeranyl groups to the GTPase in the first cell is compared against the ability of test compound to inhibit the farnesylation of the GTPase in a control cell. The "control" cell is preferably identical to the test cell, with the exception that the targeted GTPase(s) are mutated at their CAAX sequence to become substrates for FPTases rather than GGPTases. Agents which inhibit prenylation in the test cell but not the control cell are selected as potential antifungal agents. Such differential screens can be exquisitely sensitive to inhibitors of GGPTase I prenylation of Rho-like GTPases. In a preferred embodiment, the test cell is derived from the *S. cerivisae* cell YOT35953 (Ohya et al., supra) or the like which is defective in GGPTase subunit cdc43. The cell is then engineered with a cdc43 subunit from a fungal pathogen such as *Candida albicans* to generate the test cell, and additionally with the mutated Rho-like GTPases to generate the control cell.

Differential Screening Formats

In a preferred embodiment, assays can be used to identify compounds that have therapeutic indexes more favorable than such antifungal as, for example, papulacandins or echinocandins or the like. For instance, antifungal agents can be identified by the present assays which inhibit proliferation of yeast cells or other lower eukaryotes, but which have a substantially reduced effect on mammalian cells, thereby improving therapeutic index of the drug as an anti-mycotic agent.

In one embodiment, the identification of such compounds is made possible by the use of differential screening assays which detect and compare the ability of the test compound to inhibit an activity associated with a fungal GTPase, relative to its ability to inhibit an analogous activity of a human GTPase. To illustrate, the assay can be designed for side-by-side comparison of the effect of a test compound on the prenylation activity or protein interactions of fungal and human GGPTase and GTPase proteins. Given the apparent diversity of GGPTase proteins, it is probable that the fungal and human GGPTases differ both in substrate specificity and mechanistic action which can be exploited in the subject assay. Running the fungal and human prenylation systems side-by-side permits the detection of agents which have a greater inhibitory effect (e.g. statistically significant) on the prenylation reaction mediated by the fungal GGPTase than the human enzyme.

Accordingly, differential screening assays can be used to exploit the difference in protein interactions and/or catalytic mechanism of mammalian and fungal GGPTases in order to identify agents which display a statistically significant increase in specificity for inhibiting the fungal prenylation reaction relative to the mammalian prenylation reaction. Thus, lead compounds which act specifically on the prenylation reaction in pathogens, such as fungus involved in mycotic infections, can be developed. By way of illustration, the present assays can be used to screen for agents which may ultimately be useful for inhibiting the growth of at least one fungus implicated in such mycosis as candidiasis, aspergillosis, mucormycosis, blastomycosis, geotrichosis, cryptococcosis, chromoblastomycosis, coccidioidomycosis, conidiosporosis, histoplasmosis, maduromycosis, rhinosporidosis, nocaidiosis, para-actinomycosis, penicilliosis, monoliasis, or sporotrichosis. For example, if the mycotic infection to which treatment is desired is candidiasis, the present assay can comprise comparing the relative effectiveness of a test compound on inhibiting the prenylation of a mammalian GTPase protein with its effectiveness towards inhibiting the prenylation of a GTPase from a yeast selected from the group consisting of *Candida albicans, Candida stellatoidea, Candida tropicalis, Candida parapsilosis, Candida krusei, Candida pseudotropicalis, Candida quillermondii,* or *Candida rugosa.* Likewise, the present assay can be used to identify anti-fungal agents which may have therapeutic value in the treatment of aspergillosis by selectively targeting, relative to human cells, GTPase homologs from yeast such as *Aspergillus fumigatus, Aspergillus flavus, Aspergillus niger, Aspergillus nidulans,* or *Aspergillus terreus.* Where the mycotic infection is mucormycosis, the GTPase system to be screened can be derived from yeast such as *Rhizopus arrhizus, Rhizopus oryzae, Absidia corymbifera, Absidia ramosa,* or *Mucor pusillus.* Sources of other assay reagents for includes the pathogen *Pneumocystis carinii.*

Thus, it is also deemed to be within the scope of this invention that the recombinant GTPase cells of the present assay can be generated so as to comprise heterologous GTPase proteins from metazoan sources such as humans (i.e. cross-species expression). For example, GTPase proteins from humans can be expressed in the reagent cells under conditions wherein the heterologous protein is able to rescue loss-of-function mutations in the host cell. For example, the reagent cell can be a yeast cell in which a human GTPase protein (e.g. exogenously expressed) is to be a counter-screen for identifying agents which selectively inhibit yeast GTPase activities. To illustrate, the YOC706 strain, described by Qadota et al (1994) *Genetics* 91:9317–9321, lacks a functional endogenous Rho1 gene, and can be transfected with an expression plasmid including a human GTPase gene such as RHoA in order to complement the Rho1 loss-of-function. For example, the coding sequence for RHoA can be cloned into a pRS integrative plasmid containing a selectable marker (Sikorski et al. (1989) Genetics 122:19–27), and resulting construct used to transform the YOC706 strain. The resulting cells should produce a human RHoA protein which is capable of performing at least some of the functions of the yeast Rho1 protein. The GTPase transformed yeast cells can be easier to manipulate than mammalian cells, and can also provide access to certain assay formats, such as turbidity detection, which may not be obtainable with mammalian cells.

Reagents

If yeast cells are used, the yeast may be of any species which are cultivable and, preferably, in which an exogenous Rho1-like protein can be made to engage the appropriate prenylation enzyme and/or participate in protein complexes such as with glucan synthesase subunits or PKC homologs of the host cell. Suitable species include *Kluyverei lactis, Schizosaccharomyces pombe,* and *Ustilaqo maydis; Saccharomyces cerevisiae* is preferred. Other yeast which can be used in practicing the present invention. The term "yeast", as used herein, includes not only yeast in a strictly taxonomic sense, i.e., unicellular organisms, but also yeast-like multicellular fungi or filamentous fungi.

The choice of appropriate host cell can be influenced by the choice of detection signal. For instance, reporter constructs, as described below, can provide a selectable or screenable trait upon transcriptional activation (or inactivation) in response to a signal provided by the GTPase target. Suitable genes and promoters can be dependent on the reagent cell. Likewise, ease of complementation, genetic manipulation, etc., may also affect the choice of reagent cell.

With respect to sources for constituting recombinant proteins of the subject assays, various GGPTases, GTPases, glucan synthase subunits, and PKC homologs have been identified from a variety of fungal species, and in a significant number of instances, have been cloned so that recombinant sources exist.

For example, identification of enzymes involved in the prenylation pathway from different sources have facilitated the cloning of corresponding genes. For instance, genes GGPTase enzymes, PKC homologs and GTPase homologs have been cloned from various fungal organisms, and are generally described in the literature and available on GenBank or other such databases. Complementation of defects in yeast cells such as *S. cereviae* also constitute a standard protocol for isolating genes encoding fungal and mammalian homologs (as appropriate) of such target proteins as GGPTase subunits, Rho-like GTPases, PKC homologs and glucan synthase subunits.

The proteins provided in the subject assay can be derived by purification from a cell in which it is endogenously expressed, or from a recombinant source of the protein. In each instance where a recombinant source of a protein is used in the subject assay, the manipulation of the gene encoding the protein and the subsequent expression of the protein can be carried out by standard molecular biological techniques. Ligating the polynucleotide sequence encoding the recombinant protein into a gene construct, such as an expression vector, and transforming or transfecting into host cells, either eukaryotic (yeast, avian, insect or mammalian) or prokaryotic (bacterial cells), are standard procedures used in producing other well-known proteins, including the *S. cerevisae* proteins PKC1, GGPTase, RhoI and the like. Similar procedures, or obvious modifications thereof, can be employed to prepare and purify recombinant proteins of the prenylation system from other sources.

The recombinant protein can be produced by ligating the cloned gene, or a portion thereof, into a vector suitable for expression in either prokaryotic cells, eukaryotic cells, or both. Expression vehicles for production of recombinant proteins include plasmids and other vectors. For instance, suitable vectors for the expression of these proteins include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

In general, it will be desirable that the gene construct be capable of replication in the host cell. It may be a DNA which is integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (*Cloning Vectors: A Laboratory Manual*, Elsevier, New York, 1985). Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

A number of vectors exist for the expression of recombinant proteins in yeast. For instance, YEP24, YIP5, YEP51, YEP52, pYES2, and YRP17, as well as the pRS vectors, e.g., pRS303, pRS304, pRS305, pRS306, etc., are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

Moreover, when yeast are used as the reagent cell, it will be understood that the expression of a gene in a yeast cell requires a promoter which is functional in yeast. Suitable promoters include the promoters for gall, metallothionein, 3-phosphoglycerate kinase (Hitzeman et al., *J. Biol. Chem.* 255, 2073 (1980) or other glycolytic enzymes (Hess el al., *J. Adv. Enzyme Req.* 7, 149 (1968); and Holland et al. *Biochemistry* 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFal and MFα1 are of particular interest.

In some instances, it may be desirable to derive the host cell using insect cells. In such embodiments, recombinant polypeptides can be expressed by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Furthermore, the recombinant protein can be encoded by a fusion gene created to have additional sequences coding for a polypeptide portion of a fusion protein which would facilitate its purification. For instance, a fusion gene coding for a purification leader sequence comprising a poly-(His)/ enterokinase cleavage site sequence can be engineered at the a terminus of the protein, thereby enabling purification of the expressed fusion protein by affinity chromatography using a $Ni^{2+}$ metal resin. The purification leader sequence can then be subsequently removed by treatment with enterokinase (e.g., see Hochuli et al. 1987 *J Chromatography* 411:177; and Janknecht et al. *PNAS* 88:8972).

Exemplary construction of the expression plasmid for recombinant GGPTase-I.

Polymerase chain reaction (PCR) can be carried out to isolate the CDC43 coding sequence from *S cerevisiae*. Using a sense strand primer (5'-CCATCGATCAT ATGTGTCAAGCTAGGAAT-3') can introduce a unique ClaI restriction site upstream of the CDC43 start codon and an NdeI site that overlaps the ATG initiation codon. An antisense strand PCR primer (5'-GCGGGTACCCTGCAGTCAAAAACAGCACCTTTT-3') introduces unique PstI and KpnI restriction sites downstream of the CDC43 stop codon. The PCR product is ligated into a convenient vector, such as bluescript II SK-(+) using ClaI and KpnI. An XbaI-ClaI fragment containing RAM2

(Mayer et aL, (1993) *Gene* 132:41–47) can be cloned into the CDC43 containing vector, upstream of the CDC43 sequence, to produce a bicistronic construct. The RAM2 and CDC43 orfs are then coupled by deletion mutagenesis with the antisense strand primer (5'-GGTAGC TTGAVACATCAAAACTCCTCCTGCAGATTTATTTTG-3'), which overlaps the RAM2 translation termination codon with the CDC43 initiation codon. The RAM2-CDC43 cassette can then be cloned into an appropriate expression vector and used to transform *E coli*.

Recombinant GGPTase-I can be purified from the resulting cultures as described for recombinant yeast FPTase (Mayer et al., supra), with minor modifications (Stirtan et al. (1995) *Arch Biochem Biophys* 321:182–190). Wet cell paste is resuspended in 16 ml of lysis buffer (50 mM Tris-HCl, pH 7.0, 10 mM BME, 10 mM $MgCl_2$, 50 μM $ZnCl_2$, 1 mM PMSF) and disrupted by sonication. The cell-free homogenate is clarified by centrifugation and chromatographed on DE52 ion-exchange resin (1.5×14 cm) at 4° C., preequilibrated with low-salt buffer (50 mM Tris-Hcl, pH 7.0, 10 mM $MgCl_2$, 50 μM $ZnCl_2$, 10 mM BME). Protein is eluted with a stepwise gradient of 0 to 800 mM NaCl in low-salt buffer. Recombinant PGGPTase-I is expected to elute at 200 mM NaCl. The DE52-purified material is dialyzed at 4° C. against low-salt buffer, diluted to ~1 mg/ml with the same buffer, and loaded onto an anti-α-tubulin immunoaffinity column (Mayer et aL, supra) preequilibrated with binding buffer (20 mM Tris-HCl, pH 7.5, 1 mM $MgCl_2$, 10 μM $ZnCl_2$, 5 mM BME, 50 mM NaCl). The column is washed with binding buffer (~25 ml) and then eluted with binding buffer containing 5 mM Asp-Phe. Fractions containing GGPTase-I activity are combined. Recombinant GGPTase-I has been demonstrated to be stable for several months at −80° C. and for several days at 0° C.

Preparation of dansyl-Gly-Cys-Ile-Ile-Leu.

Dansyl-Gly-Cys-Ile-Ile-Leu is prepared essentially as described previously for dansyl-Gly-Cys-Val-alle-Ala (Cassidy et al., (1985) *Methods Enzymol.* 250: 30–43), the farnesylated substrate corresponding to Cys-Val-Ile-Ala. Dansyl-Gly-Cys-Ile-Ile-Leu can be purified by preparative HPLC on a Vydac protein and peptide C18 reversed-phase column (22 mm×25 cm) by elution with a gradient of 85–92% $CH_3CN/0.1\%$ TFA in $H_2O/0.1\%$ TFA over 20 min, followed by a gradient of 92–100% $CH_3CN/0.1\%$ TFA over 5 min, and finally with 100% $CH_3CN/0.1\%$ TFA for 10 min. Organic materials are removed by rotary evaporation, and the resulting aqueous suspension is lyophilized to afford dansyl-Gly-Cys-Ile-Ile-Leu Pharmaceutical Preparations of Identified Agents After identifying certain test compounds as potential antifungal agents, the practioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

The subject compounds selected in the subject, or a pharmaceutically acceptable salt thereof, may accordingly be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In preferred embodiment, the compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

EXEMPLIFICATION

The invention, now being generally described, will be more readily understood by reference to the following examples, which are included merely for purposes of illustration of certain aspects and embodiments of the present invention and are not intended to limit the invention.

Example 1

Activation of Yeast Protein Kinase C by Rho1 GTPase

The abbreviations used in Example 1 are: PKC, protein kinase C; MAPK, mitogen-activated protein kinase; MEK, MAPK-activating kinase; MEKK, MEK-activating kinase; DAG, diacylglycerol; SRF, serum response factor; JNK, Jun $NH_2$-terminal kinase (also known as SAPK, stress-activated protein kinase); PCR, polymerase chain reaction; HA, influenza hemagglutinin; PAGE, polyacrylamide gel electrophoresis; GST, glutathione-S-transferase; PS, phosphatidylserine; PMA, phorbol myristate acetate; GS, 1,3-β-glucan synthase; MBP, myelin basic protein.

A. Overview

We have investigated the role of the essential Rho1 GTPase in cell integrity signaling in budding yeast. Conditional rho1 mutants display a cell lysis defect that is similar to that of mutants in the cell integrity signaling pathway mediated by protein kinase C (PKC1), which is suppressed by overexpression of PKC1. rho1 mutants are also impaired in pathway activation in response to growth at elevated temperature. PKC1 co-immuneprecipitates with Rho1 in yeast extracts, and recombinant Rho1 associates with PKC1 in vitro in a GTP-dependent manner. Recombinant Rho1 confers upon PKC1 the ability to be stimulated by phosphatidylserine (PS), indicating that Rho1 controls signal transmission through PKC1.

The PKC1 gene of the budding yeast *Saccharomyces cerevisiae* encodes a homolog of mammalian protein kinase C (PKC) (ref. 1) that regulates a MAP kinase (MAPK)-activation cascade comprised of a MEKK (Bck1), a redundant pair of MEKs (Mkk1/2), and a MAPK (Mpk1) (2, 3). Mutants in this signaling cascade, called the cell integrity pathway, undergo cell lysis resulting from a deficiency in cell wall construction that is exacerbated by growth at elevated temperatures. We have reported that thermal stress activates the cell integrity pathway, and proposed that weakness in the cell wall that develops during growth at high temperature induces the signal for pathway activation (4).

PKC1 most closely resembles the conventional isoforms of mammalian PKC, which require phospholipids, $Ca^{2+}$, and diacylglycerol (DAG) as cofactors to stimulate their catalytic activity (1). However, in vitro studies of this yeast protein kinase have failed to demonstrate stimulation by cofactors, despite the finding that mutations in PKC1 predicted to relieve cofactor dependence have an activating effect on the enzyme (5, 6). This suggested that one or more components required for cofactor-dependent stimulation of PKC1 was missing from in vitro reconstitution experiments.

Members of the Rho family of small GTPases (RhoA, Cdc42, and Rac) regulate various aspects of actin cytoskeleton organization and activation of the SRF transcription factor in mammalian cells (7–10). Cdc42 and Rac, but not RhoA, stimulate the signaling pathway that contains the JNK/SAPK (Jun $NH_2$-terminal kinase or stress-activated protein kinase) MAPK homolog in mammalian cells (11–13). Downstream effectors of RhoA have not been identified (14, 15). The yeast RHO1 gene encodes a homolog of mammalian RhoA that resides at sites of cell growth (16) and whose function is essential for viability (17). A rho1Δ A mutant is partially suppressed by expression of human RhoA, but a residual cell lysis defect is apparent at high temperature (18), suggesting that RHO1 may function within the cell integrity pathway. Additionally, an activated allele of PKC1 was isolated recently as a dominant mutational suppressor of this defect (19), further supporting the notion that these signaling molecules act through a common pathway. In this communication, we demonstrate that Rho1 associates with PKC1 in a GTP-dependent manner, and confers upon this protein kinase the ability to respond to phosphatidylserine as an activating cofactor.

B. Experimental Procedures

Yeast strains and mutant construction—All strains used in this study were derived from YPH500 (See reference of Example 3). Error-prone PCR (21) was used to introduce random mutations into the RHO1 sequence. The PCR-amplified RHO1 fragment was inserted into the EcoRI/BglII gap of pYO701, and introduced into yeast strain YOC706, which harbors a rho1Δ and a plasmid expressing RHO1 under the control of the GAL1 promoter (18). We examined 4000 transformants for growth on YPD (yeast extract/peptone/dextrose) plates at 23° .C and 37° C., and identified 41 rho1$^{ts}$ mutations. Among these, 11 rho1 alleles (designated rho1-1–rho1-11) contained single or double base changes. All of these alleles were reconstructed by site-directed mutagenesis, and integrated at the ADE3 locus (See reference of Example 3) of diploid strain YOC701 (RHO1/rho1Δ::HIS3). Haploid strains used in this study (YOC764 [RHO1], YOC729 [rho1-3], and YOC755 [rho1-5]) were derived from YOC701 integrants by standard genetic techniques. A single copy plasmid (pYO904) that carries HA-tagged RHO1 was constructed in vector pRS314, as described previously (16), and introduced into yeast strain YOC701. A segregant bearing rho1Δ::HIS3 and pYO904, and a wild-type (RHO1) segregant lacking the plasmid were used for coimmunoprecipitation experiments.

Antibodies, extracts, immunoprecipitation, protein kinase assays and immunodetection—Anti-HA antibodies (12CA5; BAbCo, Inc.) were used for immunoprecipitation and immunodetection of $^{HA}$Rho1, Mpk1$^{HA}$, and PKC1$^{HA}$. Polyvalent PKC1 antibodies (used for immunodetection of PKC1) were raised by Cocalico Biologicals (Reamstown, Pa.) in New Zealand white rabbits against a TrpE::PKC1 fusion protein that contains amino acids 470–664 of PKC1. This antiserum was used (at 1:3000 dilution) for immunodetection of PKC 1. Secondary antibodies used were horseradish peroxidase-conjugated donkey anti-rabbit (Amersham; at 1:10,000 dilution).

Yeast extract preparation, immunoprecipitation, immunodetection and protein kinase assays of Mpk1$^{HA}$ were conducted as described previously (4). Preparation of cell extracts and immunoprecipitations for experiments with HARho were carried out as in (4) with some modifications. Lysis buffer without p-nitrophenyl phosphate and with 1% NP-40 was used. The extract (700 μg protein) was precleared by incubation with 20 μl of a 50% suspension of protein A-sepharose for 1 h prior to immunoprecipitation to eliminate non-specific binding of proteins to immunecomplexes. Beads were boiled in SDS-PAGE sample buffer, and samples were applied to 7.5% (for PKC1 blots) or 15% (for $^{HA}$Rho1 blots) SDS-PAGE gels. For PKC1 kinase assays, all as described previously (5), except for the addition of recombinant GTPases (see below). A synthetic peptide corresponding to the sequence surrounding Ser939 of Bck1, a phosphorylation site for PKC1, was used as substrate in PKC1kinase assays (5).

Recombinant Rho1 and Cdc42. Recombinant GST-Rho1 and GST-Cdc42 were expressed and purified from baculovirus-infected insect (Sf9) cells, as described (23). For in vitro association with PKC1$^{HA}$, GST-Rho1 was not eluted from the glutathione agarose beads used for purification. GST-Rho1-bound beads were incubated with cell extract in immunoprecipitation buffer (4) for 5 h at 4° C., followed by 3 washes with this buffer. For use in PKC1$^{HA}$ protein kinase assays, GST-Rho1 and GST-Cdc42 were eluted from the beads with reduced glutathione. Purified GST-Rho1 displayed no protein kinase activity against the Bck1 peptide in the absence of PKC1 (not shown).

C. Results And Discussion

Figure 1A:
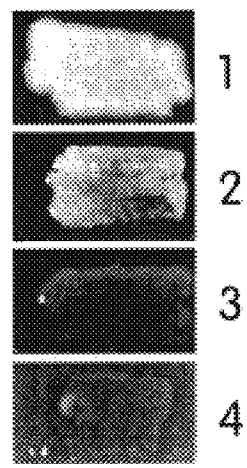
FIGS. 1A–B Overexpression of PKC1 suppresses the cell lysis defect of a $rho1^{ts}$ mutant.
Figure 1B:
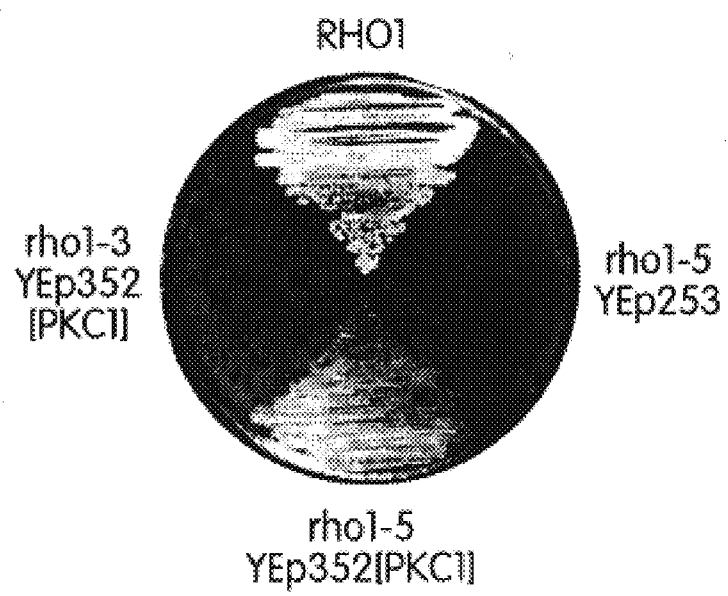

To examine the role of RHO1 in the cell integrity signaling pathway, we isolated a set of 11 temperature-sensitive rho1 alleles by in vitro random mutagenesis. Some of these mutants displayed cell lysis defects at the restrictive temperature (eg. rho1-5), but others did not (eg. rho1-3; FIG. 1A). Additionally, overexpression of PKC1 suppressed exclusively rho1-5 (FIG. 1B). Because of this allele-specific behavior, we chose rho1-3 and rho1-5 for further study.

Figure 2:
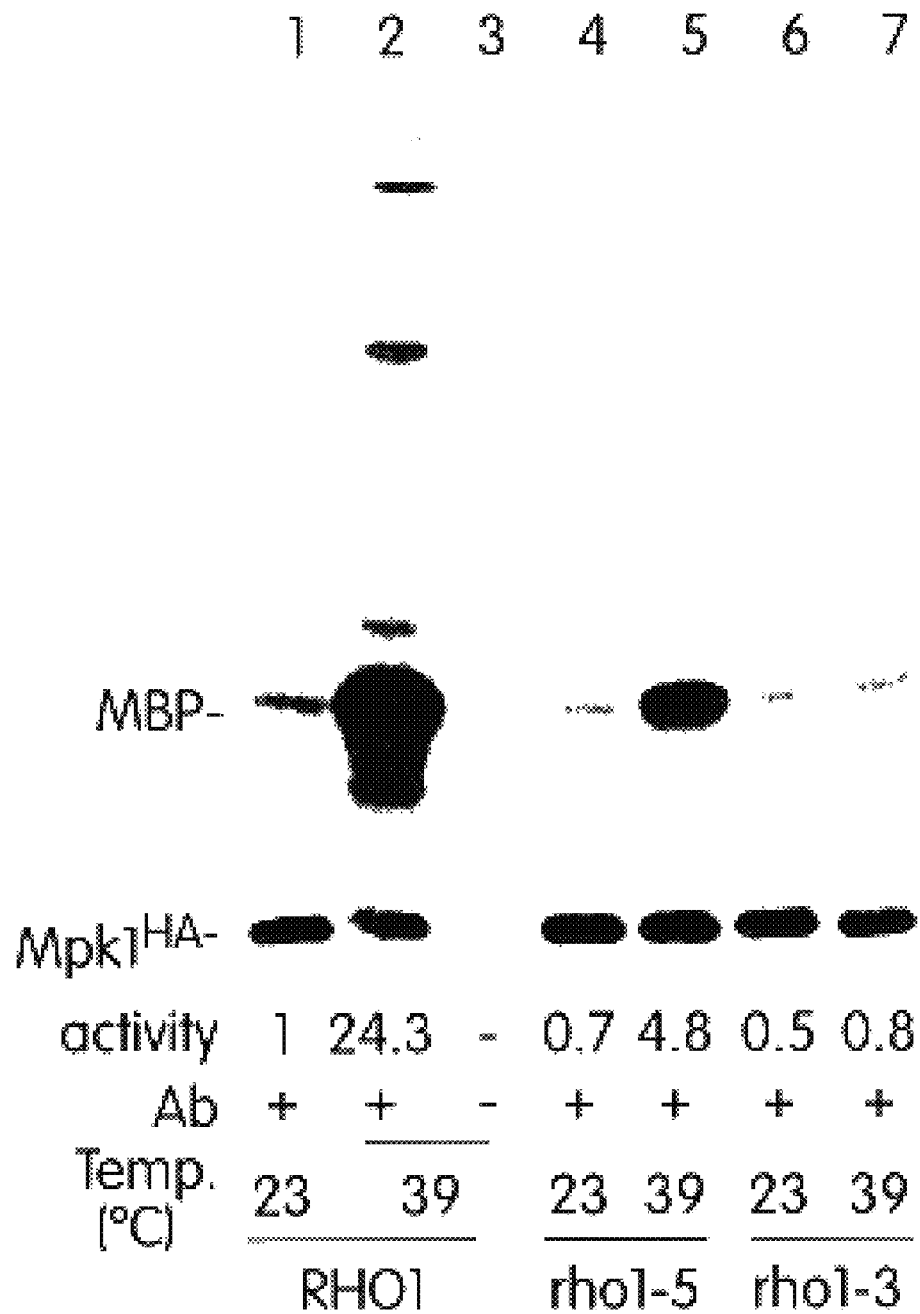
FIG. 2. RHO1 is required for Mpk1 activation in response to heat shock. (Top panel) Phosphorylation of myelin basic protein (MBP) by $Mpk1^{HA}$ immunoprecipitated from extracts of cells shifted from growth at 23° C. to 39° C. for 30 min. This treatment did not affect the viability of the mutant strains (data not shown). Mpk1 activity in rho1-5 (lanes 4 and 5) and rho1-3 (lanes 6 and 7) relative to wild-type (RHO 1; lane 1-3) maintained at 23° C. (lane 1) is indicated. (Bottom panel) Immunoblot of immunoprecipitated $Mpk1^{HA}$.

The Mpk1 MAPK is activated via PKC1 in response to brief heat shock treatment (4). To determine if RHO1 is required for cell integrity pathway signaling, we tested the ability of rho1$^{ts}$ mutants to activate Mpk1 upon heat shock. Mpk1, tagged at its COOH-terminus with the influenza hemagglutinin (HA) epitope (Mpk1$^{HA}$), was immunoprecipitated from extracts of heat shock-treated cells, and assayed for protein kinase activity in vitro using myelin basic protein (MBP) as substrate. Heat shock-induced activation of Mpk1 was completely blocked in the rho1-3 mutant (FIG. 2), indicating that RHO1 function is essential for Mpk1 activation. The rho1-5 mutant allowed some Mpk1 activation, suggesting that this allele retains some function at restrictive temperature. Residual function of the rho1-5 allele at high temperature might also explain the allele-specific suppression of this mutant by PKC1 overexpression if Rho1 function is required for PKC1 activation.

Figure 3A:
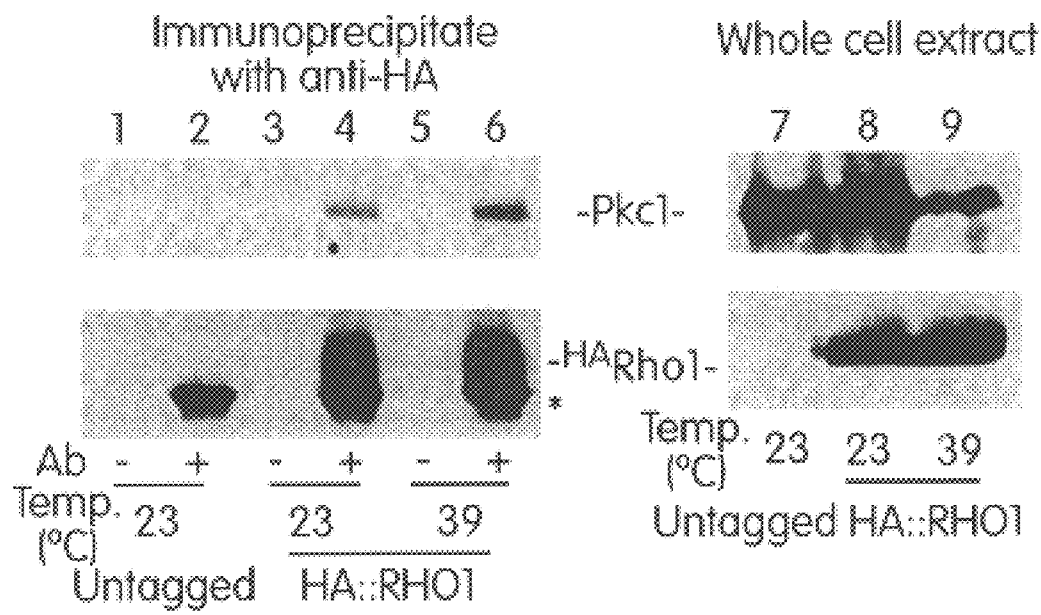
FIG. 3A–B PKC1 associates with Rho1 in vivo and in vitro.

The yeast Cdc42 GTPase interacts with and stimulates the Ste20 protein kinase, which regulates the MAPK-activation cascade of the yeast pheromone response pathway (24, 25). Additionally, both recombinant human Cdc42 and Rac stimulate a mammalian protein kinase that is closely related to Ste20 (PAK65) (26, 27). Because Ste20 and PKC1 function at analogous positions in their respective MAPK signaling pathways (2, 3), we examined the possibility that Rho1 interacts directly with PKC1 in vivo. Rho1, tagged at its $NH_2$-terminus with the HA epitope ($^{HA}$Rho1), was immunoprecipitated from yeast extracts, and the resultant immunoprecipitates were analyzed by SDS-PAGE and immunoblotting with anti-PKC1 antibody. PKC1 was co-immunoprecipitated with $^{HA}$Rho1 (FIG. 3A, lanes 4 and 6), suggesting that PKC1 associates with Rho1 in vivo. This interaction was observed both in cells growing at 23° C. and after heat shock.

Figure 3B:
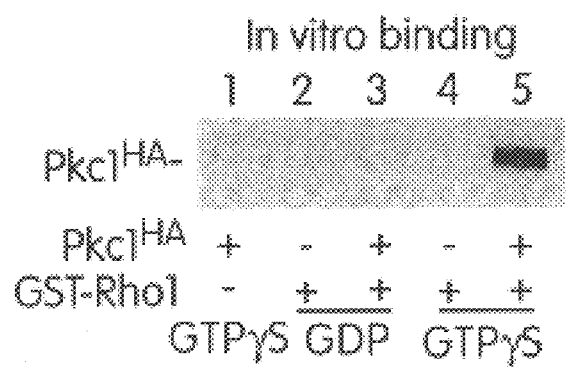

To determine if the association between Rho1 and PKC1 depends on the activation state of Rho1, we examined the effect of different guanine nucleotides on this interaction in vitro. Recombinant glutathione-S-transferase-(GST)-Rho1, immobilized on glutathione agarose beads, was preloaded with either GTPγS or GDP prior to incubation with a yeast extract containing soluble PKC1 tagged at its COOH-terminus with the HA epitope (PKC1$^{HA}$). After washing the beads, bound PKC1$^{HA}$ was detected by SDS-PAGE and immunoblotting with anti-HA antibody. FIG. 3B shows that GTPγS-bound GST-Rho1 associated with PKC1 (lane 5), but GDP-bound protein did not (lane 3).

Figure 4A:
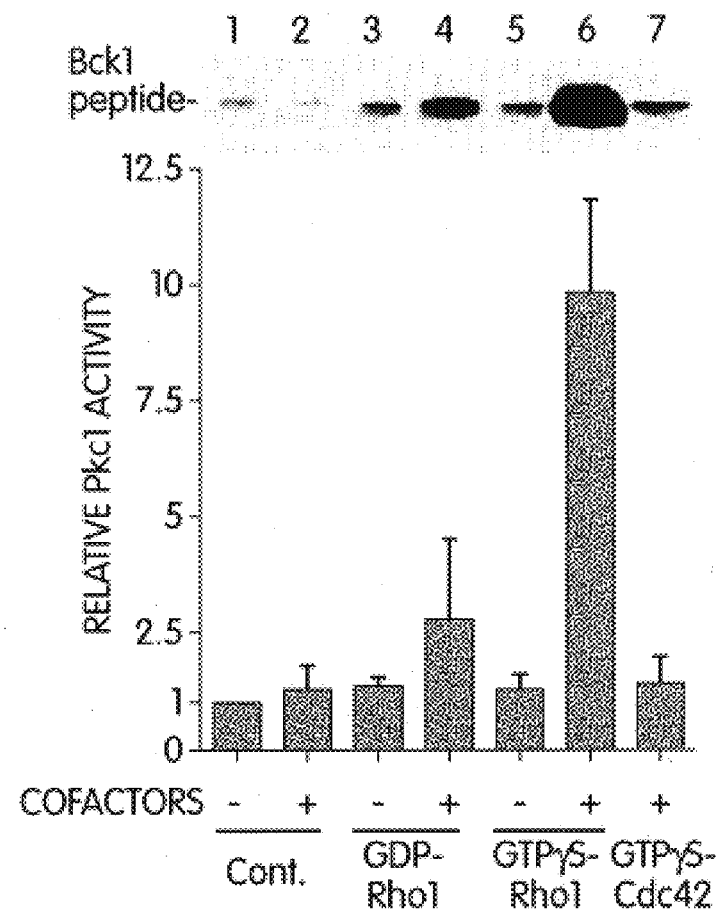
FIGS. 4A–B Rho1 allows cofactors to activate PKC1.
Figure 4B:
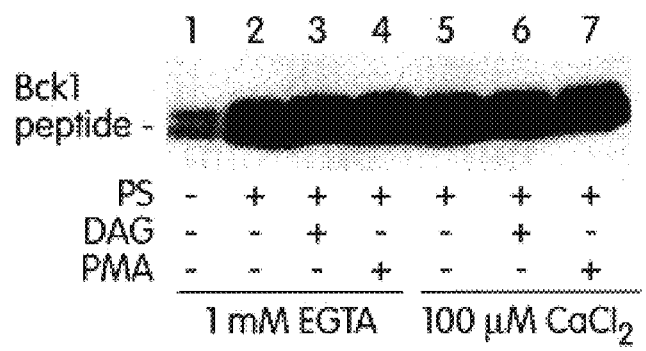

We also tested the possibility that PKC1 activity is stimulated by Rho1. PKC1$^{HA}$ was immunoprecipitated from yeast extracts, and its protein kinase activity was measured in the presence or absence of GST-Rho1 using a synthetic Bck1 peptide as substrate. FIG. 4A shows that GST-Rho1 did not stimulate PKC1 activity alone but, when bound to GTPγS, conferred upon the protein kinase the ability to respond to activating cofactors (PS, DAG, and $Ca^{2+}$). This stimulatory effect is specific to Rho1, because GST-Cdc42 did not confer cofactor-dependent stimulation on PKC 1. In the presence of GTP-bound GST-Rho1, PKC1 was strongly activated by phosphatidylserine (PS) as a lone cofactor (FIG. 4B). The conventional isoforms of mammalian PKC are not stimulated by PS alone (28, 29). In contrast, this behavior is characteristic of the atypical ζ isoform of PKC (28, 30). No additional stimulation was observed by addition of $Ca^{2+}$, DAG, or phorbol ester (PMA) as a DAG substitute. This behavior is also exclusively characteristic of PKCζ (28, 30). Interestingly, the cys-rich region of PKC1, which is predicted to be a DAG-binding domain, has been reported to interact with Rho1 in two-hybrid experiments (19). Therefore, Rho1 may replace DAG in the activation of PKC1.

Figure 5:
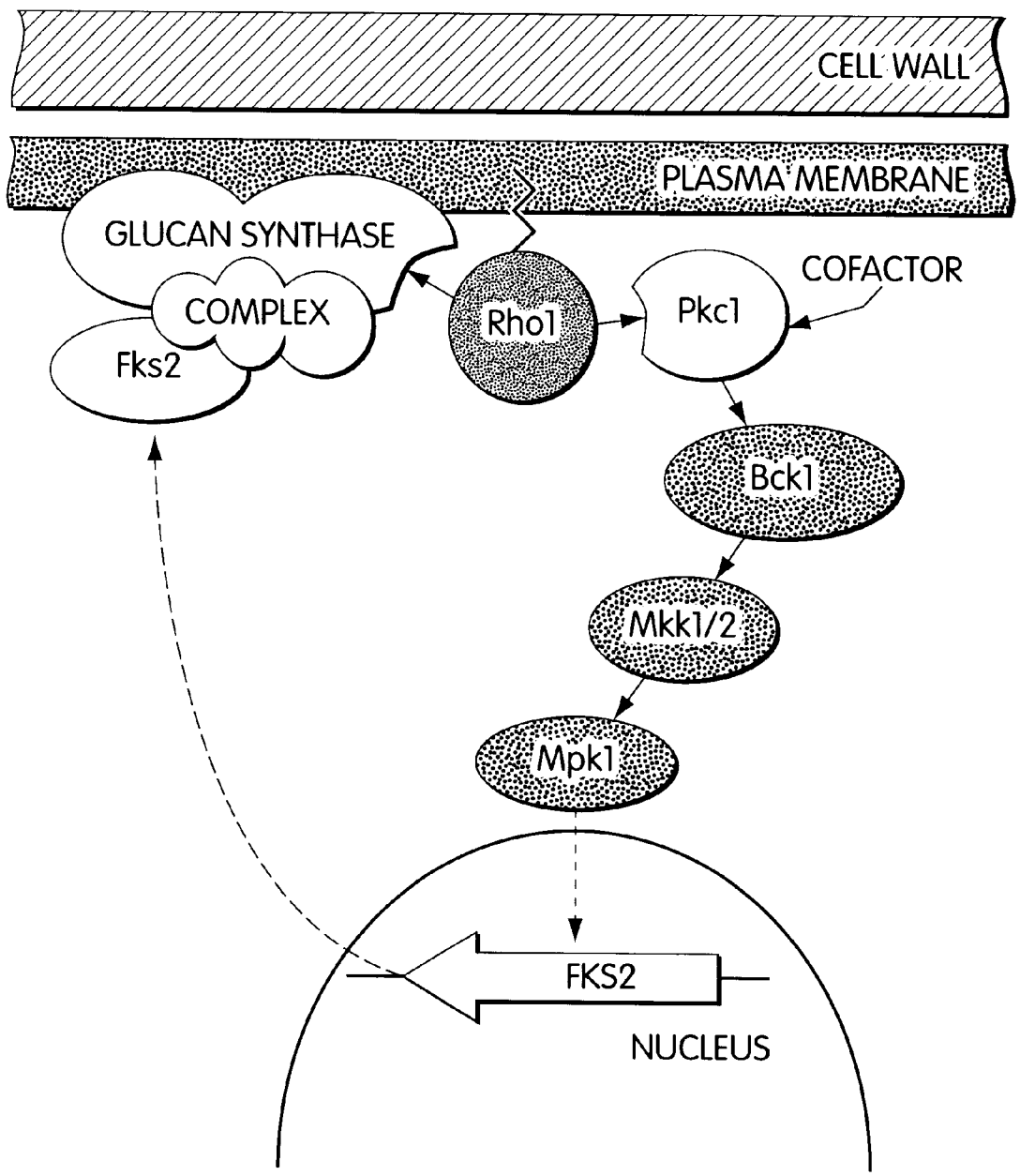
FIG. 5. Model for the dual role of Rho1 in the maintenance of cell integrity.

This study provides the first example of a PKC isoform whose stimulation by cofactors is dependent on a GTPase. We have identified recently a second role for Rho1 in the maintenance of cell integrity. Specifically, Rho1 is an essential component of the 1,3-β-glucan synthase (GS) complex (see Example 2, infra), the enzyme responsible for constructing polymers of 1,3-β-glucan in the cell wall. We have found that thermal induction of the FKS2 gene, which encodes another component of the GS (32, 33), is under the control of PKC1 and MPK1. Based on these findings, we propose the following model. A signal induced by weakness created in the cell wall during growth (and exacerbated at high temperature) stimulates guanine nucleotide exchange of Rho1 at the growth site. The GTP-bound Rho1 stimulates cell wall construction directly by activating GS and indirectly by stimulating PKC1-dependent gene expression in support of this process (FIG. 5).

D. References For Example 1
1. D. E. Levin et al., (1990) Cell 62: 213–224
2. I. Herskowitz (1995) Cell 80: 187–197
3. D. E. Levin and B. Errede (1995) Curr. Opin. Cell. Biol. 7: 197–202
4. Y. Kamada et al., (1995) Genes Dev. 9: 1559–1571
5. M. Watanabe et al., (1994) J. Biol. Chem. 269: 16829–16836
6. B. Antonsson et al., (1994) J. Biol. Chem. 269: 16821–16828
7. A. J. Ridley and A. Hall (1992) Cell 70: 389–399
8. A. J. Ridley et al., (1992) Cell 70: 401–410
9. C. D. Nobes and A. Hall (1995) Cell 81: 53–62
10. C. S. Hill et al., (1995) Cell 81: 1159–1170
11. M. F. Olson et al., (1995) Science 269: 1270–1272
12. A. Minden et al., (1995) Cell 81: 1147–1157
13. O. A. Coso et al, (1995) Cell 81: 1137–1146
14. A. B. Vojtek and J. A. Cooper (1995) Cell 82: 527–529
15. R. Treisman (1995) EMBO J. 14: 4905–4913
16. W. Yamochi et al., (1 994) J. Cell Biol. 125: 1077–1093
17. P. Madaule et al., (1987) PNAS USA 84: 779–783
18. H. Qadota et al., (1 994) PNAS USA 91: 9317–9321
19. H. Nonaka et al, (1995) EMBO J. 14: 5931–5938
20. R. S. Sikorski and P. Hieter (1989) Genetics 122: 19–27
21. R. C. Cadwell and G. F. Joyce (1992) PCR Meth. Appl. 2: 28–32
22. Y. Ohya and D. Botstein (1994) Genetics 138: 1041–1054
23. Y. Zheng et al., (1994) J. Biol. Chem. 269: 2369–2372
24. M-N. Simon et al., (1995) Nature 376: 702–705
25. Z-S. Zhao et al., (1995) Mol. Cell. Biol. 15: 5246–5257
26. E. Manser et al., (1994) Nature, 367: 40–46
27. U. G. Knaus et al., (1995) Science, 269: 221–223
28. Y. Ono et al., (1989) PNAS USA 86: 3099–3103
29. D. J. Burns et al., (1990) J. Biol. Chem. 265: 12044–12051
30. A. Toker et al., (1994) J. Biol. Chem. 269: 32358–32367 et al.
32. P. Mazur et al., (1995) Mol. Cell. Biol. 15: 5671–5681
33. S. B. Inoue et al., (1995) Eur. J. Biochem. 231: 845–854

Example 2

Identification of Yeast Rho1 GTPase as a Regulatory Subunit of 1,3-β-Glucan Synthase A. Overview 1,3-β-glucan synthase is a multi-enzyme complex that catalyzes the synthesis of 1,3-β-linked glucan, a major structural component of the yeast cell wall. Temperature-sensitive mutants in the essential Rho-type GTPase, Rho1, displayed thermolabile glucan synthase activity, which was restored by the addition of recombinant Rho1. Glucan synthase from mutants expressing constitutively active Rho1 did not require exogenous GTP for activity. Rho1 copurified with 1,3-β-glucan synthase and was found to associate with the Gsc1/Fks1 subunit of this complex in vivo. Both proteins were found to reside predominantly at sites of cell wall remodeling. Therefore, it appears that Rho1 is a regulatory subunit of 1,3-β-glucan synthase.

The cell wall of the budding yeast Saccharomyces cerevisiae is required to maintain cell shape and integrity (1). Vegetative proliferation requires that the cell remodel its wall to accomodate growth, which during bud formation, is polarized to the bud tip. The main structural component responsible for the rigidity of the yeast cell wall is 1,3-β-linked glucan polymers with some branches through 1,6-β-linkages. The biochemistry of the yeast enzyme catalyzing the synthesis of 1,3-β-glucan chains has been studied extensively (2,3), but little is known at the molecular level about the genes encoding subunits of this enzyme. Only a pair of closely related proteins (Gsc1/Fks1 and Gsc2/Fks2) are known to be subunits of the 1,3-β-glucan synthase (GS) (3–5). GS activity in many fungal species, including *S. cerevisiae*, requires GTP or a non-hydrolyzable analog (eg. GTPγS) as a cofactor, suggesting that a GTP-binding protein stimulates this enzyme (2,6). In this report, we demonstrate that the Rho1 GTPase is an essential regulatory component of the GS complex.

Figure 6A:
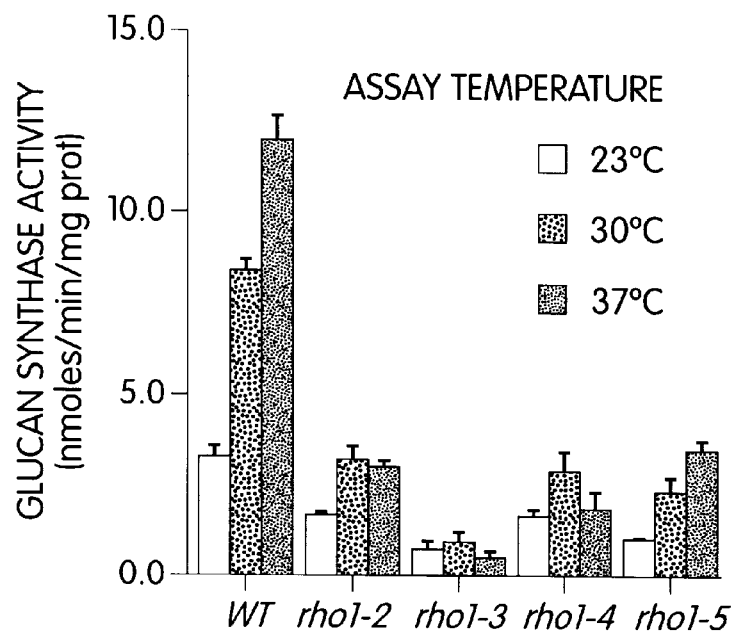
FIGS. 6A–C. GS activity from rho1 mutants (See reference of Example 3).
Figure 6B:
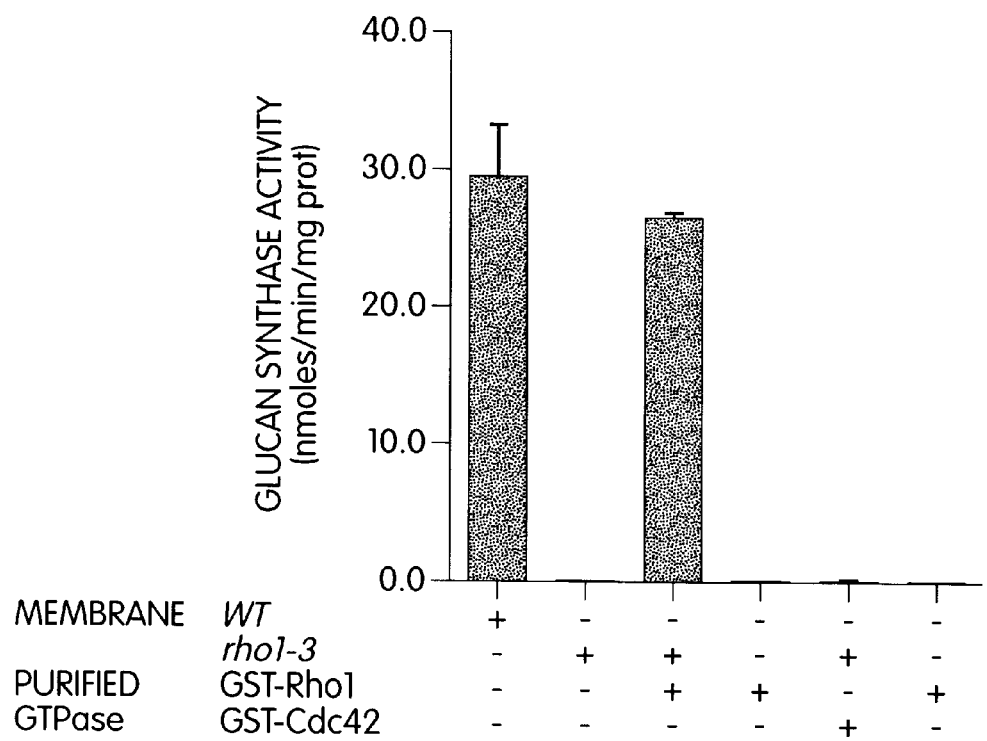
Figure 6C:
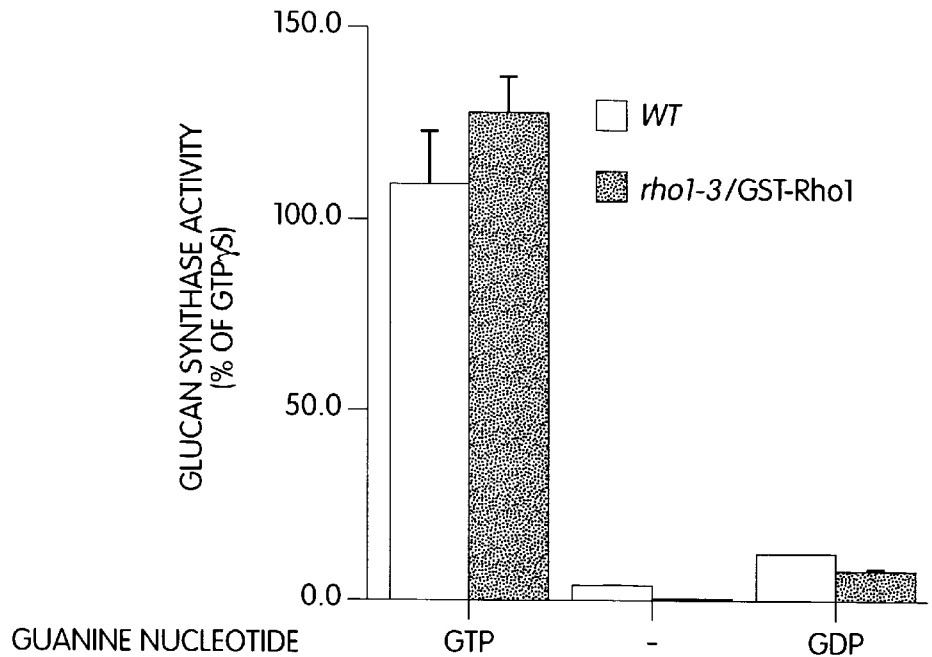

The Saccharomyces RHO1 (Ras homologous) gene encodes a small GTPase that resides at sites of growth (7), and whose function is essential for viability (M. S. Boguski et al. (1992) New Biol. 4:408). Based on phenotypic analyses of conditional rho1 mutants, we and others have suggested that the normal function of Rho1 is to maintain cell integrity (7,9). Conditional rho1 mutants are hypersensitive to Calcofluor white and echinocandin B, drugs that interfere with cell wall assembly, suggesting that this gene is involved in wall construction (10). To determine if Rho1 is required for glucan synthesis, we measured GS activity in extracts of temperature-sensitive rho1 mutants grown at permissive temperature. GS activity from wild-type cells increased as a function of assay temperature from 23° C. to 30° C. to 37° C. (FIG. 6A). All of the rho1 mutants tested displayed reduced levels of activity at each temperature relative to wild-type. Moreover, the enzyme from all but one mutant (rho1-5) exhibited some level of thermolability, suggesting that RHO1 function is required for GS activity. Therefore, we tested the ability of purified, recombinant glutathione-S-transferase (GST)-Rho1 to restore GS activity to membrane fractions from the most impaired rho1 mutant (rho1-3). Membranes from this mutant were virtually devoid of activity at 37° C. FIG. 6B shows that GS activity was restored fully by the addition of GTPγS-bound GST-Rho1, but not GST-Cdc42, another member of the Rho-family of GTPases. GTPγS could be replaced with GTP, but not GDP (FIG. 6C). These results indicate that the GS-deficient mutant membranes lack only Rho1 function.

Figure 7:
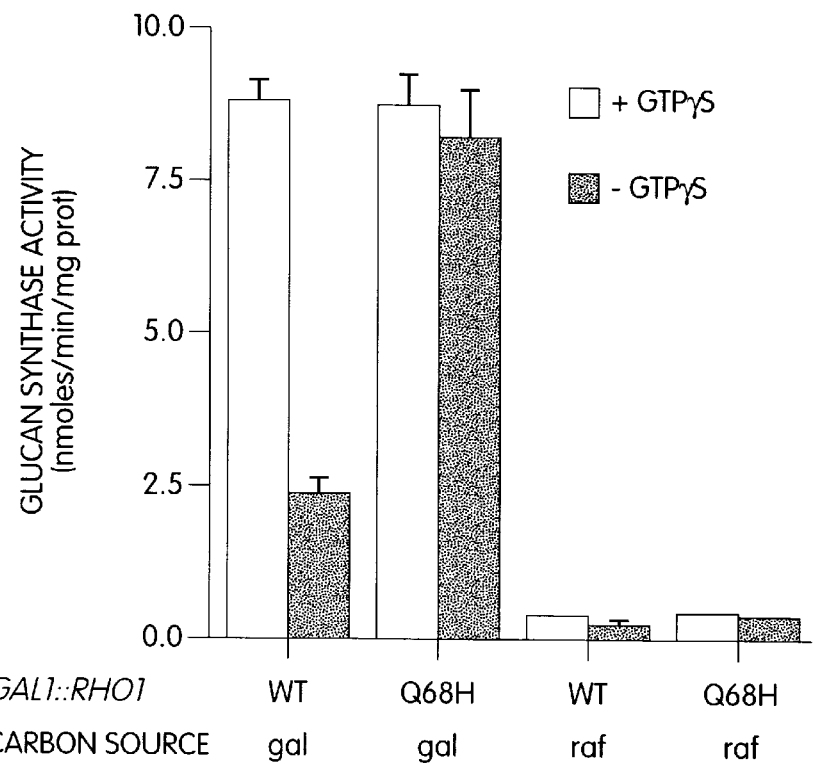
FIG. 7. GS activity in a constitutively active RHO1 mutant is GTP independent. Cultures of rho1-3 cells harboring plasmids with either RHO1 or RHO1-Q68H (M. S. Boguski et al. (1992) New Biol. 4:408) under the control of the inducible GAL1 promoter were grown at room temperature in medium containing 2% raffinose (repressing conditions). Galactose was added (to 2%) to half of each culture, and cells were cultured for an additional 4 h to induce expression of RHO1. GS activity in membrane fractions was assayed at 37° C. in the presence or absence of GTPγS.

We also examined GS activity from yeast cells expressing an constitutively active RHO1 allele (RHO1-Q68H). The analogous mutation in Ras results in a protein that is impaired for the ability to hydrolyze GTP and has transforming potential in mammalian cells (11). The GTP requirement of GS activity was examined in membranes obtained from rho1-3 cells overexpressing RHO1 or RHO1-Q68H under the inducible control of the GAL1 promoter (FIG. 7). Under inducing conditions (galactose), expression of RHO1-Q68H resulted in GS activity that was independent of exogenous GTP. By contrast, GS activity in membranes from cells overexpressing RHO1 was largely dependent on GTP. Similar results were obtained with another activated allele (RHO1-G19V; 12). Taken together, these results indicate that GS activity requires functional Rho1 in the GTP-bound state.

Figure 8A:
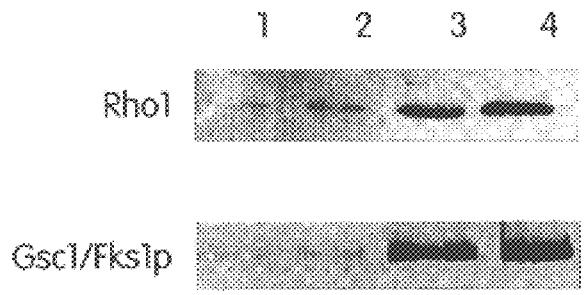
FIGS. 8A–B. Rho1 and Gsc1/Fks1 are enriched during purification of GS. GS was purified from a wild-type strain (A451; 3).
Figure 8B:
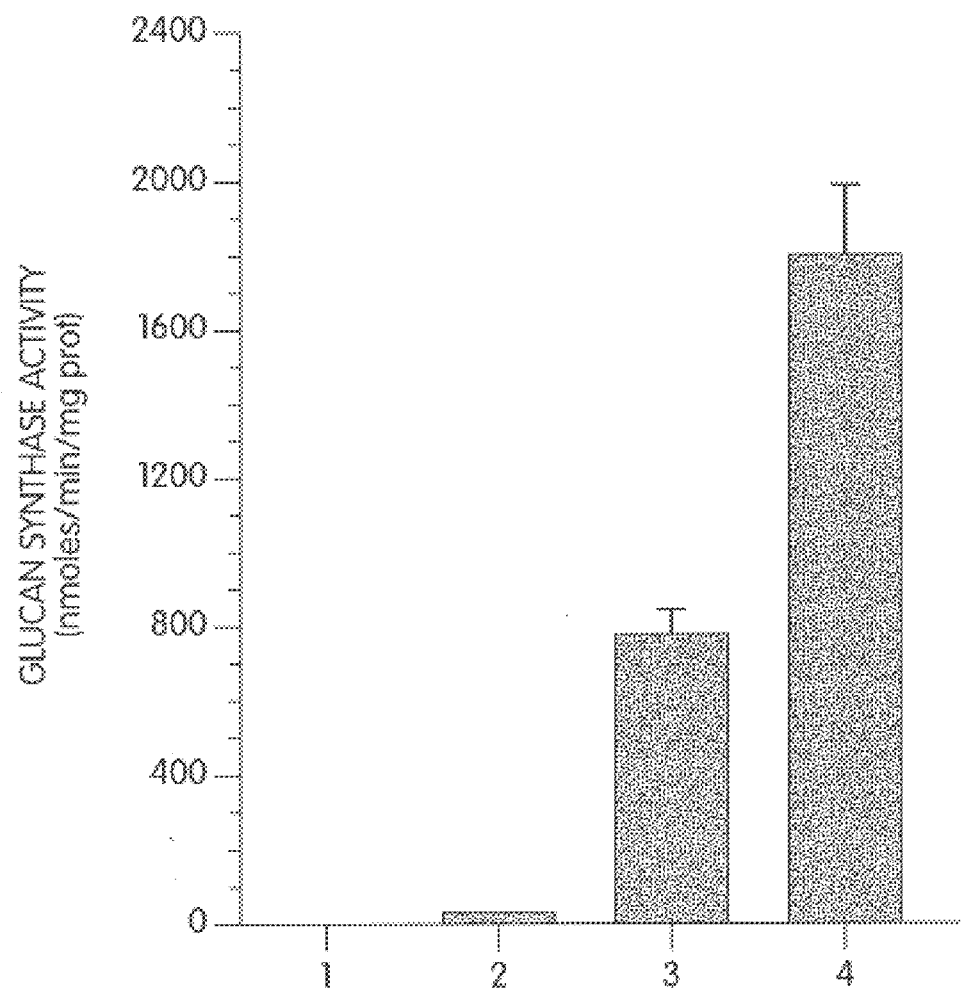
Figure 9A:
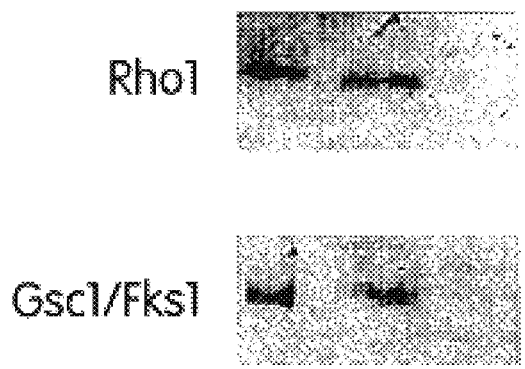
FIGS. 9A–B.

To determine if Rho1 is a component of the GS complex, we monitored the levels of Rho1 during purification of GS activity. The enzyme was purified by successive product entrapments following extraction from membranes (3). FIGS. 8A–B shows that both Rho1 and Gsc1/Fks1 were enriched in the partially purified GS. The specific activity of GS was increased approximately 700-fold through purification, whereas Rho1 was enriched approximately 400-fold. GS purified from the rho1-5 mutant was deficient in GS activity despite normal levels of Rho1 and Gsc1/Fks1 proteins (data not shown). To determine if Rho1 copurifies with GS because it physically associates with the GS complex, the partially purified enzyme was immunoprecipitated with either of two monoclonal antibodies against Gsc1/Fks1. The resultant immunoprecipitates were analyzed by SDS-PAGE and immunoblotting with anti-Rho1 antibody. FIG. 9A shows that Rho1 coimmunoprecipitates with Gsc1/Fks1.

Figure 9B:
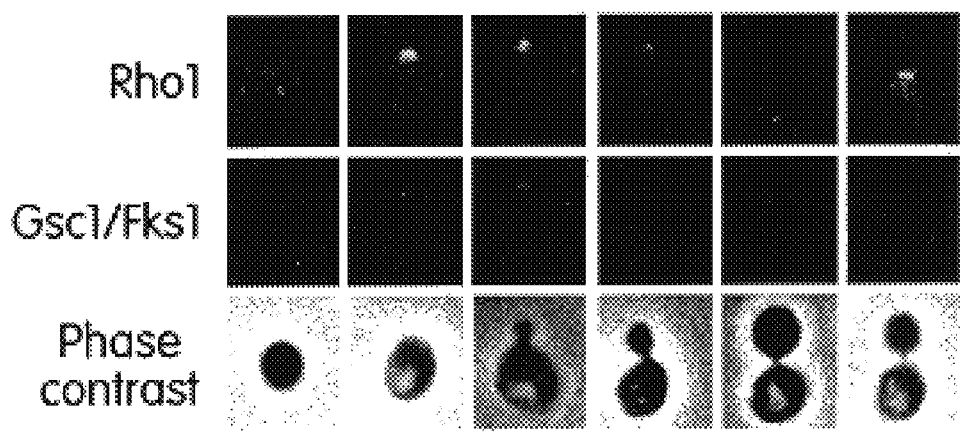

Finally, we examined the localization of Rho1, tagged at its NH$_2$-terminus with the influenza hemagglutinin (HA) epitope ($^{HA}$Rho1), and Gsc1/Fks1 in growing yeast cells. Rho1 is known to be located at the bud tip (the site of polarized growth) during bud formation, and at the mother/bud neck (the site of septum formation) during cytokinesis (7). Indirect immunofluorescence of cells double labeled with anti-HA and anti-Gsc1/Fks1 antibodies revealed that Gsc1/Fks1 colocalizes with $^{HA}$Rho1 (FIG. 9B). These results strongly suggest that Rho1, like Gsc1/Fks1,is a component of the GS complex. This complex is redistributed through the cell cycle so as to reside at sites of cell wall remodeling.

We have shown recently that Rho1 interacts with and activates the PKC1 protein kinase (see Example 1, supra). Like rho1 mutants, pkc1 mutants display cell integrity defects that result from a deficiency in cell wall construction. However, several observations indicate that PKC1 is not involved in the activation of GS. First, mutants in PKC1 display no defect in GS activity (14). Second, overexpression of PKC1 did not restore GS activity to rho1 mutants (15). Third, PKC1 was not detected in the purified GS complex (16). Therefore, we propose that Rho1 plays at least two distinct regulatory roles in the maintenance of cell integrity. One is the activation of GS and the other is the stimulation of PKC1 for signal transduction. Rho1 may serve to coordinate, both spacially and temporally, several events required for effective cell wall remodeling. Both the GTP requirement for GS activity, and the structure of fungal PKCs are evolutionarily conserved (6,17), suggesting that the dual function of Rho1 may be conserved as well.

C. References And Notes For Example 2

34. V. J. Cid et al., (1995) *Microbiol. Rev.* 59:345; F. M. Klis, (1994) *Yeast* 10:851
35. P. C. Mol et al., (1994) *J. Biol. Chem.* 269:31267
36. S. B. Inoue et al, (1995) *Eur. J. Biochem.* 231:845
37. C. M. Douglas et al., (1994) *PNAS USA* 91:12907; A. F. J. Ram et al.,(1995) *FEBS Lett.* 358:165; P. Garett-Engele et al., (1995) *Mol. Cell. Biol.* 15:4103
38. P. Mazur et al., ibid, p. 5671.
39. P. J. Szaniszlo et al., (1985) *J. Bacteriol.* 161:1188
40. W. Yamochi et al., (1994) *J. Cell. Biol.* 125:1077
41. P. Madaule et al., (1987) *PNAS USA* 84:779
42. H. Qadota et al., (1994) *PNAS USA* 91:9317
43. Yeast strains YOC752 (rho1-2), YOC729 (rho1-3), YOC754 (rho1-4), YOC755 (rho1-5) and YOC764 (wild-type) were used in this study. YOC752, YOC729, and YOC755 displayed hypersensitivity to Calcofluor white and echinocandin B at 23° C.
44. C. J. Der et al., (1986) *Cell* 44:167
45. YPH499 cells carrying plasmids with wild-type RHO1 (pYO762), RHO1-G19V (pYO906) under the control of the GAL1 promoter, or vector alone (pYO761) were used. Cells were incubated in galactose medium for 10 h, and GS activity associated with the membrane fraction was measured (3). Most of the GS activity from cells with pYO906 was GTPγS-independent, whereas only 15–20% of the activity was GTPγS-independent in the control strains.

46. A temperature-sensitive pkc1 strain (SYT11-12A) and its isogenic wild-type strain (YS3-6D) [S. Yoshida el al., (1992) *Mol. Gen. Genet.* 231:337] were grown in YPD (yeast extract/peptone/dextrose) at 23° C. A pkc1Δ strain (DL376) and its isogenic wild-type (DL100) [D. E. Levin and E. Bartlett-Heubusch, (1992) *J. Cell Biol.* 116:1221] were grown at 23° C. in YPD containing 10% sorbitol. GS activities were assayed at 23° C. and at 37° C.
47. Mutants used were rho1-3 and rho1-5 carrying PKC1 on a multicopy plasmid (pYO910), or vector alone (pYO324).
48. Partially purified enzyme fraction (second product entrapment) was analyzed by immunoblotting with anti-PKC1 antibody (S. Yoshida, unpublished).
49. T. Toda, et al, (1993) *EMBO J.* 12: 1987; G. Paravicini et al, *Yeast*, in press.
50. Crude yeast extracts were prepared as described [Y. Kamada el al., (1995) *Genes Dev.* 9:1559], and stored at −80° C. in lysis buffer supplemented with 33% glycerol. Membrane fractions, where indicated, were obtained from crude extracts and 1,3-β-glucan synthase (GS) activity was measured as described in (2) with the following modifications: UDP-[$^3$H] glucose was used as the substrate and α-amylase (1U/40 μl) was added to reaction mixtures to eliminate the contribution of [$^3$H] glucose incorporation into glycogen. For all GS assays, the mean and standard error for four experiments is shown.
51. Recombinant GST-Rho1 and GST-Cdc42 were expressed in Sf9 insect cells, and purified as described previously [Y. Zheng et al., (1994) *J. Biol. Chem.* 269:2369].
52. A series of protein sample dilutions was analyzed by immunoblotting with guinea pig anti-Rho1 antiserum or mouse anti-Gsc1/Fks1 monoclonal antibodies (T2B8; 3). The amount of antigens was estimated by densitometry.
53. Goat anti-mouse IgG-agarose (20 μl; Sigma) was incubated with 500 μl media from monoclonal antibody cultures for 5 h at 37° C. The agarose beads were washed 5 times with phosphate-buffered saline and twice with Buffer A (0.4 CHAPS, 0.08% cholesteryl hemisuccinate, 50 mM Tris-Cl, pH 7.5, 1 mM EDTA, 8 μM GTPγS and 33% glycerol). Partially purified GS (1.8 μg) was added and the reaction mixtures were further incubated for 2 h at 37° C. After washing the beads four times with Buffer A, the bound complexes were analyzed by immunoblotting with anti-Rho1 antiserum or anti-Gsc1/Fks1 monoclonal antibodies (T2B8).
54. Cells of haploid strain YOC785, which bears a rho1Δ and the HA-tagged RHO1 gene (13) on a centromere plasmid (pYO904) were double stained with mouse monoclonal antibody against Gsc1/Fks1 (T2B8) and rabbit anti HA-antibody (Boehringer), as described previously [J. R. Pringle et al., (1989) *Methods Cell Biol.*, 31:357]. Secondary antibodies were FITC-conjugated anti-mouse IgG (Cappel) and TRITC-conjugated anti-rabbit IgG (Cappel). Control strains (YPH499 for $^{HA}$Rho1 and gsc1Δ for Gsc1/Fks1) produced no signals in single staining experiments. The secondary antibodies did not cross-react with the eterologous primary antibodies. Some internal punctate staining of Gsc1/Fks1 that did not olocalize with $^{HA}$Rho1 may represent secretory intermediates.

Example 3

Yeast Geranylgeranyl Protein Transferase I is Essential for Membrane Localization of Rho1 GTPase and 1,3-β-Glucan Synthase Activity The abbreviations used in Example 3 are: GGPTase I, geranylgeranyl protein transferase I; GST, glutathone-S-transferase; HA, influenza hemagglutinin; ORF open reading frame; GS, 1,3-β-glucan synthase.

A. Overview

Protein prenylation, farnesylation and geranylgeranylation, is a posttranslational reaction which requires the covalent attachment of a hydrophobic tail, isoprenoid (C15 or C20), to the C-terminal cysteine residue of the substrate proteins (1). Prenylation is necessary for many proteins to interact with membranes and to locate at proper intracellular places. Many lines of evidence have been accumulated to show that small GTPases require prenylation to gain full functionality,(1, 2).

Genes encoding subunits of each prenyltransferase have been cloned in the yeast *Saccharomyces cerevisiae*. The genes CAL1 (3) (also known as CDC43 (4)) and DPR1 (5) (also known as RAM1) encode β subunits of the yeast GGPTase I and FTase, respectively, and RAM2 encodes the common α subunit (6). The α subunit, β subunit and component A of the yeast GGPTase II are encoded by BET4, BET2 and MSI4, respectively (7). An alignment of the homologous regions of the three β subunit sequences (positions 159–350 of the Cal1/Cdc43 sequence) reveals 32–40% identity each other (3). This region contains novel repeat motifs (M. S. Boguski et al. (1992) New Biol. 4:408). The repeats have a length of 44–45 residues and there are three repeats in the Cal1p/Cdc43p sequence. The repeats are conserved in the central Gly-Gly-Phe-Gly-Gly sequence region. The α subunit of isoprenyl transferases also possesses distinct internal repetitive sequence containing tryptophan. Hydrophobic bonds between the side chains of the conserved tryptophan and phenylalanine may be important for forming heterodimer.(M. S. Boguski et al. (1992) New Biol. 4:408).

Among prenyltransferase mutants, a mutation in the GGPTase I β subunit gene was the first to be isolated and characterized. cal1-1 was identified originally as a mutation resulting in a $Ca^{2+}$-dependent phenotype (9). The cal1-1 mutant simultaneously exhibits a homogeneous terminal phenotype with a G2/M nucleus and a small bud at 37° C .(9). Independent screening of yeast cell cycle mutants which accumulated enlarged unbudded cells identified six other alleles, cdc43-2~cdc43-7 (10). Yeast GGPTase I is essential for yeast cell growth, since deletions of the CAL1 gene result in a lethal phenotype (3). However, GGPTase I is no longer essential, when the dosage of the two GTPases, Rho1p (11, 12) and Cdc42p (13), are artificially elevated (14). Since the yeast GGPTase I prenylates these two GTPases, Cdc42p and Rho1p are implicated genetically as the only two essential substrates of GGPTase I (14). CAL1/CDC43 is necessary not only for the function of the small GTPases but also for membrane localization of the small GTPases. An increase in soluble Cdc42p is observed in the cdc43-2 strain grown at the restrictive temperature (15).

This study was undertaken to understand the molecular lesions caused by loss of the GGPTase I function, using the seven temperature-sensitive mutations in the CAL1/CDC43 gene. All of the mutation sites were determined at the nucleotide level. An increase in soluble Rho1p was observed in the cal1-1 strain grown at the restrictive temperature. Futhermore, GS activity was dramatically reduced in the cal1-1 mutant strains. Several phenotypic differences were observed among the cal1/cdc43 mutations, possibly due to the alteration of substrate specificity caused by the mutations.

B. Experimental Procedures

Materials.—YPD medium contained 1% Bacto-yeast extract (Difco Laboratories, Detroit, Mich.), 2% polypeptone (Nihon Chemicals, Osaka), and 2% glucose (Wako Chemicals, Tokyo). YPD supplemented with 100 mM or 300 mM $CaCl_2$ was used as $Ca^{2+}$-rich medium. Other standard media are described elsewhere (16).

DNA manipulation—DNA fragments containing the cdc43 mutations were cloned by gap repair (17). The pCAL-F9 plasmid containing the 2.8 kb SphI-PstI fragment of the CAL1/CDC43 gene was digested with Nsp(7524)V and EcoT22I and introduced into the cdc43 strains (cdc43-2~cdc43-7). Transformation of the plasmid containing the Nsp(7524)V-EcoT22I gap resulted in repair of the gap to yield plasmids in which the gap was repaired by gene conversion with the chromosomal sequences. The gap-repaired plasmids were recovered from yeast, and its Nsp(7524)V-EcoT22I fragment was subcloned into the Nsp(7524)V-EcoT22I gap of pCAL-F9. Then, the resulting plasmids YCpT-cdc43-2~YCpT-cdc43-7 were introduced into the cdc43 strains. Because the transformants showed a temperature-sensitive phenotype, we concluded that all of the cdc43 mutations resided within the region between the Nsp(7524)V and EcoT22I. Nucleotide sequencing of the 1.0-kb Nsp(7524)V-EcoT22I fragment from the YCpT-cdc43-2~YCpT-cdc43-7 revealed that each of the cdc43 mutants possessed a single base pair change within the ORF.

Production of the anti-Rho1p antibody-The purified GST-Rho1p (64–209) which is a fusion protein of GST with Rho1p from amino acid positions 64 to 209 was minced and emulsified with R-700 (RIBI ImmunoChem Research, Hamilton, Mont.) and the resulting emulsion was used to immunize four guinea pigs. After boost was repeated five times with three-weeks intervals, blood was collected from the animals and one of the immune serum was used in this study. The anti-Rho1p antibody specifically recognized Rho1p. Western blotting analysis showed that there was no other protein band detected in the lysates of cells expressing human rhoA in place of RHO1.

Cell fractionation experiments. Cell fractionation experiments were performed using techniques described by Ziman et al. (15). Briefly, cells were grown at 23° C. to mid log phase, and approximately $5 \times 10^8$ cells were collected, washed with water, resuspended in 0.1 ml of lysis buffer (0.8 M sorbitol, 1 mM EDTA, 10 mM N-(2-hydroxyethyl)-piperazine-N'-2-ethanesulfonic acid pH 7.0) with 0.5 mM PMSF, and lysed on ice by vortexing with 400–500 mm acid-washed glass beads (Sigma). Greater than 80% lysis was verified by light microscopy. After addition of 0.4 ml of lysis buffer, cell lysates were spun at 390×g for 1 min at 4° C. The supernatant was then spun at 436,000×g for 20 min at 4° C., and the pellets were resuspended in the same volume of lysis buffer. To assess the relative amount of Rho1p and Cdc42p in each fraction, equal volumes of each fraction were loaded onto a sodium dodecyl sulfate-12.5% polyacrylamide gel for immunoblot analysis. Guinea pig polyclonal antibody against Rho1p and mouse monoclonal antibody against HA (12CA5, Boeringer Mannheim, Germany) were used at 1:500 and 1:100, respectively. Alkaline phosphatase-conjugated goat anti-guinea pig IgG and anti-mouse IgG were used at 1:5000. Antibody-antigen complexes were detected with 5-bromo-4-chloro-3-indoryl-phosphate and nitro blue tetrazolium.

C. Results and Discussion

Mutation points of cdc43-2~cdc43-7 were determined after DNA fragments containing the cdc43-2~cdc43-7 mutations were cloned by the gap repair method (17) to yield YCpT-cdc43-2~YCpT-cdc43-7. Based on the subcloning analysis (see Materials and Methods), we concluded that all of the cdc43 mutations resided within the 1.0-kb region between the Nsp(7524)V and EcoT22I, nearly corresponding to the entire coding region of CAL1/CDC43. Nucleotide sequencing of the 1.0-kb Nsp(7524)V-EcoT221 fragment from the YCpT-cdc43-2~YCpT-cdc43-7 revealed that each of the cdc43 mutants possessed a single base pair change within the ORF. FIG. 10 shows the amino acid changes in the cdc43 sequences. cdc43-4 and cdc43-6 resulted from an identical nucleotide change, and hereafter are referred to as cdc43-6. cdc43-5 had a amino acid change at the same position as cdc43-4 and cdc43-6, but resulted in a different amino acid change. FIG. 10 shows that the four cdc43/cal1 mutations (cdc43-5 cdc43-6, cdc43-7, cal1-1) were mapped within the domain homologous to the b-subunits of other protein isoprenyltransferases (a.a. position 159–350). Interestingly enough, these mutations affect the conserved amino acid residues among the subunits of GGPTase I from four different species (3, 18, 19). The other two cdc43 mutations (cdc43-2 and cdc43-3) were mapped outside of the homologous domain.

We have previously shown the functional interaction between RHO1 and CAL1, based on the observation that overproduction of Rho1p suppressed the temperature sensitivity of cal1-1 (See reference of Example 3). In order to know whether the suppression by verproduction of Rho1p was seen only with the cal1-1 allele, we examined the ability of overproduction of Rho1p to suppress the cdc43 mutations. Since the restrictive temperatures of the cdc43 mutants were different, effects of the Rho1p overexpression were examined at five different temperatures (23° C., 28° C., 30° C., 33° C. and 37° C.). We found that the cdc43 mutations were not suppressed effectively by overproduction of Rho1p (Table 1). None of the mutations was suppressed at 37° C., while cal1-1 was suppressed at this temperature. cdc43-2 and cdc43-7 with multicopy RHO1 grew slightly faster than those with vector alone at 30° C., while cal1-1 was suppressed completely at this temperature. Slight growth improvement of cdc43-5 by overproduction of Rho1p was observed only at 23° C. These results indicate that among the cal1/cdc43 mutations so far isolated, cal1-1 is a unique mutation that is effectively suppressed by overproduction of Rho1p.

TABLE 1

Effect of overproduction of Rho1p and Cdc42p in the cal1/cdc43 mutants

| strain | plasmid | growth on YPD | | | | | YPD + Ca | |
|---|---|---|---|---|---|---|---|---|
| | | 23° C. | 28° C. | 30° C. | 33° C. | 37° C. | 33° C. | 37° C. |
| cal1-1 | pYO324 | + | + | ± | − | − | ++ | + |
| | YCpT-CAL1 | ++ | ++ | ++ | ++ | ++ | ++ | ++ |
| | YEpT-RHO1 | ++ | ++ | ++ | ++ | + | ++ | + |
| | YEpT-CDC42 | n.d. | n.d. | n.d. | n.d. | n.d. | n.d. | n.d. |

TABLE 1-continued

Effect of overproduction of Rho1p and Cdc42p in the cal1/cdc43 mutants

| | | growth on YPD | | | | | YPD + Ca | |
|---|---|---|---|---|---|---|---|---|
| strain | plasmid | 23° C. | 28° C. | 30° C. | 33° C. | 37° C. | 33° C. | 37° C. |
| cdc43-2 | pYO324 | ++ | + | ± | − | − | − | − |
| | YCpT-CAL1 | ++ | ++ | ++ | ++ | ++ | ++ | ++ |
| | YEpT-RHO1 | ++ | + | + | − | − | − | − |
| | YEpT-CDC42 | ++ | + | ± | − | − | − | − |
| cdc43-3 | pYO324 | ++ | ++ | ++ | ± | − | − | − |
| | YCpT-CAL1 | ++ | ++ | ++ | ++ | ++ | ++ | ++ |
| | YEpT-RHO1 | ++ | ++ | ++ | ± | − | − | − |
| | YEpT-CDC42 | ++ | ++ | ++ | ± | − | + | − |
| cdc43-5 | pYO324 | + | ± | − | − | − | − | − |
| | YCpT-CAL1 | ++ | ++ | ++ | ++ | ++ | ++ | ++ |
| | YEpT-RHO1 | ++ | ± | − | − | − | − | − |
| | YEpT-CDC42 | ++ | ++ | ++ | ++ | + | ++ | + |
| cdc43-6 | pYO324 | ++ | + | ± | − | − | − | − |
| | YCpT-CAL1 | ++ | ++ | ++ | ++ | ++ | ++ | ++ |
| | YEpT-RHO1 | ++ | + | ± | ± | − | − | − |
| | YEpT-CDC42 | ++ | + | ± | − | − | − | − |
| cdc43-7 | pYO324 | ++ | + | ± | − | − | ± | − |
| | YCpT-CAL1 | ++ | ++ | ++ | ++ | ++ | ++ | ++ |
| | YEpT-RHO1 | ++ | + | + | − | − | ± | − |
| | YEpT-CDC42 | ++ | + | ± | − | − | + | − |

Since overproduction of Rho1p suppressed a mutation of the CAL1/CDC43 gene, we next attempted to examine multicopy suppression of the cdc43 mutations by overproduction of another essential substrate of GGPTase I, Cdc42p. We found that overproduction of Cdc42p suppressed the temperature-sensitive phenotype of cdc43-5 (Table 1); the cdc43-5 mutant with multiple copies of CDC42 grew well at 37 ° C. Among the cdc43 mutations, cdc43-5 was most effectively suppressed by overproduction of Cdc42p; cdc43-3, cdc43-6 and cdc43-7 were suppressed slightly by overproduction of Cdc42p at the intermediate temperature, and cdc43-2 was not suppressed at all at any temperature examined.

Figure 11A:
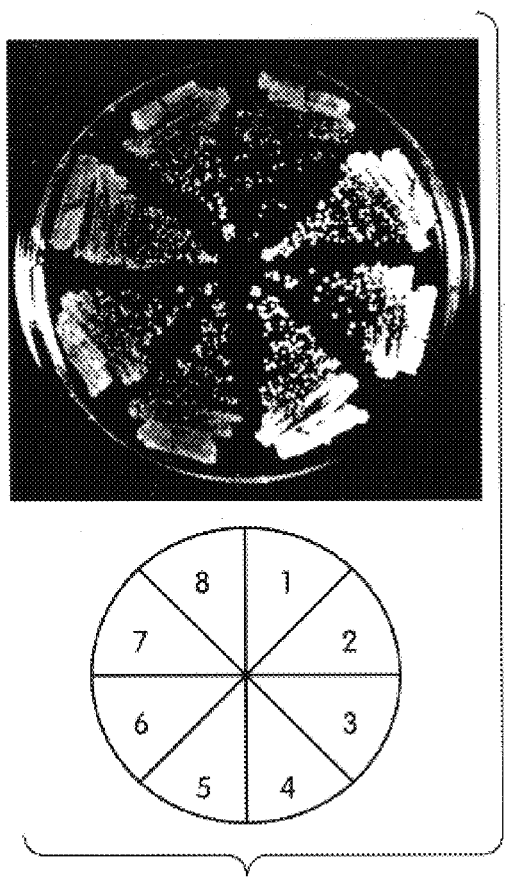
FIGS. 11A–B. Overproduction of CDC42 is toxic in cal1-1 cells. cal1-1 (1), cdc43-2 (2), cdc43-3 (3) cdc43-4 (4) cdc43-5 (5), cdc43-6 (6), cdc43-7 (7) and wild-type strain (M. S. Boguski et al. (1992) New Biol. 4:408) harboring pGAL-CDC42 were streaked on the plate containing glucose FIG. 11A or galactose FIG. 11B, and incubated at 23° C. for 1 week.
Figure 11B:
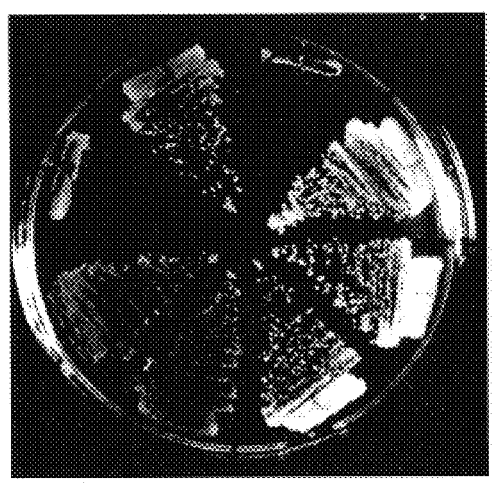
Figure 12:
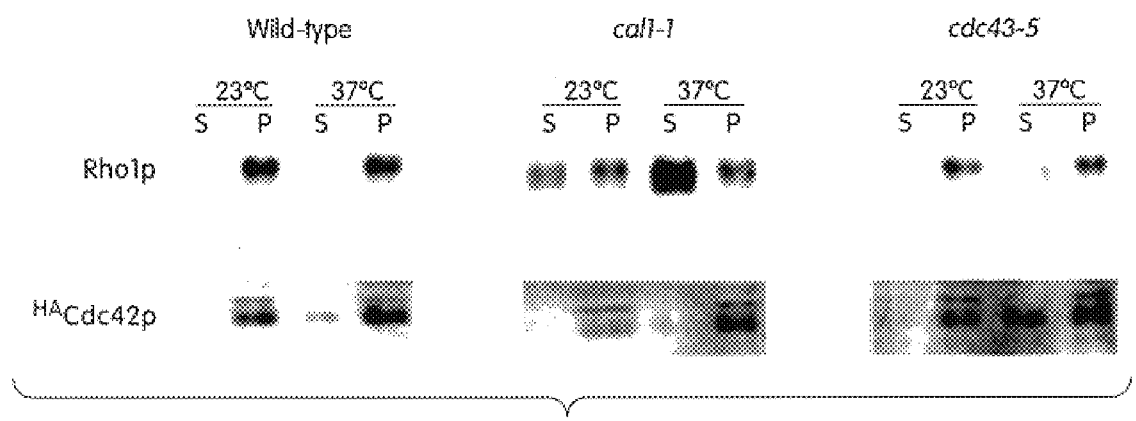
FIG. 12. Fractionation of Rho1p and Cdc42p in wild-type and mutant strains. Yeast strains were grown to midlog phase at the permissive temperature (23° C.), shifted to the restrictive temperature, collected after 2 hr (37° C.), and the cell lysates were prepared. Rho1p was detected by Western blotting analysis with guinea pig polyclonal antibody against Rho1p. In order to express HA-tagged version of Cdc42p, yeast strains transformed with pYO920 were incubated at 23° C. in 2% galactose-containing medium for 6 hr before the temperature shift. HA-tagged version of Cdc42p was detected by Western blotting analysis with 12CA5. WT, YPH500; cal1-1, YOT159-3C; cdc43-5, YOT435-1A.

Several trials to introduce multiple copies of CDC42 into the cal1-1 strain were unsuccessful. Reasoning that overexpression of Cdc42p might be a lethal event in the cal1-1 strain, we attempted to increase the levels of Cdc42p by placing its expression under the control of the GAL1 promoter that was induced by galactose in the medium. The cal1-1 strain with pGAL-CDC42 could grow on solid media containing glucose (FIG. 11A) but did not grow on media containing galactose (FIG. 11B). This growth inhibition was observed at any temperature examined (23° C., 30° C. and 37° C.). Since pGAL-CDC42 was not toxic in the wild-type strain and many of the other cdc43 mutants (FIG. 11B), we concluded that lethality caused by the overexpression of Cdc42p is specific to the cal1-1 mutant. Although CDC42 on a multicopy plasmid is not toxic in cdc43-7, pGAL-CDC42 is dereterious in cdc43-7 (FIG. 11B). This may be due to the fact that the expression level of Cdc42p by pGAL-CDC42 is more than that expressed by multiple copies of CDC42.

cal1-1 was suppressed most effectively by overexpression of Rho1p, while cdc43-5 was suppressed by overexpression of Cdc42p. To test the possibility that the allele-specific suppression is due to substrate specificity of the mutant GGPTase I, we examined the partitioning of Rho1p and Cdc42p in the cal1-1 and cdc43-5 mutant strains. It was already shown that soluble Cdc42p increases in the cdc43-2 strain grown at the restrictive temperature (15), suggesting that membrane localization of small GTPases is dependent on geranylgeranyl modification. We found that the proportion of Rho1p found in the soluble fraction of cal1-1 dramatically increases after the temperature shift (FIG. 12). Rho1p from cdc43-5 strain grown at 37° C. for 2 hr was almost exclusively in the particulate fraction, indicating that increase of soluble Rho1p is specific to cal1-1. The proportion of HA-tagged Cdc42p found in the soluble fraction of cdc43-5 increased after 2 hr incubation at 37° C., while cal1-1 did not affect partitioning of HA-tagged Cdc42p (FIG. 12). Temperature-shift itself did not affect the partitioning of these GTPases in the wild-type control strain. These results suggested that cal1-1 and cdc43-5 specifically impair geranylgeranylation of Rho1p and Cdc42p, respectively.

Figure 13:
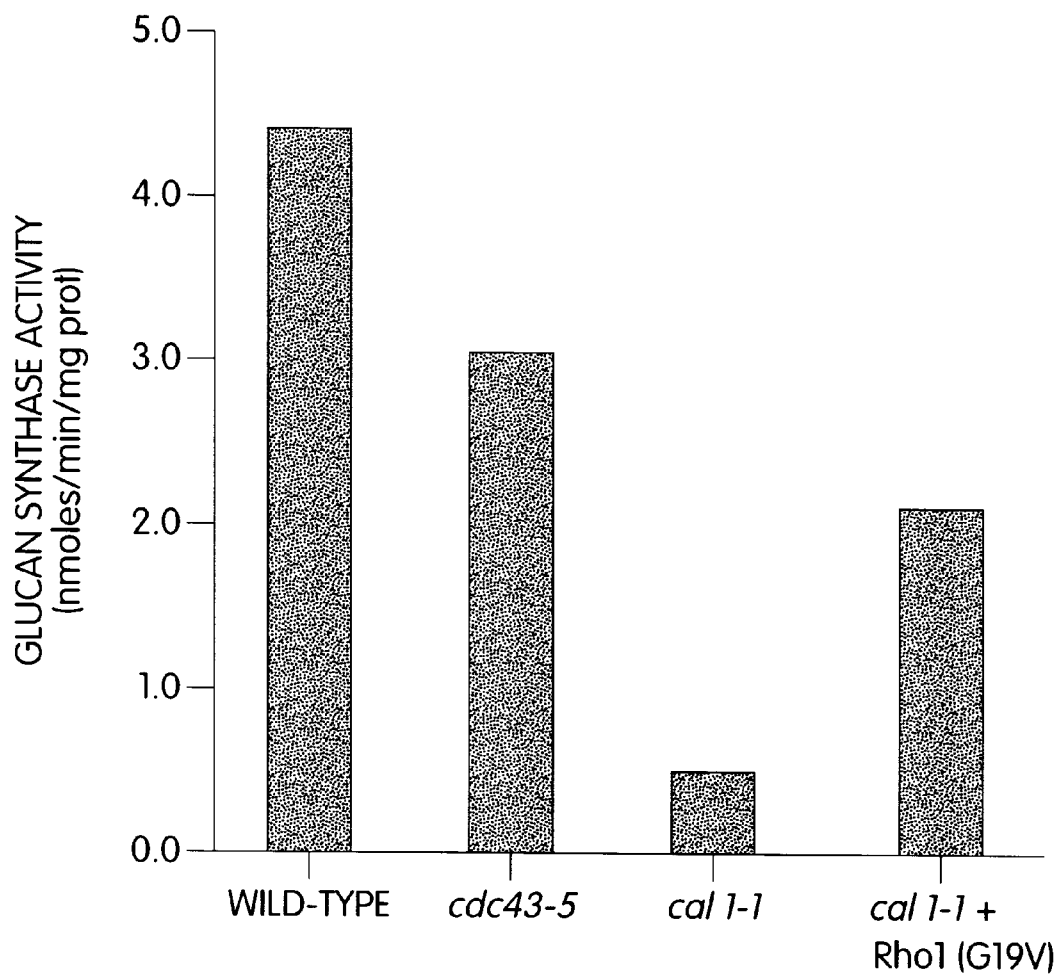
FIG. 13. Reduced GS activity in the membrane fractions of GGPTase I-deficient cells. Cultures of wild-type (YPH500), cal1-1 (YOT159-3C), cdc43-5 (YOT435-1A) cells were grown at room temperature in YPD medium. GS activity in membrane fractions was assayed at 30° C. according to Inoue et al. (1995) Eur. J. Biochem. 231: 845. Reconstitution of GS activity in cal1-1 membrane was performed with recombinant mutant Rho1 (G19V) which is constitutively active for its activity.

We have previously shown that Rho1p is a regulatory subunit of 1,3-β-glucan synthase (see Example 2 above). To directly examine involvement of GGPTase I in the Rho1 function, we measured GS activity in membrane fractions of the cal1-1 and cdc43-5 mutant cells grown at permissive temperature (FIG. 13). We found that cal1-1 displayed dramatically reduced activity relative to wild-type. cdc43-5 mutant instead displayed only slightly reduced activity, probably due to the fact that cdc43-5 impairs geranylgeranylation of Cdc42p more than geranylgeranylation of Rho1. We tested whether purified, recombinant GST-Rho1 restored GS activity to the membrane fraction of the cal1-1 mutant. GS activity was restored by the addition of constitutively activated Rho1. These results indicate that the GS-deficient cal1-1 mutant membrane lack the Rho1 function.

Multiple copies of either Rho1p or Cdc42p suppressed specific alleles of cal1/cdc43 (Table 2): cal1-1 was suppressed effectively by multicopy RHO1, while cdc43-5 was suppressed effectively by multicopy CDC42. Given both Rho1p from the cal1-1 strain and Cdc42p from the cdc43-5 strain accumulate in the soluble fraction, substrate specificipy of the mutant GGPTase I likely accounts for the allele-specific suppression. In our current model, cal1-1 and cdc43-5 selectively impair the in vivo geranylgeranylation of Rho1p and Cdc42p, respectively. This is consistent with observation of the mutant phenotypes; terminal phenotypes of cdc43-5 and cdc42 are undistinguished, and those of cal1-1 and temperature-sensitive rho1 strains are somewhat similar. This is also consistent with our observation that overexpression of Cdc42p is lethal specifically in the cal1-1 strain, because overexpression of Cdc42p likely sequesters the cal1-1 GGPTase I to further impair geranylgeranylatikn of Rho1p. GS activity was dramatically reduced in cal1-1 but not in cdc43-5. Taken together, our genetic and biochemical results suggest that the CAL1/CDC43 GGPTase I has an ability to prenylate the substrate GTPases by some domain-specific, substrate-specific recognition mechanisms.

TABLE 2

Summary of the effect of the GTPases in the cal1/cdc43 mutants

| Phenotype | overproduction | |
|---|---|---|
| | Cdc42p | Rho1p |
| suppression | cdc 43-5 (cdc43-3, −4, −7) | cal1-1 (cdc43-2, −5, −7) |
| deletenous | cal1-1 (cdc43-7) | |

C. References in Example 3
55. W. R. Schafer and J. Rine (1992) Annu. Rev. Genet. 26:209; S. Clarke (1992) Annu. Rev. Biochem. 61:355
56. C. A. Omer and J. B. Gibbs (1994) Mol. Microbiol. 11:219
57. Y. Ohya et al. (1991) J. Biol. Chem. 266:12356
58. D. I. Johnson et al. (1991) Gene 98:149
59. L. E. Goodman el al. (1988) Yeast 4:271
60. B. He et al. (1991) Proc. Natl. Acad. Sci. USA 88:11373
61. K. Fujimura et aL (1994) J. Biol. Chem. 269:9205; G. Rossi et al. (1991) Nature 351:158
62. M. S. Boguski et al. (1992) New Biol. 4:408
63. Y. Ohya et al. (1984) Mol. Gen. Genet. 193:389
64. A. E. M. Adams et al. (1990) J. Cell. Biol. 111:131
65. P. Madaule et al. (1987) Proc. Nati. Acad. Sci. USA 84:779
66. H. Qadota et al. (1994) Proc. Natl. Acad. Sci. USA 91:9317
67. D. I. Johnson and J. R. Pringle (1990) J. Cell. Biol. 111:143
68. Y. Ohya el al. (1993) Mol. Biol. Cell 4:1017
69. M. Ziman et al (1993) ibid. 1307
70. M. Rose et al. (1990) Methods in yeast genetics. A laboratory manual. CSH Lab. Press, CSH, N.Y.
71. T. L. Orr-Weaver et al. (1983) Methods in Enzymol. 101:228
72. M. Diaz et al. (1993) EMBO J. 12:5245
73. F. L. Zhang et al. (1994) J. Biol. Chem. 269:3175
74. H. Qadota et al. (1992) Yeast 8:735
75. Inoue et al. (1995) Eur. J. Biochem. 231: 845

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

We claim:

1. An assay for identifying a compound having potential anti-fungal activity, comprising:

(a) forming a reaction mixture including:
   (i) a fungal geranylgeranyl transferase I (GGPTase I),
   (ii) a GGPTase substrate, and
   (iii) a test compound;
   under conditions wherein, in the absence of the test compound, the GGPTase I and the GGPTase substrate interact; and (b) detecting interaction of the GGPTase substrate with the GGPTase I, wherein a statistically significant decrease in the interaction of the GGPTase substrate and GGPTase I in the presence of the test compound, relative to the level of interaction in the absence of the test compound, indicates a potential anti-fungal activity for the test compound.

2. The assay of claim 1, wherein the GGPTase substrate comprises a peptidyl substrate for the GGPTase comprising a fungal Rho-like GTPase, or a polypeptide portion thereof including at least one of (a) a prenylation site which can be enzymatically prenylated by the GGPTase, or (b) a GGPTase binding sequence which specifically binds the GGPTase.

3. An assay for identifying a compound having potential anti-fungal activity, comprising:

(a) forming a cell-free reaction mixture including:
   (i) a fungal geranylgeranyl transferase I (GGPTase I),
   (ii) a peptidyl substrate for the GGPTase;
   (iii) an activated geranylgeranyl group,
   (iv) a divalent cation, and
   (v) a test compound;

(b) detecting conjugation of the gernaylgernayl group to the peptidyl substrate for the GGPTase in the reaction mixture, wherein a statistically significant decrease in the prenylation of the target polypeptide in the presence of the test compound, relative to the level of prenylation in the absence of the test compound, indicates a potential anti-fungal activity for the test compound.

4. The assay of claim 1, wherein the GGPTase is an active prenyltransferase and the reaction mixture further includes a geranylgeranyl group which the GGPTase adds to the GGPTase substrate, and the step of detecting the interaction of the GGPTase substrate with the GGPTase comprises detecting conjugation of the activated geranylgeranyl group to the GGPTase substrate.

5. The assay of any of claims 4 or 3 wherein at least one of the geranylgeranyl group and the GGPTase substrate comprises a detectable label, and the level of the geranylgeranyl group-conjugated to the GGPTase substrate is quantified by detecting the label in at least one of the GGPTase substrate and the geranylgeranyl group.

6. The assay of claim 1, wherein the step of detecting the interaction of the GGPTase substrate with the GGPTase comprises detecting formation of protein complexes between the GGPTase substrate and the GGPTase.

7. The assay of claim 6, wherein at least one of the GGPTase and the GGPTase substrate comprises a detectable label, and the level of the GGPTase/GGPTase substrate complexes formed in the reaction mixture is quantified by detecting the label in at least one of the GGPTase substrate and the GGPTase.

8. The method of claim 5, wherein the label group is selected from a group consisting of radioisotopes, fluorescent compounds, enzymes, and enzyme co-factors.

9. The assay of claim 5, wherein the GGPTase substrate comprises a fluorescent label having a fluorescent characteristic which is altered by the level of prenylation of the GGPTase substrate.

10. The assay of claim 9, wherein the GGPTase substrate is a dansylated peptide substrate of the fungal GGPTase.

11. The assay of any of claims 4 or 3, wherein the conjugation of the geranylgeranyl group to the GGPTase substrate is detected by antibody binding to the GGPTase substrate or the geranylgeranyl group.

12. The assay of claim 6, wherein the formation of the protein complexes is detected by antibody binding to the GGPTase substrate or the geranylgeranyl group.

13. The assay of any of claims 1 or 3, wherein the reaction mixture is reconstituted protein mixture of the GGPTase and the GGPTase substrate.

14. The assay of any of claims 1 or 3, wherein the reaction mixture comprises a cell lysate, including the GGPTase.

15. The assay of any of claims 2 or 3 wherein the fungal Rho-like GPTase is selected from the group consisting of Rho1, Rho2, Rsr1/Bud1 and Cdc42.

16. The assay of claim 1, wherein the reaction mixture is a whole cell in contact with the test compound, the whole cell comprising a heterologous nucleic acid recombinantly expressing one or more of the fungal GGPTase subunits and GGPTase substrate.

17. The assay of claim 1, wherein the reaction mixture is a whole cell in contact with the test compound, the whole cell comprising a heterologous reporter gene construct comprising a reporter gene in operable linkage with a transcriptional regulatory sequence sensitive to intracellular signals transduced by the interaction of the GGPTase substrate and GGPTase.

18. The assay of any of claims 1 or 3, wherein the assay is repeated for a variegated library of at least 100 different test compounds.

19. The assay of any of claims 1 or 3, wherein the test compound is selected from the group consisting of small organic molecules, and natural product extracts.

20. The assay of any of claims 2 or 3, wherein one or more of the GGPTase and peptidal substrate for the GGPTase are derived from a pathogen infecting a human which pathogen is involved in mycotic infection.

21. The assay of claim 20, wherein the mycotic infection is a mycosis selected from a group consisting of candidiasis, aspergillosis, mucormycosis, blastomycosis, geotrichosis, cryptococcosis, chromoblastomycosis, penicilliosis, conidiosporosis, nocaidiosis, coccidioidomycosis, histoplasmosis, maduromycosis, rhinosporidosis, monoliasis, para-actinomycosis, and sporotrichosis.

22. The assay of claim 20, wherein the human pathogen is selected from a group consisting of *Candida albicans, Candida stellatoidea, Candida tropicalis, Candida parapsilosis, Candida krusei, Candida pseudotropicalis, Candida quillermondii, Candida rugosa, Aspergillus fumigatus, Aspergillus flavus, Aspergillus niger, Aspergillus nidulans, Aspergillus terreus, Rhizopus arrhizus, Rhizopus oryzae, Absidia corymbifera, Absidia ramosa*, and *Mucor pusillus*.

23. The assay of claim 20, wherein the human pathogen is *Pneumocystis carinii*.

24. The method of claim 3, wherein the GGPTase includes a subunit, and wherein one or both of the GGPTase subunit and the Rho-like GTPase are fusion protein.

25. The method of claim 3, wherein the level of interaction of the GGPTase and Rho-like GTPase is detected by detecting prenylation of the Rho-like GTPase.

26. The assay of claim 3, wherein the peptidyl substrate includes a tetrapeptide CAAX.

27. The assay of claim 3, wherein the peptidyl substrate is a dansylated peptide.

28. The assay of any of claims 4 or 3, wherein at least one of the geranylgeranyl group and the GGPTase substrate comprises a detectable label, and the level of the geranylgeranyl group-conjugated to the GGPTase substrate is quantified by detecting the label in the geranylgeranyl-conjugated GGPTase substrate.

29. The assay of claim 6, wherein at least one of the GGPTase and the GGPTase substrate comprises a detectable label, and the level of the GGPTase/GGPTase substrate complexes formed in the reaction mixture is quantified by detecting the label in the GGPTase/GGPTase substrate complexes.

* * * * *

UNITED STATES PATENT AND TRADEMARK OFFICE
CERTIFICATE OF CORRECTION

PATENT NO. : 6,117,641

DATED : September 12, 2000

INVENTOR(S) : Vivian Berlin, David E. Levin, Yoshikazu Ohya

It is certified that error appears in the above-identified patent and that said Letters Patent is hereby corrected as shown below:

In column 51, line 50, delete "gernaylgernayl" and insert therefor --geranylgeranyl--.

In column 51, line 54, delete "target polypeptide" and insert therefor --peptidyl substrate for the GGPTase--.

In column 52, line 18, delete "group-conjugated" and insert therefor --group conjugated--.

UNITED STATES PATENT AND TRADEMARK OFFICE
CERTIFICATE OF CORRECTION

PATENT NO. : 6,117,641

DATED : September 12, 2000

INVENTOR(S) : Vivian Berlin, David E. Levin, Yoshikazu Ohya

It is certified that error appears in the above-identified patent and that said Letters Patent is hereby corrected as shown below:

In column 52, line 51, delete "Rho-like GTPase" and insert therefor --peptidyl substrate--.

In column 54, line 3, delete "Rho-like GTPase are fusion protein." and insert therefor --peptidyl substrate are fusion proteins.--

In column 54, line 5, delete "Rho-like GTPase" and insert therefor --peptidyl substrate--.

In column 54, line 6, delete "Rho-like GTPase" and insert therefor --peptidyl substrate--.

In column 54, line 15, delete "group-conjugated" and insert therefor --group conjugated--.

Signed and Sealed this

First Day of May, 2001

Attest:

NICHOLAS P. GODICI

Attesting Officer   Acting Director of the United States Patent and Trademark Office